(12) United States Patent
Levin

(10) Patent No.: US 10,786,476 B2
(45) Date of Patent: Sep. 29, 2020

(54) COMBINATION THERAPY

(71) Applicant: IMBRIA PHARMACEUTICALS, INC., Rancho Santa Fe, CA (US)

(72) Inventor: Andrew D. Levin, Newton, MA (US)

(73) Assignee: IMBRIA PHARMACEUTICALS, INC., Boston, MA (US)

( * ) Notice: Subject to any disclaimer, the term of this patent is extended or adjusted under 35 U.S.C. 154(b) by 72 days.

(21) Appl. No.: 16/078,325

(22) PCT Filed: Feb. 23, 2017

(86) PCT No.: PCT/US2017/019000
§ 371 (c)(1),
(2) Date: Aug. 21, 2018

(87) PCT Pub. No.: WO2017/147220
PCT Pub. Date: Aug. 31, 2017

(65) Prior Publication Data
US 2019/0314319 A1    Oct. 17, 2019

Related U.S. Application Data

(60) Provisional application No. 62/449,722, filed on Jan. 24, 2017, provisional application No. 62/449,708, filed on Jan. 24, 2017, provisional application No. 62/298,977, filed on Feb. 23, 2016.

(51) Int. Cl.
*C07C 69/40* (2006.01)
*A61K 31/225* (2006.01)

(52) U.S. Cl.
CPC ............ *A61K 31/225* (2013.01); *C07C 69/40* (2013.01)

(58) Field of Classification Search
CPC .................................................. C07C 69/40
See application file for complete search history.

(56) References Cited

U.S. PATENT DOCUMENTS

| | | | |
|---|---|---|---|
| 3,624,397 A | 11/1971 | Honeycutt et al. | |
| 3,634,397 A * | 1/1972 | Thompson et al. | A23D 9/013 536/119 |
| 5,693,850 A | 12/1997 | Birkhahn et al. | |
| 8,912,304 B2 | 12/2014 | Bruggeman et al. | |
| 2004/0220137 A1 | 11/2004 | Sauermann | |
| 2011/0273646 A1 | 11/2011 | Fukagawa et al. | |
| 2012/0122978 A1 | 5/2012 | Henderson | |
| 2014/0303232 A1 | 10/2014 | Baryza et al. | |

OTHER PUBLICATIONS

Kandeel et al. Journal of Dispersion Science and Technology 2012, 33, 949-954 (Year: 2012).*
CAS Registry No. 1346413-49-7, which entered STN on Nov. 25, 2011 (Year: 2011).*
Miyazaki, 2001, Fatal Propionic Acidemia in Mice Lacking Propionyl-CoA Carboxylase and Its Rescue by Postnatal, Liver-specific Supplementation via a Transgene, J. Biol. Chem., vol. 276(38): pp. 35995-35999, The American Society for Biochemistry and Molecular Biology, Inc.
Peters,2012, Mouse Models for Methylmalonic Aciduria, PLOS One, vol. 7(7):e40609 (12 pages).
Spiekerkoetter, 2010, Mitochondrial Fatty Acid Oxidation Disorders: Pathophysiological Studies in Mouse Models, J Inherit Metab Dis., vol. 33(5):pp. 539-546, doi:10.1007/s10545-010-9121-7.
Berge, 1977, Pharmaceutical salts, J Pharm Sci., vol. 66(1): pp. 1-19.
PUBCHEM-CID 101936505, Dec. 18, 2015 (8 pages).
International Preliminary Report on Patentability dated Sep. 7, 2018, for International Patent Application PCT/US2017/019000 with International filing date Feb. 23, 2017 (6 pages).
Attya et al., "Endogenous lipase catalyzed transesterification of olive oil fats. The formation of isomeric and oligomeric triacylglycerols: Formation of isomeric and oligomeric triglycerides", Journal of Mass Spectrometry, vol. 47, No. 9, Sep. 1, 2012 (Sep. 1, 2012), pp. 1247-1253, XP55456359, GB ISSN: 1076-5174, DOI: 10.1002/ims.3029.
Tsuchiya D et al: "Formation of a new ester compound between triglyceride and dicarboxylic acid catalyzed by lipase", Journal of Molecular Catalysis. B, Enzymatic, Elsevier, Amsterdam, NL, vol. 35, No. 1-3, Aug. 1, 2005 (Aug. 1, 2005), pp. 52-56, XP027658821, ISSN: 1381-1177.
Ward et al., "New Fat Products: Glyceride Esters of Adipic Acid," The Journal of American Oil Chemists' Society, vol. 36, pp. 667-671, Dec. 1959, 5 pages.
Zerkowski et al., "Selectively Functionalized Glycerol/Diacid Dendrimers via Click Chemistry of Azido Fatty Acids", Journal of the American Oil Chemists' Society (JAOCS), vol. 88, No. 3, Sep. 26, 2010 (Sep. 26, 2010), pp. 403-413, XP55622417, DE ISSN: 0003-021X, DOI: 10.1007/si1746-010-1675-x.

* cited by examiner

*Primary Examiner* — Matthew P Coughlin
(74) *Attorney, Agent, or Firm* — Brown Rudnick LLP; Adam M. Schoen

(57) ABSTRACT

The present disclosure provides certain combination therapy technologies that are particularly useful for treating one or more diseases, disorders, or conditions that may be related to abnormal metabolism. In some embodiments, provided technologies provides combinations of TCA cycle acids and ketone bodies. In some embodiments, provided technologies provides combinations of TCA cycle acids and other carboxylic acids.

2 Claims, 2 Drawing Sheets

COMBINATION THERAPY

RELATED APPLICATION

This application is a U.S. national stage entry of International Patent Application No. PCT/US2017/019000, with international filing date Feb. 23, 2017, which claims priority to United States Provisional Application Nos. 62/298,977, filed Feb. 23, 2016, 62/449,708, filed Jan. 24, 2017, and 62/449,722, filed Jan. 24, 2017, the entirety of each of which is incorporated herein by reference.

BACKGROUND

Many diseases are related to abnormal metabolism. There is need to treat such diseases.

SUMMARY

In some embodiments, the present disclosure encompasses the recognition that combinations of TCA cycle intermediates, e.g., TCA cycle acids, and ketone bodies are particularly useful for treating various diseases that are related to abnormal metabolism. In some embodiments, the present disclosure provides technologies, e.g., compounds, compositions, methods, etc., relating to a combination of one or more TCA cycle intermediates and one or more ketone bodies for treatment of various diseases. In some embodiments, such a combination is unexpectedly effective, for example, when compared to technologies using TCA cycle intermediates or ketone bodies alone.

In some embodiments, a TCA cycle intermediate for use in accordance with the present disclosure is one that is produced in a subject (e.g., to whom provided combination therapy is to be administered) at a low level, for example due to, a disease, genetic mutation, function loss of an enzyme, etc. . . . . Alternatively or additionally, in some embodiments, a ketone body for use in accordance with the present disclosure is one that is produced at a low level in a subject (e.g., to whom provided combination therapy is to be administered), for example due to abnormal ketogenesis. In some embodiments, provided combination therapy provides, for example, increased energy production to certain cells, tissues and/or organs, such as brain, heart, etc.

In some embodiments, the present disclosure provides combinations of, a TCA cycle intermediate, e.g., a TCA cycle acid, and a ketone body that are "physical" combinations of individual compounds, e.g., of a first compound that comprises and/or is metabolized to produce a TCA cycle acid moiety or entity, or derivative thereof (which first compound may be a TCA cycle acid or derivative thereof), together with a second compound that comprises and/or is metabolized to produce a ketone body moiety or entity, or derivative thereof (which second compound may be a ketone body or derivative thereof). In some embodiments, the present disclosure provides combinations that are "chemical" combinations, wherein a TCA cycle intermediate moiety and a ketone body moiety are both present in the same chemical compound (which may optionally be termed a "combination compound"); in some such embodiments, these moieties are connected to one another by way of at least one backbone moiety, e.g., a glycerol moiety. In some particular embodiments, the present disclosure provides combination compounds whose structure comprises at least one glycerol backbone moiety wherein at least one, and optionally all, of the —OH groups is substituted with either a moiety selected from the group consisting of TCA cycle intermediate moieties, ketone body moieties, and combinations thereof. In some embodiments, the present disclosure provides combination compounds whose structure comprises a plurality of such substituted glycerol backbone moieties, each of which is linked to one another via a linker moiety that may be or comprise a TCA cycle diacid or triacid moiety. In some embodiments, a combination for use in accordance with the present disclosure includes both physical and chemical combinations.

In some embodiments, the present disclosure provides compounds that provide chemical combinations of one or more TCA cycle acids and one or more ketone bodies.

In some embodiments, the present disclosure encompasses the recognition that combinations of TCA cycle intermediates, e.g., TCA cycle acids and/or other energy sources, such as carboxylic acids that can be metabolized to provide ketone bodies, acetyl-CoA and/or propionyl-CoA, are particularly useful for treating various diseases that are related to abnormal metabolism. In some embodiments, the present disclosure provides technologies, e.g., compounds, compositions, methods, etc., relating to a combination of one or more TCA cycle intermediates and one or more carboxylic acids, for example, that can be metabolized in human bodies to provide ketone bodies, for treatment of various diseases. In some embodiments, a carboxylic acid can be metabolized to provide acetyl-CoA (e.g., butyric acid ($CH_3(CH_2)_2COOH$), caprylic acid ($CH_3(CH_2)_6COOH$), etc.) through e.g., beta-oxidation. In some embodiments, a carboxylic acid can be metabolized to provide propionyl-CoA through e.g., beta-oxidation. In some embodiments, a carboxylic acid can be metabolized to provide acetyl-CoA and propionyl-CoA (e.g., heptanoic acid ($CH_3(CH_2)_5COOH$)) through e.g., beta-oxidation. In some embodiments, as appreciated by a person having ordinary skill in the art, through e.g., ketogenesis, acetyl-CoA can be used to provide one or more ketone bodies. By providing acetyl-CoA, provided technologies, among other things, can provide TCA cycle replenishment. In some embodiments, provided technologies provide dual mode of TCA cycle replenishment, by providing one or more TCA acids (e.g., succinic acid) and by providing other carboxylic acids (e.g., butyric acid, caprylic acid, etc.) which can be metabolized to provide, e.g., acetyl-CoA. In some embodiments, such a combination is unexpectedly effective, for example, when compared to technologies using TCA cycle intermediates, carboxylic acids, or ketone bodies alone. In some embodiments, provided compounds can, expectedly, be delivered in large quantities, e.g., on the order of >1 grams/kg, through direct oral administration, e.g., direct drinking. In some embodiments, such compounds have unexpectedly good flow properties (not being too viscous) and taste (e.g., not being excessively bitter) to enable such large-quantity delivery. In some embodiments, a combination is provided as a chemical combination. In some embodiments, the present disclosure provides compounds that comprise one or more TCA cycle intermediate moieties and one or more carboxylic acid moieties. In some embodiments, in provided compounds the one or more TCA cycle intermediate moieties and the one or more carboxylic acid moieties are connected via ester groups, optionally through one or more diol or polyol moieties. In some embodiments, a provide compound is a compound of formula I, or a pharmaceutically acceptable salt thereof, as described in the present disclosure.

In some embodiments, a TCA cycle intermediate for use in accordance with the present disclosure is one that is produced in a subject (e.g., to whom provided combination therapy is to be administered) at a low level, for example due to, a disease, genetic mutation, function loss of an enzyme, etc. In some embodiments, a carboxylic acid for use in one that can provide, for example, with or without metabolism, a compound that is produced in a subject at a low level, for example due to, a disease, genetic mutation, function loss of an enzyme, etc. . . . . . In some embodiments, a carboxylic acid, after metabolism, provides a ketone body that is produced at a low level in a subject (e.g., to whom provided combination therapy is to be administered), for example due to abnormal ketogenesis. In some embodiments, a carboxylic acid provides acetyl-CoA and/or propionyl-CoA after being metabolized. In some embodiments, a carboxylic acid provides acetyl-CoA after being metabolized. In some embodiments, a carboxylic acid provides propionyl-CoA after being metabolized. In some embodiments, a carboxylic acid provides acetyl-CoA and propionyl-CoA after being metabolized. In some embodiments, provided combination therapy provides, for example, increased energy production to certain cells, tissues and/or organs, such as brain, heart, etc.

In some embodiments, the present disclosure provides combinations of, a TCA cycle intermediate, e.g., a TCA cycle acid, and another agent as described herein (e.g., that is or is metabolized to a ketone body, acetyl-CoA and/or propionyl-CoA) that are "physical" combinations of individual compounds, e.g., of a first compound that comprises and/or is metabolized to produce a TCA cycle acid moiety or entity, or derivative thereof (which first compound may be a TCA cycle acid or derivative thereof), together with a second compound, for example, a compound having the structure of R'—COOH, that is or comprises and/or is metabolized to produce a ketone body, acetyl-CoA and/or propionyl-CoA moiety or entity, or derivative thereof (which second compound may be a ketone body or derivative thereof). In some embodiments, the present disclosure provides combinations that are "chemical" combinations, wherein a TCA cycle intermediate moiety and a carboxylic acid moiety, whose corresponding carboxylic acid may be metabolized to provide a ketone body, acetyl-CoA and/or propionyl-CoA, are both present in the same chemical compound (which may optionally be termed a "combination compound"); in some such embodiments, these moieties are connected to one another by way of at least one backbone moiety, e.g., a diol or polyol, such as glycerol, moiety. In some particular embodiments, the present disclosure provides combination compounds whose structure comprises at least one diol or polyol (e.g., glycerol) backbone moiety wherein at least one, and optionally all, of the —OH groups is substituted with either a moiety selected from the group consisting of TCA cycle intermediate moieties, carboxylic acid moieties (e.g., R'—C(O)O— or R'—C(O)—), and combinations thereof. In some embodiments, the present disclosure provides combination compounds whose structure comprises a plurality of such substituted diol or polyol (e.g., glycerol) backbone moieties, each of which is linked to one another via a linker moiety that may be or comprise a TCA cycle diacid or triacid moiety. In some embodiments, a combination for use in accordance with the present disclosure includes both physical and chemical combinations.

In some embodiments, the present disclosure provides compounds that provide chemical combinations of one or more TCA cycle acids and one or more carboxylic acids, and optionally one or more diols and/or polyols.

Among other things, the present disclosure recognizes that compositions comprising TCA cycle acid moieties, ketone body moieties, and/or carboxylic acid moieties (e.g., R'—C(O)O— or R'—C(O)— whose corresponding acid R'—C(O)OH can be metabolized to provide one or more ketone bodies, acetyl-CoA and/or propionyl-CoA) can be extremely difficult for pharmaceutical formulation. In some embodiments, for example, they cannot be administered at high enough quantities to be efficacious. In some embodiments, certain compositions, for example, those comprising free hydroxyl groups (e.g., of diols or polyols) and/or free carboxylic acid groups can have so high viscosity that they cannot be readily formulated and/or administered. Additionally or alternatively, certain compositions, for example, some of those having free carboxylic acid groups (e.g., of succinic acid), can be very unpalatable, rendering oral administration difficult if not impossible. In some embodiments, the present disclosure provides compounds and/or compositions that have good flow property for formulation, and/or good taste (e.g., no or tolerable bitterness) for oral administration. In some embodiments, provided compounds are suitable for direct oral administration. In some embodiments, provided compounds are of such flow property and/or taste so that they are suitable for direct oral administration by direct drinking by a subject. In some embodiments, provided compounds can be administered in high quantities, e.g., at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3, 3.5, 4 or 5 g/kg.

In some embodiments, the present disclosure provides a compound having the structure of formula I:

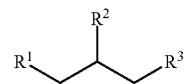

or a salt thereof, wherein:

each of $R^1$, $R^2$ and $R^3$ is independently —H, —OH, R', or —OC(O)R, or may be independently and optionally taken together with a hydrogen atom on the carbon atom to which it is attached to form an oxo group;

each R and R' is independently linear or branched $C_1$-$C_{100}$ aliphatic wherein one or more —$CH_2$— units are independently and optionally replaced with —O—, —C(O)—, —CH(OH)— or —C(O)O—, and any two or more R or R' groups may be linked by one or more linear or branched, bivalent or polyvalent, $C_1$-$C_{100}$ hydrocarbon group wherein one or more —$CH_2$— units are independently and optionally replaced with —O—, —C(O)—, —CH(OH)— or —C(O)O—;

at least one of $R^1$, $R^2$ and $R^3$ is —OC(O)R; and wherein when each ester group of the compound of formula I is hydrolyzed, each hydrolysis product is independently a compound selected from (i) a TCA cycle acid or a salt thereof, (ii) a compound that is, contains, or can be metabolized by a human body to contain a ketone body or ketone body moiety, or a salt thereof, and (iii) an alcohol compound.

In many embodiments, at least one such hydrolysis product is a TCA cycle acid or salt thereof. Alternatively or additionally, in many embodiments, at least one such hydrolysis product is a ketone body or comprises a ketone body moiety, and/or the alcohol compound is glycerol. In some embodiments, at least one hydrolysis product can be metabolized by a human body to provide a ketone body, or ketone body moiety, or a salt thereof (e.g., example carboxylic acids described in the present disclosure).

In some embodiments, a provided compound has the structure of formula I:

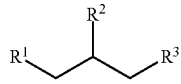
I or a salt thereof, wherein:

each of $R^1$, $R^2$ and $R^3$ is independently —H, —OH, R', or —OC(O)R, or may be independently and optionally taken together with a hydrogen atom on the carbon atom to which it is attached to form an oxo group;

each R and R' is independently linear or branched $C_1$-$C_{100}$ aliphatic wherein one or more —$CH_2$— units are independently and optionally replaced with —O—, —C(O)—, —CH(OH)— or —C(O)O—, and any two R or R' groups may be linked by one or more linear or branched, bivalent or polyvalent, $C_1$-$C_{100}$ hydrocarbon group wherein one or more —$CH_2$— units are independently and optionally replaced with —O—, —C(O)—, —CH(OH)— or —C(O)O—;

at least one of $R^1$, $R^2$ and $R^3$ is —OC(O)R; and wherein when each ester group of the compound of formula I is hydrolyzed, each of the hydrolysis product is independently a compound selected from a TCA cycle acid or a salt thereof, or a ketone body or a salt thereof, and glycerol;

at least one hydrolysis product is a TCA cycle acid; and at least one hydrolysis product is a ketone body.

In some embodiments, a provided compound has the structure of formula I:

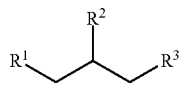
I or a salt thereof, wherein:

each of $R^1$, $R^2$ and $R^3$ is independently —H, —OH, R', or —OC(O)R, or may be independently and optionally taken together with a hydrogen atom on the carbon atom to which it is attached to form an oxo group;

each R and R' is independently linear or branched $C_1$-$C_{100}$ aliphatic wherein one or more —$CH_2$— units are independently replaced with —O—, —C(O)—, —CH(OH)— or —C(O)O—, and any two R or R' groups may be linked by one or more linear or branched, bivalent or polyvalent, $C_1$-$C_{100}$ hydrocarbon group wherein one or more —$CH_2$— units are independently replaced with —O—, —C(O)—, —CH(OH)— or —C(O)O—;

at least one of $R^1$, $R^2$ and $R^3$ is —OC(O)R; and wherein when each ester group of the compound of formula I is hydrolyzed, each of the hydrolysis product is independently a compound selected from a TCA cycle acid or a salt thereof, or a ketone body or a salt thereof, and glycerol;

at least one hydrolysis product is a TCA cycle acid; and at least one hydrolysis product is a ketone body.

In some embodiments, a provided compound has the structure of formula I:

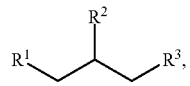
I or a salt thereof, wherein:

each of $R^1$, $R^2$ and $R^3$ is independently —H, —OH, R, or R—C(O)O—, or may be independently and optionally taken together with a hydrogen atom on the carbon atom to which it is attached to form an oxo group;

each R is independently linear or branched $C_1$-$C_{100}$ aliphatic wherein one or more —$CH_2$— units are independently and optionally replaced with —O—, —C(O)—, —CH(OH)—, or —C(O)O—, and any two or more R groups may be linked by one or more linear or branched, bivalent or polyvalent, $C_1$-$C_{100}$ hydrocarbon group wherein one or more —$CH_2$— units are independently and optionally replaced with —O—, —C(O)—, —CH(OH)—, or —C(O)O—;

at least one of $R^1$, $R^2$ and $R^3$ is R—C(O)O—; and wherein when each ester group of the compound of formula I is hydrolyzed into its corresponding —OH and —COOH groups, each hydrolysis product is independently a compound selected from a TCA cycle acid or a salt thereof, a $C_2$-$C_{20}$ diol or polyol, and R'—C(O)OH or a salt thereof; and R' is $C_1$-$C_{20}$ aliphatic wherein one or more —$CH_2$— units are independently and optionally replaced with —O—, —C(O)—, —CH(OH)—, or —C(O)O—.

In some embodiments, a provided compound has the structure of formula I:

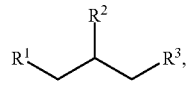
I or a salt thereof, wherein:

each of $R^1$, $R^2$ and $R^3$ is independently —H, —OH, R, or R—C(O)O—, or may be independently and optionally taken together with a hydrogen atom on the carbon atom to which it is attached to form an oxo group;

each R is independently linear or branched $C_1$-$C_{100}$ aliphatic wherein one or more —$CH_2$— units are independently and optionally replaced with —O—, —C(O)—, —CH(OH)—, or —C(O)O—, and any two or more R groups may be linked by one or more linear or branched, bivalent or polyvalent, $C_1$-$C_{100}$ hydrocarbon group wherein one or more —$CH_2$— units are independently and optionally replaced with —O—, —C(O)—, —CH(OH)—, or —C(O)O—;

at least one of $R^1$, $R^2$ and $R^3$ is R—C(O)O—; and wherein when each ester group of the compound of formula I is hydrolyzed into its corresponding —OH and —COOH groups, each hydrolysis product is independently a compound selected from a TCA cycle acid or a salt thereof, a $C_2$-$C_{20}$ diol or polyol, and R'—C(O)OH or a salt thereof;

R' is $C_1$-$C_{20}$ aliphatic wherein one or more —$CH_2$— units are independently and optionally replaced with —O—, —C(O)—, —CH(OH)—, or —C(O)O—; and at least one hydrolysis product is a TCA cycle acid or a salt thereof.

In some embodiments, at least one hydrolysis product is a TCA cycle acid or a salt thereof, at least one hydrolysis product is a $C_2$-$C_{20}$ diol or polyol, and at least one hydrolysis product is R'—C(O)OH or a salt thereof. In some embodiments, R'—C(O)OH is a linear fatty acid with even number of carbon atoms.

In some embodiments, a provided compound has the structure of formula I, wherein:

each of $R^1$, $R^2$ and $R^3$ is independently —H, —OH, R, or R—C(O)O—;

each R is independently linear or branched $C_1$-$C_{100}$ aliphatic wherein one or more —$CH_2$— units are independently and optionally replaced with —O—, —C(O)—, —CH(OH)—, or —C(O)O—, and any two or more R groups may be linked by one or more linear or branched, bivalent or polyvalent, $C_1$-$C_{100}$ hydrocarbon group wherein one or more —$CH_2$— units are independently and optionally replaced with —O—, —C(O)—, —CH(OH)—, or —C(O)O—;

at least one of $R^1$, $R^2$ and $R^3$ is R—C(O)O—; and wherein when each ester group of the compound of formula I is hydrolyzed into its corresponding —OH and —COOH groups, each hydrolysis product is independently a compound selected from a TCA cycle acid or a salt thereof, glycerol, and R'—C(O)OH or a salt thereof;

R' is $C_1$-$C_{20}$ aliphatic; and at least one hydrolysis product is a TCA cycle acid or a salt thereof.

In some embodiments, at least one hydrolysis product is a TCA cycle acid or a salt thereof, at least one hydrolysis product is glycerol, and at least one hydryolysis product is R'—C(O)OH or a salt thereof. In some embodiments, R'—C(O)OH is a linear fatty acid with even number of carbon atoms.

In some embodiments, a provided compound has the structure of formula I-a or a pharmaceutically acceptable salt thereof:

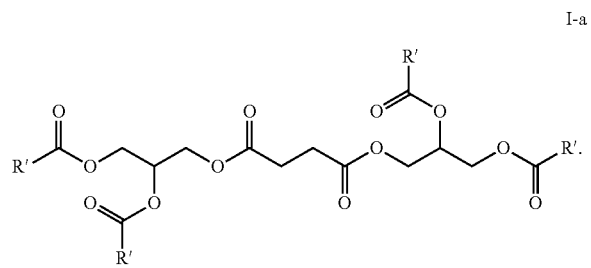

I-a

In some embodiments, a provided compound has the structure of $U_1$-$[U_2$-$U_3]_n$-$U_4$-$U_5$, wherein:

$U^1$ is

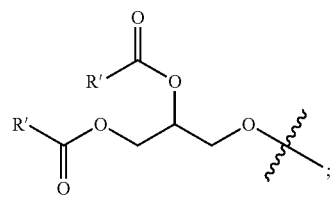

each of $U^2$ and $U^4$ is independently —C(O)-$L^1$-C(O)—, wherein $L^1$ is a bivalent $C_1$-$C_{20}$ aliphatic group wherein one or more —$CH_2$— units are independently and optionally replaced with —O—, —C(O)—, or —C(O)O—;

each $U^3$ is independently

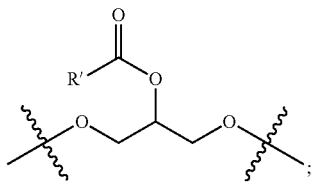

n is 0-20;
$U^5$ is

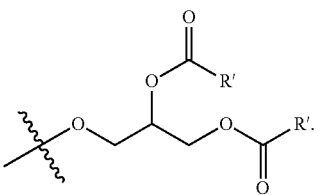

In some embodiments, n is 0-5. In some embodiments, n is 0. In some embodiments, n is 1. In some embodiments, n is 2. In some embodiments, n is 3. In some embodiments, n is 4. In some embodiments, n is 5.

In some embodiments, the present disclosure provides a compound comprising one or more TCA cycle acid moieties, one or more carboxylic acid moieties, and one or more diol or polyol moieties. In some embodiments, a TCA cycle acid moiety has the structure of R—C(O)O—, with R—C(O)OH being the corresponding TCA cycle acid. In some embodiments, a carboxylic acid moiety has the structure of R'—C(O)O— or R'—C(O)—, with R'—C(O)OH being the corresponding carboxylic acid. In some embodiments, the one or more TCA cycle acid moieties, the one or more carboxylic acid moieties, and the one or more diol or polyol moieties are connected via ester groups. In some embodiments, there is no free —OH in a provided compound. In some embodiments, there is no free —C(O)OH in a provided compound. In some embodiments, there is no free —OH and no free —C(O)OH in a provided compound. In some embodiments, the present disclosure provides a compound comprising one or more TCA cycle acid moieties, one or more carboxylic acid moieties having the structure of R'—C(O)O— or R'—C(O)—, and one or more $C_{2-10}$ diol or polyol moieties, wherein the one or more TCA cycle acid moieties, the one or more carboxylic acid moieties, and the one or more diol or polyol moieties are connected via ester groups.

In some embodiments, the present disclosure provides a compound, formed by condensation of:

(a) one or more TCA cycle acids;
(b) one or more ketone bodies; and
(c) optionally one or more backbone moiety compounds.

In some embodiments, a backbone moiety compound is a $C_{2-10}$ hydrocarbon compound which is independently substituted with two or more groups selected from hydroxyl, amino, and carboxyl groups. In some embodiments, a backbone moiety compound is a $C_{2-10}$ hydrocarbon compound which is independently substituted with two or more groups selected from hydroxyl and amino groups. In some embodiments, a backbone moiety compound is a $C_2$-10 polyol. In some embodiments, a backbone moiety compound is glycerol.

In some embodiments, the present disclosure provides a compound produced by a method comprising steps of reacting one or more $C_{2-10}$ diol or polyol, one or more TCA cycle acids and one or more carboxylic acids having the structure of R'—C(O)OH, so that one or more ester groups are formed linking a polyol, a TCA cycle acid, and a carboxylic. In some embodiments, a plurality of TCA cycle acids are used. In some embodiments, one TCA cycle acid is used. In some embodiments, a plurality of R—C(O)OH are used. In some embodiments, one R—C(O)OH is used. In some embodiments, two or more diols and/or polyols are used. In some embodiments, one diol is used. In some embodiments, one polyol is used. In some embodiments, a polyol is glycerol.

In some embodiments, the present disclosure provides a compound comprising one or more backbone moieties and optionally one or more linker moieties, wherein:

each backbone moiety is independently a $C_{2-10}$ hydrocarbon moiety substituted with two or more groups selected from hydroxyl, amino and carboxyl groups;

each backbone moiety is optionally substituted with one or more TCA cycle acid moieties, carboxylic acid moieties having the structure of R'—C(O)O— or R'—C(O)—, or combinations thereof, so that one or more of the groups selected from hydroxyl, amino and carboxyl groups are converted into the corresponding ester, amide or anhydride groups;

each linker moiety is independently a $C_{2-10}$ hydrocarbon moiety substituted with two or more carboxyl groups, and links two or more backbone moieties; and wherein the compound comprises at least one TCA cycle acid moiety and at least one carboxylic acid moiety.

In some embodiments, the present disclosure provides compositions which comprises one or more TCA cycle acid moieties, and one or more carboxylic moieties having the structure of R'—C(O)O— or R'—C(O)—, wherein each TCA cycle acid moiety is independently a TCA cycle acid or a salt thereof, or a structural unit which, upon hydrolysis of the composition, is converted into a TCA cycle acid or a salt thereof.

In some embodiments, a provided composition comprises a predetermined level of a first compound selected from a first group consisting of TCA cycle acids and salts, amides, esters, ketals, and anhydrides thereof; and a second compound selected from R'—C(O)OH and salts, amides, esters, ketals, and anhydrides thereof.

In some embodiments, the present disclosure provides a composition, which when optionally fully hydrolyzed, provides a predetermined level of (a) a TCA cycle acid or a salt thereof; and (b) R'—C(O)OH or a salt thereof.

In some embodiments, a provided composition comprises a provided compound. e.g., a provided combination compound. In some embodiments, a provided composition is a pharmaceutical composition comprises an effective amount of a TCA cycle acid moiety, and an effective amount of a R'—C(O)O— moiety, and a pharmaceutically acceptable carrier.

In some embodiments, provided compounds and/or compositions comprise a predetermined level of a TCA cycle acid moiety and a R'—C(O)O— moiety. In some embodiments, all TCA cycle acid moieties and R'—C(O)O— moieties have predetermined levels. In some embodiments, a predetermined level is a predetermined amount. In some embodiments, a provided level is a predetermined ratio. In some embodiments, the ratio between a TCA cycle acid moiety and another carboxylic acid moiety, or between the total of all TCA cycle acid moieties and the total of all other carboxylic acid moieties, is between 100:1 and 1:100.

In some embodiments, each of $R^1$, $R^2$ and $R^3$ is independently —B, —S, or —S'—B'; B is —OC(O)CH$_2$CH(OH)CH$_3$; S is —OC(O)CH$_2$CH$_2$C(O)OH; S' is —OC(O)CH$_2$CH$_2$C(O)O—; B' is —CH(CH$_3$)CH$_2$C(O)OH; and wherein when one of $R^1$, $R^2$ and $R^3$ is B or S, at least two of $R^1$, $R^2$ and $R^3$ are different.

In some embodiments, each of $R^1$, $R^2$ and $R^3$ is independently —OC(O)R, wherein —OC(O)R is a moiety whose corresponding acid R—C(O)OH is a TCA cycle acid or beta-hydroxybutyric acid; at least one of $R^1$, $R^2$ and $R^3$ is —OC(O)R, wherein —OC(O)R is a moiety whose corresponding acid R—C(O)OH is a TCA cycle acid; and at least one of $R^1$, $R^2$ and $R^3$ is —OC(O)R, wherein —OC(O)R is a moiety whose corresponding acid R—C(O)OH is beta-hydroxybutyric acid. In some embodiments, each of $R^1$, $R^2$ and $R^3$ is independently —OC(O)R, wherein each —OC(O)R is independently a moiety whose corresponding acid R—C(O)OH is succinic acid or beta-hydroxybutyric acid.

In some embodiments, each of $R^1$, $R^2$ and $R^3$ is independently —OC(O)-L$^1$-C(O)—O-L$^2$-C(O)OH, wherein each —OC(O)-L$^1$-C(O)— is independently a moiety whose corresponding acid HOC(O)-L$^1$-C(O)OH is a diacid or triacid of the TCA cycle, and each —O-L$^2$-C(O)OH is independently a moiety whose corresponding hydroxyacid HO-L$^2$-C(O)OH is beta-hydroxybutyric acid.

In some embodiments, a provided compound has the structure of $U_1$-[$U_2$-$U_3$]$_n$-$U_4$-$U_5$, wherein:

$U^1$ is

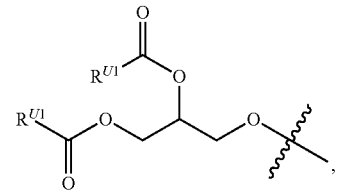

wherein each $R^{U1}$—C(O)O— is independently a moiety whose corresponding acid $R^{U1}$—C(O)OH is a TCA cycle acid, beta-hydroxybutyric acid or acetoacetic acid;

each of $U^2$ and $U^4$ is independently —C(O)-L$^1$-C(O)—, wherein each —C(O)-L$^1$-C(O)— is independently a moiety whose corresponding acid HOC(O)-L$^1$-C(O)OH is a TCA cycle diacid or triacid;

each $U^3$ is independently

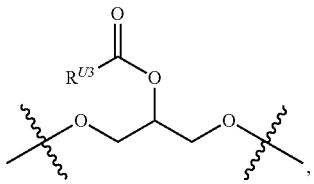

wherein each $R^{U3}$—C(O)O— is independently a moiety whose corresponding acid $R^{U3}$—C(O)OH is a TCA cycle acid, beta-hydroxybutyric acid or acetoacetic acid;

n is 0-100;

$U^5$ is

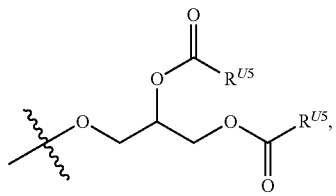

wherein each $R^{U5}$ is independently a moiety whose corresponding acid $R^{U5}$—C(O)OH is a TCA cycle acid, beta-hydroxybutyric acid or acetoacetic acid; and wherein at least one of $R^{U1}$—C(O)O—, $R^{U3}$—C(O)O—, and $R^{U5}$—C(O)O— is a moiety whose corresponding acid is beta-hydroxybutyric acid or acetoacetic acid.

In some embodiments, a provided compound has the structure of $U^1$-[$U^2$-$U^3$]$_n$-$U^4$-$U^5$, wherein:

$U^1$ is

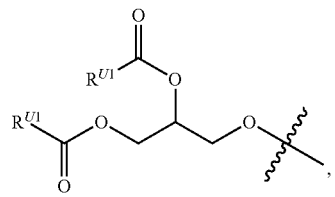

wherein each $R^{U1}$—C(O)O— is independently a moiety whose corresponding acid $R^{U1}$—C(O)OH is a TCA cycle acid or beta-hydroxybutyric acid;

each of $U^2$ and $U^4$ is independently —C(O)-L$^1$-C(O)—, wherein each —C(O)-L$^1$-C(O)— is independently a moiety whose corresponding acid HOC(O)-L$^1$-C(O)OH is a TCA cycle diacid or triacid;

each $U^3$ is independently

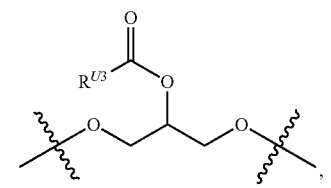

wherein each $R^{U3}$—C(O)O— is independently a moiety whose corresponding acid $R^{U3}$—C(O)OH is a TCA cycle acid or beta-hydroxybutyric acid;

n is 0-100;

$U^5$ is

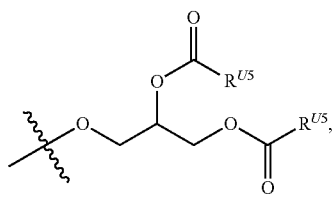

wherein each $R^{U5}$ is independently a moiety whose corresponding acid $R^{U5}$—C(O)OH is a TCA cycle acid or beta-hydroxybutyric acid; and wherein at least one of $R^{U1}$—C(O)O—, $R^{U3}$—C(O)O—, and $R^{U5}$—C(O)O— is a moiety whose corresponding acid is beta-hydroxybutyric acid.

In some embodiments, the present disclosure provides a compound, formed by condensation of:

(a) one or more TCA cycle acids;

(b) one or more ketone bodies; and (c) optionally one or more backbone moiety compounds.

In some embodiments, a backbone moiety compound is a $C_{2-10}$ hydrocarbon compound which is independently substituted with two or more groups selected from hydroxyl, amino, and carboxyl groups. In some embodiments, a backbone moiety compound is a $C_{2-10}$ hydrocarbon compound which is independently substituted with two or more groups selected from hydroxyl and amino groups. In some embodiments, a backbone moiety compound is a $C_{2-10}$ polyol. In some embodiments, a backbone moiety compound is glycerol.

In some embodiments, the present disclosure provides a compound whose structure comprises a moiety of formula II:

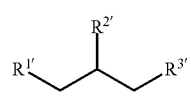

II wherein:

each of $R^{1'}$, $R^{2'}$ and $R^{3'}$ is independently —B, —S, —S'—B', —S', or —B", B is —OC(O)CH$_2$CH(OH)CH$_3$;

S is —OC(O)CH$_2$CH$_2$C(O)OH;

S' is —OC(O)CH$_2$CH$_2$C(O)O—;

B' is —CH(CH$_3$)CH$_2$C(O)OH;

B" is —OC(O)CH$_2$CH(CH$_3$)O—; and wherein when each ester bond in the compound is hydrolyzed, one of the hydrolysis product is succinic acid and one is beta-hydroxybutyric acid.

In some embodiments, the present disclosure provides a compound produced by a method comprising steps of reacting a polyol with a TCA cycle acid and a ketone body, so that one or more ester, and optionally ketal, groups are formed linking the polyol, TCA cycle acid, and ketone body. In some embodiments, a plurality of TCA cycle acids are used. In some embodiments, a plurality of ketone bodies are used. In some embodiments, a polyol is glycerol.

In some embodiments, the present disclosure provides a compound comprising one or more backbone moieties and optionally one or more linker moieties, wherein:

each backbone moiety is independently a $C_{2-10}$ hydrocarbon moiety substituted with two or more groups selected from hydroxyl, amino and carboxyl groups;

each backbone moiety is optionally substituted with one or more TCA cycle acid moieties, ketone body moieties or combinations thereof, so that one or more of the groups selected from hydroxyl, amino and carboxyl groups are converted into the corresponding ester, amide or anhydride groups;

each linker moiety is independently a $C_{2-10}$ hydrocarbon moiety substituted with two or more carboxyl groups, and links two or more backbone moieties; and wherein the compound comprises at least one TCA cycle acid moiety and at least one ketone body moiety.

In some embodiments, the present disclosure provides compositions which comprises one or more TCA cycle acid moieties, and one or more ketone body moieties, wherein each TCA cycle acid moiety is independently a TCA cycle acid or a salt thereof, or a structural unit which, upon hydrolysis of the composition, is converted into a TCA cycle acid or a salt thereof; and each ketone body moiety is independently a ketone body or a salt thereof, or a structural unit which, upon hydrolysis of the composition, is converted into a ketone body.

In some embodiments, a provided composition comprises a predetermined level of a first compound selected from a first group consisting of TCA cycle acids and salts, amides, esters, ketals, and anhydrides thereof; and a second compound selected from a second group consisting of ketone bodies and salts, amides, esters, ketals, and anhydrides thereof.

In some embodiments, the present disclosure provides a composition, which when optionally fully hydrolyzed, provides a predetermined level of (a) a TCA cycle acid or salt thereof; and (b) a ketone body or salt thereof.

In some embodiments, a provided composition comprises a provided compound. e.g., a provided combination compound. In some embodiments, a provided composition is a pharmaceutical composition comprises an effective amount of a TCA cycle acid moiety, and an effective amount of a ketone body moiety, and a pharmaceutically acceptable carrier.

In some embodiments, provided compounds and/or compositions comprise a predetermined level of a TCA cycle acid moiety and a ketone body moiety. In some embodiments, all TCA cycle acid moieties and ketone body moieties have predetermined levels. In some embodiments, a predetermined level is a predetermined amount. In some embodiments, a provided level is a predetermined ratio. In some embodiments, the ratio between a TCA cycle acid moiety and a ketone body moiety, or between the total of all TCA cycle acid moieties and the total of all ketone body moieties, is between 100:1 and 1:100.

Various diseases, disorders, and/or conditions may be related to abnormal metabolism, and can be treated and/or benefit from provided technologies. In some embodiments, the present disclosure provides methods comprising administering to a subject suffering from or susceptible to a disease, disorder or condition a pharmaceutically effective amount of a provided compound or composition. In some embodiments, a disease, disorder or condition is related to abnormal metabolism. In some embodiments, a disease, disorder or condition is an energetic disorder. In some embodiments, a disease, disorder or condition is a neurologic disease. In some embodiments, a disease, disorder or condition is a cancer. In some embodiments, a disease, disorder or condition is a pain or fatigue disease. In some embodiments, a disease, disorder or condition is muscular dystrophies. In some embodiments, a disease, disorder or condition is a mitochondrial myopathy. In some embodiments, a disease, disorder or condition is a mitochondrial associated disease.

DETAILED DESCRIPTION OF CERTAIN EMBODIMENTS

1. Definitions

A. Chemical Definitions

Figure 1:
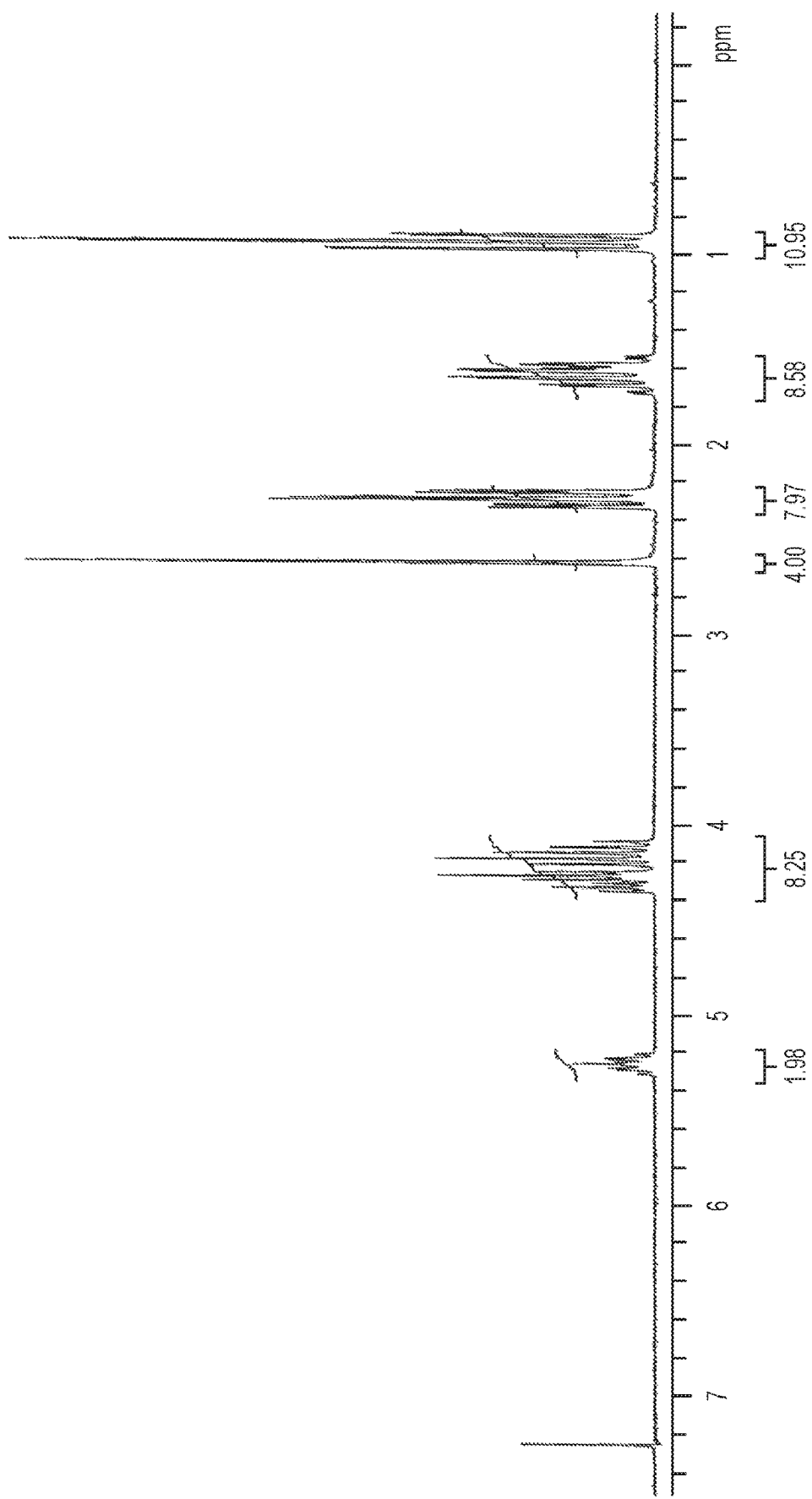
FIG. 1. Example NMR of compound I-29.

As used herein, the following definitions shall apply unless otherwise indicated. For purposes of this disclosure, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

Aliphatic: As used herein, "aliphatic" means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or polycyclic hydrocarbon that is completely saturated or that contains one or more units of unsaturation that has a single point of attachment to the rest of the molecule. Unless otherwise specified, aliphatic groups contain 1-100 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, a cycloalkyl ring has from about 3-10 carbon atoms in their ring structure where such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Alkenyl: As used herein, the term "alkenyl" refers to an alkyl group, as defined herein, having one or more double bonds.

Alkynyl: As used herein, the term "alkynyl" refers to an alkyl group, as defined herein, having one or more triple bonds.

Protecting Group: The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates, allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other tri-alkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Substitution: As described herein, compounds of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents include halogen; —(CH$_2$)$_{0-4}$R$^\circ$; —(CH$_2$)$_{0-4}$R$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ$$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ$$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$C(O)NR$^\circ$$_2$; —C(S)NR$^\circ$$_2$; —C(S)SR$^\circ$; —SC(S)SR$^\circ$, —(CH$_2$)$_{0-4}$OC(O)NR$^\circ$$_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ$$_2$; —(CH$_2$)$_{0-4}$S(O)R$^\circ$; —N(R$^\circ$)S(O)$_2$NR$^\circ$$_2$; —N(R$^\circ$)S(O)$_2$R$^\circ$; —N(OR$^\circ$)R$^\circ$; —C(NH)NR$^\circ$$_2$; —P(O)$_2$R$^\circ$; —P(O)R$^\circ$$_2$; —OP(O)R$^\circ$$_2$; —OP(O)(OR$^\circ$)$_2$; —SiR$^\circ$$_3$; —OSiR$^\circ$$_3$; —(C$_{1-4}$ straight or branched alkylene)O—N(R$^\circ$)$_2$; or —(C$_{1-4}$ straight or branched alkylene)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)O_2R^\bullet$, -(halo$R^\bullet$), —$(CH_2)_{0-2}OH$, —$(CH_2)_{0-2}OR^\bullet$, —$(CH_2)_{0-2}CH(OR^\bullet)_2$; —O(halo$R^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)$C(O)OR^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-}$aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —$R^\bullet$, -(halo$R^\bullet$), —OH, —$OR^\bullet$, —O(halo$R^\bullet$), —CN, —C(O)OH, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

In some embodiments, suitable substituents on a substitutable nitrogen include —$R^\dagger$, —$NR^\dagger_2$, —$C(O)R^\dagger$, —C(O)$OR^\dagger$, —$C(O)C(O)R^\dagger$, —$C(O)CH_2C(O)R^\dagger$, —$S(O)_2R^\dagger$, —$S(O)_2NR^\dagger_2$, —$C(S)NR^\dagger_2$, —$C(NH)NR^\dagger_2$, or —$N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —$R^\bullet$, -(halo$R^\bullet$), —OH, —$OR^\bullet$, —O(halo$R^\bullet$), —CN, —C(O)OH, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

B. Other Definitions

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, topical, etc. . . . In some particular embodiments, administration may be bronchial (e.g., by bronchial instillation), buccal, dermal (which may be or comprise, for example, one or more of topical to the dermis, intradermal, interdermal, transdermal, etc), enteral, intra-arterial, intradermal, intragastric, intramedullary, intramuscular, intranasal, intraperitoneal, intrathecal, intravenous, intraventricular, within a specific organ (e.g. intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Agent: In general, the term "agent" may be used to refer to a compound or entity of any chemical class including, for example, a polypeptide, nucleic acid, saccharide, lipid, small molecule, metal, or combination thereof. Those of ordinary skill in the art will appreciate that, in general, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer. In some embodiments, the term may refer to a compound or entity that lacks or is substantially free of any polymeric moiety Agonist: Those skilled in the art will appreciate that the term "agonist" may be used to refer to an agent condition, or event whose presence, level, degree, type, or form correlates with increased level or activity of another agent (i.e., the agonized agent). In general, an agonist may be or include an agent of any chemical class including, for example, small molecules, polypeptides, nucleic acids, carbohydrates, lipids, metals, and/or any other entity that shows the relevant activating activity. In some embodiments, an agonist may be direct (in which case it exerts its influence directly upon its target); in some embodiments, an agonist may be indirect (in which case it exerts its influence by other than binding to its target; e.g., by interacting with a regulator of the target, so that level or activity of the target is altered).

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, a genetically-engineered animal, and/or a clone.

Combination therapy: As will be understood by those skilled in the art, the term "combination therapy" refers to those situations in which a subject is simultaneously exposed to two or more therapeutic regimens (e.g., two or more therapeutic agents). In some embodiments, two or more agents or may be administered simultaneously; in some embodiments, such agents may be administered sequentially; in some embodiments, such agents are administered in overlapping dosing regimens. In some embodiments, "administration" of combination therapy may involve administration of one or more agents to a subject receiving the other agents in the combination. For clarity, combination therapy does not require that individual agents be administered together in a single composition (or even necessarily at the same time), although in some embodiments, two or more active agents, entities, or moieties may be administered together in a combination composition, or even in a combination compound (e.g., as part of a single chemical complex or covalent entity).

Comparable: As used herein, the term "comparable" refers to two or more agents, entities, situations, sets of conditions, etc., that may not be identical to one another but that are sufficiently similar to permit comparison there between so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Composition: Those skilled in the art will appreciate that the term "composition" may be used to refer to a discrete physical entity that comprises one or more specified components. In general, unless otherwise specified, a composition may be of any form—e.g., gas, gel, liquid, solid, etc.

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer o a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen).

Intraperitoneal: The phrases "intraperitoneal administration" and "administered intraperitoneally" as used herein have their art-understood meaning referring to administration of a compound or composition into the peritoneum of a subject.

Ketone bodies: Ketogenesis is a widely known process in the art which produces a group of ketone bodies from fatty acids. In some embodiments, a ketone body is acetoacetic acid, acetone or D-beta-hydroxybutyric acid. In some embodiments, a ketone body is acetoacetic acid. In some embodiments, a ketone body is acetone. In some embodiments, a ketone body is D-beta-hydroxybutyric acid. In some embodiments, ketogenesis is an important energy source for certain organs, e.g., brain, under certain circumstances, e.g., fasting. An exemplary description of ketogenesis is depicted below.

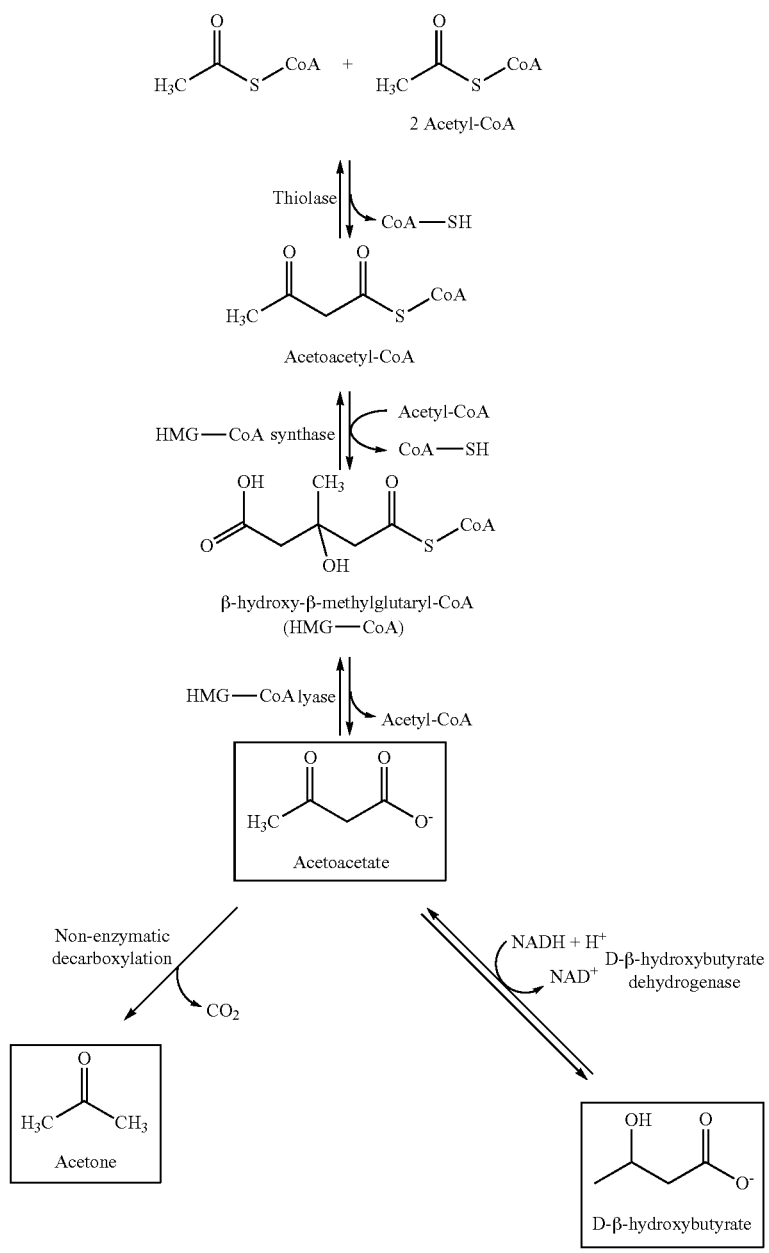

Moiety: Those skilled in the art will appreciate that a "moiety" is a defined chemical group or entity with a particular structure and/or or activity, as described herein. In some embodiments, a carboxylic acid moiety and an alcohol moiety (e.g., a diol, polyol, etc.) forms an ester group comprising —C(O)O—. In some embodiments, when a compound is fully hydrolyzed (for example, when all ester groups are hydrolyzed to the corresponding —C(O)OH and —OH groups), a carboxylic acid moiety is converted to its corresponding carboxylic acid (e.g., from R'—C(O)— to R'—C(O)OH), and an alcohol is converted to its corresponding alcohol (e.g., from a glycerol triester (—O—CH$_2$—CH (O—)—CH$_2$—(O)— to glycerol).

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salt include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, a pharmaceutically acceptable salt is an alkali salt. In some embodiments, a pharmaceutically acceptable salt is a sodium salt. In some embodiments, a pharmaceutically acceptable salt is an alkaline earth metal salt. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Subject: As used herein, the term "subject" or "test subject" refers to any organism to which a provided compound or composition is administered in accordance with the present disclosure e.g., for experimental, diagnostic, prophylactic, and/or therapeutic purposes. Typical subjects include animals (e.g., mammals such as mice, rats, rabbits, non-human primates, and humans; insects; worms; etc.) and plants. In some embodiments, a subject may be suffering from, and/or susceptible to a disease, disorder, and/or condition.

Predetermined: By predetermined is meant deliberately selected, for example as opposed to randomly occurring or achieved.

Suffering from: An individual who is "suffering from" a disease, disorder, and/or condition has been diagnosed with and/or displays one or more symptoms of a disease, disorder, and/or condition.

Susceptible to: An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Systemic: The phrases "systemic administration," "administered systemically," "peripheral administration," and "administered peripherally" as used herein have their art-understood meaning referring to administration of a compound or composition such that it enters the recipient's system.

Tautomeric forms: The phrase "tautomeric forms," as used herein, is used to describe different isomeric forms of organic compounds that are capable of facile interconversion. Tautomers may be characterized by the formal migration of a hydrogen atom or proton, accompanied by a switch of a single bond and adjacent double bond. In some embodiments, tautomers may result from prototropic tautomerism (i.e., the relocation of a proton). In some embodiments, tautomers may result from valence tautomerism (i.e., the rapid reorganization of bonding electrons). All such tautomeric forms are intended to be included within the scope of the present disclosure. In some embodiments, tautomeric forms of a compound exist in mobile equilibrium with each other, so that attempts to prepare the separate substances results in the formation of a mixture. In some embodiments, tautomeric forms of a compound are separable and isolatable compounds. In some embodiments of the disclosure, chemical compositions may be provided that are or include pure preparations of a single tautomeric form of a compound. In some embodiments, chemical compositions may be provided as mixtures of two or more tautomeric forms of a compound. In certain embodiments, such mixtures contain equal amounts of different tautomeric forms; in certain embodiments, such mixtures contain different amounts of at least two different tautomeric forms of a compound. In some embodiments of the disclosure, chemical compositions may contain all tautomeric forms of a compound. In some embodiments of the disclosure, chemical compositions may contain less than all tautomeric forms of a compound. In some embodiments of the disclosure, chemical compositions may contain one or more tautomeric forms of a compound in amounts that vary over time as a result of interconversion. In some embodiments of the disclosure, the tautomerism is keto-enol tautomerism. One of skill in the chemical arts would recognize that a keto-enol tautomer can be "trapped" (i.e., chemically modified such that it remains in the "enol" form) using any suitable reagent known in the chemical arts in to provide an enol derivative that may subsequently be isolated using one or more suitable techniques known in the art. Unless otherwise indicated, the present disclosure encompasses all tautomeric forms of relevant compounds, whether in pure form or in admixture with one another.

TCA Cycle: Tricarboxylic acid (TCA) cycle, also known the citric acid cycle or the Krebs cycle, comprises a series of chemical reactions to generate energy and provide other biological functions, e.g., producing amino acid precursors, synthesizing reducing agent, etc. The TCA cycle is widely known and described in the art, see, for example, Alberts et al., Molecular Biology of the Cell, Garland Science, 6 ed., 2014. Exemplary reactions, intermediates, and enzymes are set forth in the scheme below. In some embodiments, a TCA cycle acid is an acid in the scheme depicted below. In some embodiments, a TCA cycle acid is selected from oxaloacetic acid, citric acid, cis-aconitic acid, D-isocitric acid, alpha-ketoglutaric acid, succinic acid, fumaric acid and malic acid. In some embodiments, a TCA cycle acid is selected from pyruvic acid, oxaloacetic acid, citric acid, cis-aconitic acid, D-isocitric acid, alpha-ketoglutaric acid, succinic acid, fumaric acid and malic acid.

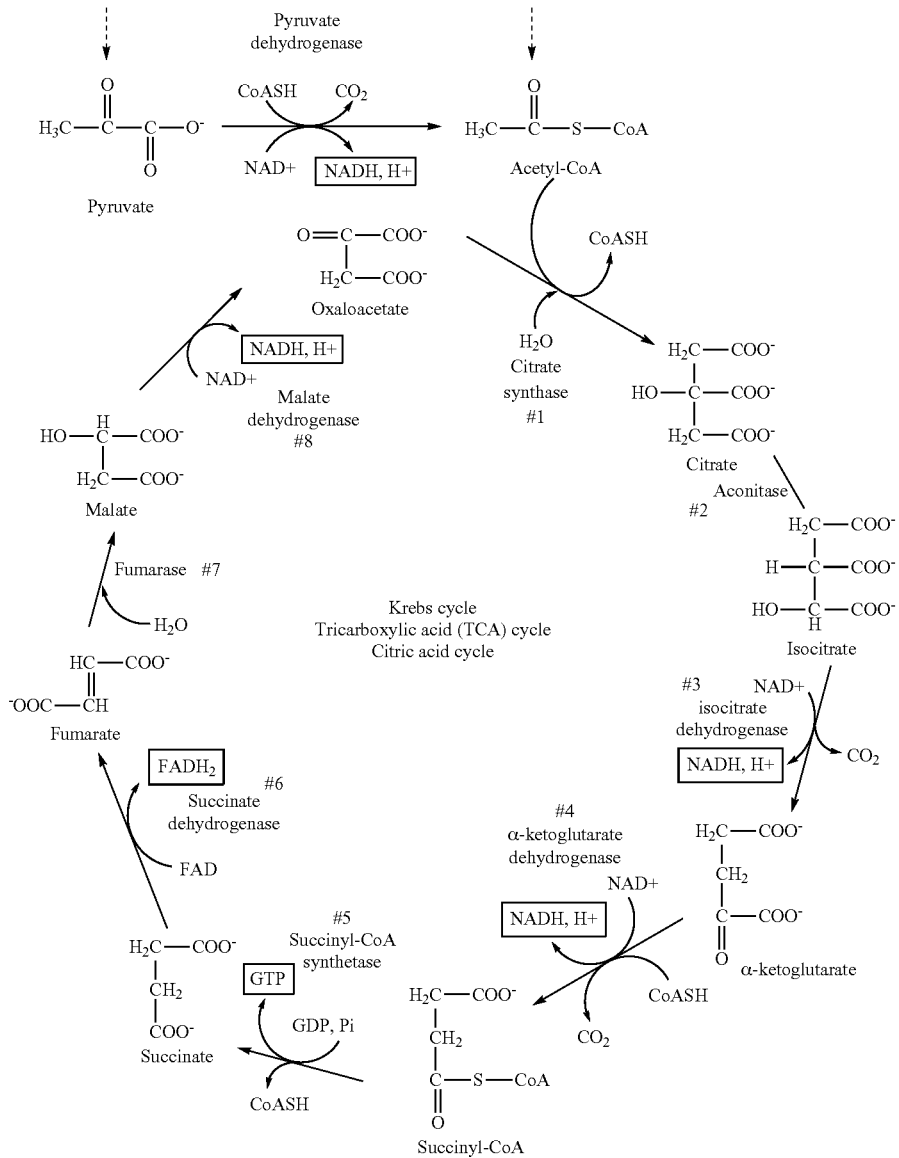

Therapeutic agent: As used herein, the phrase "therapeutic agent" refers to an agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

2. Detailed Description of Certain Embodiments

In some embodiments, the present disclosure recognizes that combination therapy, e.g., combinations of TCA cycle intermediates (e.g., TCA cycle acids) and carboxylic acids having the structure of R'—C(O)OH (e.g., those that can be metabolized to provide one or more ketone bodies, acetyl-CoA and/or propionyl-CoA), are particularly effectively for treating abnormal metabolism and related diseases. Exemplary provided technologies, e.g., compounds, compositions, methods, etc. are described in the present disclosure.

In some embodiments, the present disclosure recognizes that combination therapy, e.g., combinations of TCA cycle intermediates (e.g., TCA cycle acids) and ketone bodies, are particularly effectively for treating abnormal metabolism and related diseases. Exemplary provided technologies, e.g., compounds, compositions, methods, etc. are described below.

Combination Therapy

In some embodiments, the present disclosure provides compounds and/or compositions for combination therapy, which provides both a TCA cycle intermediate and a carboxylic acid having the structure of R'—C(O)OH. In some embodiments, the carboxylic acid can be metabolized to provide one or more ketone bodies, acetyl-CoA and/or propionyl-CoA. In some embodiments, the carboxylic acid can be metabolized to provide one or more ketone bodies. In some embodiments, the carboxylic acid can be metabolized to provide acetyl-CoA (e.g., through beta-oxidation of even-chain fatty acids such as butyric acid, caprylic acid, etc.). In some embodiments, the carboxylic acid can be metabolized to provide acetyl-CoA and propionyl-CoA(e.g., through beta-oxidation of odd-chain fatty acids such as heptanoic acid).

In some embodiments, the present disclosure provides compounds and/or compositions for combination therapy, which provides both a TCA cycle intermediate and a ketone body.

In some embodiments, a TCA cycle intermediate, e.g., a TCA cycle acid, may be generated at a low level due to abnormal metabolism such as lack of starting material, malfunction of enzymes, etc., and a provided technology increases level of such an intermediate. Similarly, in some embodiments, a provided technology increases level of a ketone body by providing a ketonde body, a ketone body moiety, and/or a carboxylic acid, e.g., that has the structure of R'—C(O)OH and can be metabolized to provide a ketone body. In some embodiments, levels of both a TCA cycle intermediate and a ketone body are increased by a provided technology. In some embodiments, a provided technology comprises one or more TCA cycle intermediates and one or more ketone bodies. In some embodiments, a provided technology provides two or more ketone bodies. In some embodiments, a provided technology comprises one or more TCA cycle intermediates and one or more carboxylic acids, e.g., those that can be metabolized to provide one or more ketone bodies. In some embodiments, a provided technology provides two or more TCA cycle intermediates. In some embodiments, a provided technology provides two or more carboxylic acids that can be metabolized to provide one or more ketone bodies. In some embodiments, levels of two or more TCA cycle intermediates are adjusted by a provided technology. In some embodiments, levels of two or more ketone bodies are adjusted by a provided technology. In some embodiments, levels of a TCA cycle intermediate and a ketone body are adjusted simultaneously. In some embodiments, levels of more than one TCA cycle intermediate and/or more than one ketone body are adjusted simultaneously. In some embodiments, a provided technology increases level of acetyl-CoA by providing a carboxylic acid, e.g., that has the structure of R'—C(O)OH and can be metabolized to provide acetyl-CoA. In some embodiments, increased acetyl-CoA enhances and/or provides TCA cycle replenishment in addition to provided TCA cycle acids, e.g., from TCA cycle acid moieties within provided combination compounds. In some embodiments, a provided technology increases level of propionyl-CoA by providing a carboxylic acid, e.g., that has the structure of R'—C(O)OH and can be metabolized to provide propionyl-CoA.

In some embodiments, a provided technology is useful for providing energy to certain cells, tissues and/or organs. In some embodiments, an organ is brain. In some embodiments, an organ is heart.

In some embodiments, a TCA cycle intermediate is a TCA cycle acid. In some embodiments, a TCA cycle acid is selected from succinic acid, fumaric acid, malic acid, oxaloacetic acid, citric acid, cis-aconitic acid, D-isocitric acid, alpha-ketoglutaric acid, and succinyl-CoA. In some embodiments, a TCA cycle acid is selected from succinic acid, fumaric acid, malic acid, oxaloacetic acid, citric acid, cis-aconitic acid, D-isocitric acid, and alpha-ketoglutaric acid. In some embodiments, a TCA cycle acid is succinic acid. In some embodiments, a TCA cycle acid is fumaric acid. In some embodiments, a TCA cycle acid is malic acid. In some embodiments, a TCA cycle acid is oxaloacetic acid. In some embodiments, a TCA cycle acid is citric acid. In some embodiments, a TCA cycle acid is cis-aconitic acid. In some embodiments, a TCA cycle acid is D-isocitric acid. In some embodiments, a TCA cycle acid is alpha-ketoglutaric acid. In some embodiments, a TCA cycle acid is succinyl-CoA.

In some embodiments, a TCA cycle acid is a diacid or triacid. In some embodiments, a TCA cycle acid is a diacid. In some embodiments, a TCA cycle acid is a triacid. In some embodiments, a TCA cycle diacid or triacid is selected from succinic acid, fumaric acid, malic acid, oxaloacetic acid, citric acid, cis-aconitic acid, D-isocitric acid, and alpha-ketoglutaric acid.

In some embodiments, a TCA cycle diacid is selected from succinic acid, fumaric acid, malic acid, oxaloacetic acid and alpha-ketoglutaric acid. In some embodiments, a TCA cycle diacid is succinic acid. In some embodiments, a TCA cycle diacid is fumaric acid. In some embodiments, a TCA cycle diacid is malic acid. In some embodiments, a TCA cycle diacid is oxaloacetic acid. In some embodiments, a TCA cycle diacid is alpha-ketoglutaric acid.

In some embodiments, a TCA cycle triacid is selected from citric acid, cis-aconitic acid, and D-isocitric acid. In some embodiments, a TCA cycle triacid is citric acid. In some embodiments, a TCA cycle triacid is cis-aconitic acid. In some embodiments, a TCA cycle triacid is D-isocitric acid.

In some embodiments, a ketone body is acetoacetic acid. In some embodiments, a ketone body is acetone. In some embodiments, a ketone body is D-beta-hydroxybutyric acid. In some embodiments, a ketone body is acetoacetate or D-beta-hydroxybutyric acid.

In some embodiments, a acid has the structure of R'—C(O)OH, and its corresponding carboxylic acid moiety has the structure of R'—C(O)O—. In some embodiments, an acid has the structure of R'—C(O)OH, and its corresponding carboxylic acid moiety has the structure of R'—C(O)—. As appreciated by a person having ordinary skill in the art, for a given carboxylic acid derivative such as an ester having the structure of R'—C(O)O—R, in some embodiments, a carboxylic acid moiety can be considered to have the structure of R'—C(O)—, with the alcohol moiety having the structure of R—O—; in some embodiments, a carboxylic acid moiety can be considered to have the structure of R'—C(O)O—, with the alcohol moiety having the structure of R—.

In some embodiments, a carboxylic acid is not a TCA cycle acid or a ketone body. In some embodiments, a carboxylic acid is not a TCA cycle acid. In some embodiments, a carboxylic acid is not a ketone body. In some embodiments, R'—C(O)OH is not a TCA cycle acid or a ketone body. In some embodiments, R'—C(O)OH is not a TCA cycle acid. In some embodiments, R'—C(O)OH is not a ketone body.

In some embodiments, a provided combination comprises or is a "physical" combination wherein the combination comprises two compounds, one of which is a TCA cycle acid or a derivative thereof, and the other is a ketone body, acetyl-CoA, or propionyl-CoA, or a derivative thereof, or a carboxylic acid that can be metabolized to provide a ketone body, acetyl-CoA, propionyl-CoA or a derivative thereof. In some embodiments, a provided combination comprises or is a "physical" combination wherein the combination comprises two compounds, one of which is a TCA cycle acid or a derivative thereof, and the other is a ketone body or a derivative thereof. In some embodiments, the other is a ketone body or a derivative thereof, or a carboxylic acid that can be metabolized to provide a ketone body or a derivative thereof. In some embodiments, the other is acetyl-CoA or propionyl-CoA, or a derivative thereof, or a carboxylic acid that can be metabolized to provide acetyl-CoA or propionyl-CoA, or a derivative thereof. In some embodiments, the other is acetyl-CoA or a derivative thereof, or a carboxylic acid that can be metabolized to provide acetyl-CoA. In some embodiments, the other is propionyl-CoA or a derivative thereof, or a carboxylic acid that can be metabolized to provide propionyl-CoA. In some embodiments, a combination is a physical combination. In some embodiments, a combination comprises a physical combination. Those skilled in the art will appreciate that a variety of suitable derivatives might be utilized in accordance with the present disclosure, such as derivatives of a hydroxyl, ketone, and/or carboxylic acid groups in a TCA cycle acid, a ketone body, and/or another carboxylic acid. In some embodiments, a derivative is a protected TCA cycle acid or ketone body, wherein one or more of its hydroxyl, ketone or carboxyl groups are optionally protected by protection groups. In some embodiments, a derivative is a protected TCA cycle acid or another carboxylic acid, wherein one or more of its hydroxyl, ketone or carboxyl groups are optionally protected by protection groups. In some embodiments, a derivative is a salt. In some embodiments, a derivative is a pharmaceutically acceptable salt. In some embodiments, a derivative is a carboxylic acid derivative, types of which are widely known in the art and which, upon hydrolysis, converts into a carboxyl group (e.g., an ester group to carboxyl group). In some embodiments, a derivative is an ester. In some embodiments, a derivative is an amide. In some embodiments, a derivative is a carbamate. In some embodiments, a derivative is an anhydride. In some embodiments, a derivative upon hydrolysis provides its corresponding TCA cycle acid or ketone body, and the other hydrolysis products are not toxic in that they do not cause toxicity that prevents the derivative from being administered at a pharmaceutically effective amount. In some embodiments, a derivative upon hydrolysis provides its corresponding TCA cycle acid or another carboxylic acid (e.g., R—C(O)OH which is not a TCA cycle acid and which can be metabolized to provide a ketone body, acetyl-CoA and/or propionyl-CoA), and the other hydrolysis products are not toxic in that they do not cause toxicity that prevents the derivative from being administered at a pharmaceutically effective amount.

In some embodiments, a combination comprises or is a "chemical combination", in that one or more TCA cycle intermediate moieties and one or more carboxylic acid (e.g., R'—C(O)OH which can be metabolized to provide one or more ketone bodies, acetyl-CoA and/or propionyl-CoA, and which, in some embodiments, is not a TCA cycle acid) moieties are connected, optionally through one or more backbone moieties, e.g., a $C_2$-$C_{10}$ diol or polyol (e.g., glycerol) moieties, to be provided in a single compound, e.g., a combination compound. In some embodiments, a combination comprises or is a "chemical combination", in that one or more TCA cycle intermediate moieties and one or more ketone body moieties are connected, optionally through one or more backbone moieties, e.g., glycerol moieties, to be provided in a single compound, e.g., a combination compound. In some embodiments, a combination comprises a chemical combination. In some embodiments, a combination is a chemical combination.

Those skilled in the art will appreciate that a variety of different backbone moieties might be utilized in accordance with the present disclosure. In some embodiments, a backbone moiety connects two or more groups selected from hydroxyl, ketone, alkenyl and carboxyl groups of a TCA cycle acid and/or a ketone body. In some embodiments, a backbone moiety connects two or more groups selected from hydroxyl, ketone, carboxyl groups of a TCA cycle acid and/or a ketone body. In some embodiments, a backbone moiety connects two or more carboxyl groups of a TCA cycle acid and/or a ketone body. In some embodiments, a backbone unit connects two or more carboxyl groups of a TCA cycle acid and/or a ketone body by forming ester groups. In some embodiments, a backbone moiety is a glycerol moiety, which connects to three acid moieties through three ester groups. In some embodiments, a backbone moiety connects two or more groups selected from hydroxyl, ketone, alkenyl and carboxyl groups of a TCA cycle acid and/or a carboxylic acid (e.g., R'—C(O)OH which can be metabolized to provide one or more ketone bodies, acetyl-CoA and/or propionyl-CoA, and which, in some embodiments, is not a TCA cycle acid). In some embodiments, a backbone moiety connects two or more groups selected from hydroxyl, ketone, carboxyl groups of a TCA cycle acid and/or a carboxylic acid (e.g., R'—C(O)OH which can be metabolized to provide one or more ketone bodies, acetyl-CoA and/or propionyl-CoA, and which, in some embodiments, is not a TCA cycle acid). In some embodiments, a backbone moiety connects two or more carboxyl groups of a TCA cycle acid and/or a carboxylic acid (e.g., R'—C(O)OH which can be metabolized to provide one or more ketone bodies, acetyl-CoA and/or propionyl-CoA, and which, in some embodiments, is not a TCA cycle acid). In some embodiments, a backbone unit connects two or more carboxyl groups of a TCA cycle acid and/or a carboxylic acid (e.g., R'—C(O)OH which can be metabolized to provide one or more ketone bodies, acetyl-CoA and/or propionyl-CoA, and which, in some embodiments, is not a TCA cycle acid) by forming ester groups. In some embodiments, a backbone moiety is a diol or polyol moiety, e.g., a $C_2$-$C_{10}$ diol or polyol moiety. In some embodiments, a backbone moiety is a glycerol moiety. In some embodiments, a backbone moiety is a glycerol moiety, which connects to three acid moieties through three ester groups.

In some embodiments, a backbone moiety is optionally substituted with a moiety selected from the group consisting of TCA cycle intermediate moieties, ketone body moieties, or a combination thereof. In some embodiments, a backbone moiety is optionally substituted with a moiety selected from the group consisting of TCA cycle intermediate moieties, ketone body moieties, and combinations thereof. In some embodiments, at least one backbone moiety comprises a TCA cycle acid moiety, and at least one backbone moiety comprises a ketone body moiety. In some embodiments, a backbone moiety is a $C_{2-20}$ polyol moiety. In some embodiments, a backbone moiety is a glycerol moiety. In some embodiments, a backbone moiety is a glycerol moiety substituted with one or more TCA cycle acid moieties and/or one or more ketone body moieties, for example, one or more hydroxyl groups are converted to one or more ester groups by esterification with one or more TCA cycle acids and/or ketone bodies. In some embodiments, a backbone moiety is optionally substituted with a moiety selected from the group consisting of TCA cycle intermediate moieties, carboxylic acid (e.g., R'—C(O)OH which can be metabolized to provide one or more ketone bodies, acetyl-CoA and/or propionyl-CoA, and which, in some embodiments, is not a TCA cycle acid) moieties, or a combination thereof. In some embodiments, a backbone moiety is optionally substituted with a moiety selected from the group consisting of TCA cycle intermediate moieties, carboxylic acid (e.g., R'—C(O)OH which can be metabolized to provide one or more ketone bodies, acetyl-CoA and/or propionyl-CoA, and which, in some embodiments, is not a TCA cycle acid) moieties, and combinations thereof. In some embodiments, at least one backbone moiety comprises a TCA cycle acid moiety, and at least one backbone moiety comprises a carboxylic acid (e.g., R'—C(O)OH which can be metabolized to provide one or more ketone bodies, acetyl-CoA and/or propionyl-CoA, and which, in some embodiments, is not a TCA cycle acid) moiety. In some embodiments, a backbone moiety is a $C_{2-20}$ polyol moiety. In some embodiments, a backbone moiety is a glycerol moiety. In some embodiments, a backbone moiety is a glycerol moiety substituted with one or more TCA cycle acid moieties and/or one or more carboxylic acid (e.g., R'—C(O)OH which can be metabolized to provide one or more ketone bodies, acetyl-CoA and/or propionyl-CoA, and which, in some embodiments, is not a TCA cycle acid) moieties, for example, one or more hydroxyl groups are converted to one or more ester groups by esterification with one or more TCA cycle acids and/or carboxylic acids (e.g., R'—C(O)OH which can be metabolized to provide one or more ketone bodies, acetyl-CoA and/or propionyl-CoA, and which, in some embodiments, is not a TCA cycle acid).

In some embodiments, a backbone moiety and a TCA cycle acid moiety or a ketone body moiety are connected through connecting groups, e.g., ester, amide, anhydride, ketal, and/or carbamate groups. In some embodiments, a backbone moiety and a TCA cycle acid moiety or a ketone body moiety are connected through ester bonds. In some embodiments, when the connecting groups, e.g., ester groups, are hydrolyzed (converting back to the corresponding carboxylic acid groups and hydroxyl groups for ester groups), the hydrolysis products consist of one or more TCA cycle acids, one or more ketone bodies, and the backbone moiety compounds (e.g., glycerol). In some embodiments, a backbone moiety and a TCA cycle acid moiety or a carboxylic acid (e.g., R'—C(O)OH which can be metabolized to provide one or more ketone bodies, acetyl-CoA and/or propionyl-CoA, and which, in some embodiments, is not a TCA cycle acid) moiety are connected through connecting groups, e.g., ester, amide, anhydride, ketal, and/or carbamate groups. In some embodiments, a backbone moiety and a TCA cycle acid moiety or a carboxylic acid moiety are connected through ester bonds. In some embodiments, when the connecting groups, e.g., ester groups, are hydrolyzed (converting back to the corresponding carboxylic acid groups and hydroxyl groups for ester groups), the hydrolysis products consist of one or more TCA cycle acids, one or more carboxylic acids (e.g., R'—C(O)OH which can be metabolized to provide one or more ketone bodies, acetyl-CoA and/or propionyl-CoA, and which, in some embodiments, is not a TCA cycle acid), and the backbone moiety compounds (e.g., glycerol).

In some embodiments, backbone moieties are from one or more backbone moiety compounds. Those skilled in the art will appreciate that a variety of suitable backbone moiety compounds might be utilized in accordance with the present disclosure for connecting TCA cycle acids and ketone bodies, and/or TCA cycle acids and carboxylic acids (e.g., R'—C(O)OH which can be metabolized to provide one or more ketone bodies, acetyl-CoA and/or propionyl-CoA, and which, in some embodiments, is not a TCA cycle acid), e.g., through hydroxyl, alkenyl, ketone, carboxyl groups, etc. In some embodiments, a backbone moiety compound is a compound comprising one or more functional groups that can connect one or more TCA cycle acids and one or more carboxylic acids (e.g., R'—C(O)OH which can be metabolized to provide one or more ketone bodies, acetyl-CoA and/or propionyl-CoA, and which, in some embodiments, is not a TCA cycle acid). In some embodiments, a backbone moiety compound comprises two or more functional groups selected from hydroxyl, amino, carbonyl, carboxyl groups, etc. In some embodiments, a backbone moiety compound is a polyol, polyamine, aminoalcohol, etc. In some embodiments, a backbone moiety compound is a $C_{2-10}$ aliphatic compound substituted with two or more groups selected from hydroxyl, amino, carbonyl, and carboxyl groups. In some embodiments, a backbone moiety compound is a $C_{2-10}$ aliphatic compound substituted with two or more groups selected from hydroxyl, amino, and carboxyl groups. In some embodiments, a backbone moiety compound is a $C_{2-10}$ polyol. In some embodiments, a backbone moiety compound is a $C_{2-10}$ polyamine. In some embodiments, a backbone moiety compound is a $C_{2-10}$ aminoalcohol. In some embodiments, a backbone moiety compound is glycerol. In some embodiments, a backbone moiety compound is a polyol. In some embodiments, a backbone moiety compound is a biocompatible polyol. Exemplary polyols are widely known in the art, for example, those described in U.S. Pat. No. 8,912,304, whose polyols are incorporated herein by reference.

In some embodiments, a provided compound comprises two or more backbone moieties optionally linked via one or more linker moieties. In some embodiments, a provided compound consists of two or more backbone moieties optionally linked via one or more linker moieties. In some embodiments, a linker moieties form two or more connecting groups, e.g., ester, amide, anhydride, ketal, and/or carbamate groups, with two or more backbone moieties. In some embodiments, a linker moiety is a TCA cycle diacid or triacid moiety. In some embodiments, a linker moiety is a TCA cycle diacid moiety. In some embodiments, a linker moiety is a TCA cycle triacid moiety. In some embodiments, a linker moiety is a succinic acid moiety linking two diol or polyol (e.g., glycerol) backbone moieties, each of which is independently substituted with one or more moieties selected from TCA cycle acid moieties, one or more moieties having the structure R'—C(O)O—, and combinations thereof. In some embodiments, a linker moiety is a succinic acid moiety linking two glycerol backbone moieties, each of which is independently substituted with one or more moieties selected from TCA cycle acid moieties, ketone body moieties and combinations thereof.

In some embodiments, a combination comprises both physical and chemical combination. In some embodiments, such a combination is a composition comprising a TCA cycle acid or a salt thereof, a ketone body or a salt thereof, and a compound of formula I or a salt thereof. In some embodiments, a combination comprises both physical and chemical combination. In some embodiments, such a combination is a composition comprising a TCA cycle acid or a salt thereof, a carboxylic acid (e.g., R'—C(O)OH which can be metabolized to provide one or more ketone bodies, acetyl-CoA and/or propionyl-CoA, and which, in some embodiments, is not a TCA cycle acid) or a salt thereof, and/or a compound of formula I or a salt thereof.

In some embodiments, the present disclosure provides compounds that provide chemical combinations of one or more TCA cycle acids and one or more ketone body. In some embodiments, a provided compound is a combination compound. In some embodiments, a provided combination compound has the structure of formula I:

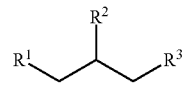

or a salt thereof, wherein:
each of $R^1$, $R^2$ and $R^3$ is independently —H, —OH, —R', or —OC(O)R, or may be independently and optionally taken together with a hydrogen atom on the carbon atom to which it is attached to form an oxo group;
each R and R' is independently linear or branched $C_1$-$C_{100}$ aliphatic wherein one or more —CH$_2$— units are independently and optionally replaced with —O—, —C(O)—, —CH(OH)— or —C(O)O—, and any two R or R' groups may be linked by one or more linear or branched, bivalent or polyvalent, $C_1$-$C_{100}$ hydrocarbon group wherein one or more —CH$_2$— units are independently and optionally replaced with —O—, —C(O)—, —CH(OH)— or —C(O)O—;
at least one of $R^1$, $R^2$ and $R^3$ is —OC(O)R; and
wherein when each ester group of the compound of formula I is hydrolyzed, each of the hydrolysis product is independently a compound selected from a TCA cycle acid or a salt thereof, or a ketone body or a salt thereof, and glycerol;
at least one hydrolysis product is a TCA cycle acid; and
at least one hydrolysis product is a ketone body.

In some embodiments, the present disclosure provides compounds that provide chemical combinations of one or more TCA cycle acids and one or more ketone body. In some embodiments, a provided compound is a combination compound. In some embodiments, a provided combination compound has the structure of formula I:

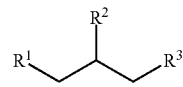

or a salt thereof, wherein:
each of $R^1$, $R^2$ and $R^3$ is independently —H, —OH, —R', or —OC(O)R, or may be independently and optionally taken together with a hydrogen atom on the carbon atom to which it is attached to form an oxo group;
each R and R' is independently linear or branched $C_1$-$C_{100}$ aliphatic wherein one or more —CH$_2$— units are independently replaced with —O—, —C(O)—, —CH(OH)— or —C(O)O—, and any two R or R' groups may be linked by one or more linear or branched, bivalent or polyvalent, $C_1$-$C_{100}$ hydrocarbon group wherein one or more —CH$_2$— units are independently replaced with —O—, —C(O)—, —CH(OH)— or —C(O)O—;
at least one of $R^1$, $R^2$ and $R^3$ is —OC(O)R; and
wherein when each ester group of the compound of formula I is hydrolyzed, each of the hydrolysis product is independently a compound selected from a TCA cycle acid or a salt thereof, or a ketone body or a salt thereof, and glycerol;
at least one hydrolysis product is a TCA cycle acid; and
at least one hydrolysis product is a ketone body.

In some embodiments, each of $R^1$, $R^2$ and $R^3$ is independently —H, —OH, —R', or —OC(O)R;

each R and R' is independently linear or branched $C_1$-$C_{100}$ aliphatic wherein one or more —$CH_2$— units are independently replaced with —O—, —C(O)—, —CH(OH)— or —C(O)O—, and any two R or R' groups may be linked by one or more linear or branched, bivalent or polyvalent, $C_1$-$C_{10}$ hydrocarbon group wherein one or more —$CH_2$— units are independently replaced with —O—, —C(O)—, —CH(OH)— or —C(O)O—;

at least one of $R^1$, $R^2$ and $R^3$ is —OC(O)R; and wherein when each ester group of the compound of formula I is hydrolyzed, each of the hydrolysis product is independently a compound selected from a TCA cycle acid or a salt thereof, or a ketone body or a salt thereof, and glycerol;

at least one hydrolysis product is a TCA cycle acid; and at least one hydrolysis product is a ketone body.

In some embodiments, the present disclosure provides compounds that provide chemical combinations of one or more TCA cycle acids and one or more carboxylic acids (e.g., R'—C(O)OH which can be metabolized to provide one or more ketone bodies, acetyl-CoA and/or propionyl-CoA, and which, in some embodiments, is not a TCA cycle acid). In some embodiments, a provided compound is a combination compound. In some embodiments, a provided combination compound has the structure of formula I:

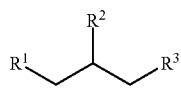

or a salt thereof, wherein:

each of $R^1$, $R^2$ and $R^3$ is independently —H, —OH, R, or R—C(O)O—, or may be independently and optionally taken together with a hydrogen atom on the carbon atom to which it is attached to form an oxo group;

each R is independently linear or branched $C_1$-$C_{100}$ aliphatic wherein one or more —$CH_2$ units are independently and optionally replaced with —O—, —C(O)—, —CH(OH)—, or —C(O)O—, and any two or more R groups may be linked by one or more linear or branched, bivalent or polyvalent, $C_1$-$C_{100}$ hydrocarbon group wherein one or more —$CH_2$— units are independently and optionally replaced with —O—, —C(O)—, —CH(OH)—, or —C(O)O—;

at least one of $R^1$, $R^2$ and $R^3$ is R—C(O)O—; and wherein when each ester group of the compound of formula I is hydrolyzed into its corresponding —OH and —COOH groups, each hydrolysis product is independently a compound selected from a TCA cycle acid or a salt thereof, a $C_2$-$C_{20}$ diol or polyol, and R'—C(O)OH or a salt thereof;

R' is $C_1$-$C_{20}$ aliphatic wherein one or more —$CH_2$— units are independently and optionally replaced with —O—, —C(O)—, —CH(OH)—, or —C(O)O—; and at least one hydrolysis product is a TCA cycle acid or a salt thereof.

In some embodiments, each of $R^1$, $R^2$ and $R^3$ is independently —H, —OH, R, or R—C(O)O—;

each R is independently linear or branched $C_1$-$C_{100}$ aliphatic wherein one or more —$CH_2$ units are independently and optionally replaced with —O—, —C(O)—, —CH(OH)—, or —C(O)O—, and any two or more R groups may be linked by one or more linear or branched, bivalent or polyvalent, $C_1$-$C_{100}$ hydrocarbon group wherein one or more —$CH_2$— units are independently and optionally replaced with —O—, —C(O)—, —CH(OH)—, or —C(O)O—;

at least one of $R^1$, $R^2$ and $R^3$ is R—C(O)O—;

wherein when each ester group of the compound of formula I is hydrolyzed into its corresponding —OH and —COOH groups, each hydrolysis product is independently a compound selected from a TCA cycle acid or a salt thereof, a $C_2$-$C_{20}$ diol or polyol, and R'—C(O)OH or a salt thereof;

R' is $C_1$-$C_{20}$ aliphatic; and at least one hydrolysis product is a TCA cycle acid or a salt thereof.

In some embodiments, each of $R^1$, $R^2$ and $R^3$ is independently —H, —OH, R, or R—C(O)O—;

each R is independently linear or branched $C_1$-$C_{100}$ aliphatic wherein one or more —$CH_2$— units are independently and optionally replaced with —O—, —C(O)—, —CH(OH)—, or —C(O)O—, and any two or more R groups may be linked by one or more linear or branched, bivalent or polyvalent, $C_1$-$C_{100}$ hydrocarbon group wherein one or more —$CH_2$— units are independently and optionally replaced with —O—, —C(O)—, —CH(OH)—, or —C(O)O—;

at least one of $R^1$, $R^2$ and $R^3$ is R—C(O)O—;

wherein when each ester group of the compound of formula I is hydrolyzed into its corresponding —OH and —COOH groups, each hydrolysis product is independently a compound selected from a TCA cycle acid or a salt thereof, a $C_2$-$C_{20}$ diol or polyol, and R'—C(O)OH or a salt thereof;

R' is $C_1$-$C_{20}$ alkyl; and at least one hydrolysis product is a TCA cycle acid or a salt thereof.

In some embodiments, each of $R^1$, $R^2$ and $R^3$ is independently —H, —OH, R, or R—C(O)O—;

each R is independently linear or branched $C_1$-$C_{100}$ aliphatic wherein one or more —$CH_2$— units are independently and optionally replaced with —O—, —C(O)—, —CH(OH)—, or —C(O)O—, and any two or more R groups may be linked by one or more linear or branched, bivalent or polyvalent, $C_1$-$C_{100}$ hydrocarbon group wherein one or more —$CH_2$— units are independently and optionally replaced with —O—, —C(O)—, —CH(OH)—, or —C(O)O—;

at least one of $R^1$, $R^2$ and $R^3$ is R—C(O)O—;

wherein when each ester group of the compound of formula I is hydrolyzed into its corresponding —OH and —COOH groups, each hydrolysis product is independently a compound selected from a TCA cycle acid or a salt thereof, a $C_2$-$C_{20}$ diol or polyol, and R'—C(O)OH or a salt thereof;

R' is $C_1$-$C_{20}$ linear alkyl; and at least one hydrolysis product is a TCA cycle acid or a salt thereof.

In some embodiments, hydrolysis comprises converting each ester group into its corresponding carboxyl group and hydroxyl group. In some embodiments, hydrolysis consists of converting each ester group into its corresponding carboxyl group and hydroxyl group. In some embodiments, a person having ordinary skill in the art does not need to perform an actual hydrolysis reaction to determine the hydrolysis products, as he or she can easily determine the products based on common knowledge, for example, esters can be hydrolyzed to form the corresponding acids and alcohols.

In some embodiments, hydrolysis of a provided compound and/or composition comprises hydrolysis of ketal groups and carboxylic acid derivative groups, if present. In some embodiments, hydrolysis of a provided compound and/or composition comprises hydrolysis of ketal, ester, amide, carbamate and anhydride groups, if present. In some embodiments, hydrolysis of a provided compound and/or composition comprises hydrolysis of ketal, ester, and amide groups, if present. In some embodiments, hydrolysis of a provided compound and/or composition comprises hydrolysis of ketal and ester groups, if present. In some embodiments, hydrolysis of a provided compound and/or composition consists of hydrolysis of ketal groups and carboxylic acid derivative groups, if present. In some embodiments, hydrolysis of a provided compound and/or composition consists of hydrolysis of ketal, ester, amide, carbamate and anhydride groups, if present. In some embodiments, hydrolysis of a provided compound and/or composition consists of hydrolysis of ketal, ester, and amide groups, if present. In some embodiments, hydrolysis of a provided compound and/or composition consists of hydrolysis of ketal and ester groups, if present. A person having ordinary skill in the art can readily determine the hydrolysis products of these groups without performing actual experimentation. For example, as widely known in the art, a ketal may be hydrolyzed to form a ketone and one or more alcohols, an amide may be hydrolyzed to form an acid and an amine, an anhydride may be hydrolyzed to form two acids, etc.

In some embodiments, $R^1$ is hydrogen. In some embodiments, $R^1$ is —OH. In some embodiments, $R^1$ is —R'. In some embodiments, $R^1$ is R—C(O)O—. In some embodiments, $R^1$ is R'—C(O)O—.

In some embodiments, $R^2$ is hydrogen. In some embodiments, $R^2$ is —OH. In some embodiments, $R^2$ is —R'. In some embodiments, $R^2$ is R—C(O)O—. In some embodiments, $R^2$ is R'—C(O)O—.

In some embodiments, $R^3$ is hydrogen. In some embodiments, $R^3$ is —OH. In some embodiments, $R^3$ is —R'. In some embodiments, $R^3$ is R—C(O)O—. In some embodiments, $R^3$ is R'—C(O)O—.

In some embodiments, each of $R^1$, $R^2$ and $R^3$ is independently R—C(O)O—. In some embodiments, each of $R^1$, $R^2$ and $R^3$ is different. In some embodiments, two of $R^1$, $R^2$ are the same and is different from the third. In some embodiments, two of $R^1$, $R^2$ and $R^3$ are independently R—C(O)O—. In some embodiments, two of $R^1$, $R^2$ and $R^3$ are independently R'—C(O)O—.

In some embodiments, R—C(O)O— is a moiety whose corresponding acid R—C(O)OH is a TCA cycle acid. In some embodiments, R—C(O)O— is a moiety whose corresponding acid R—C(O)OH is R'—C(O)—OH. In some embodiments, R—C(O)O— is a moiety whose corresponding acid R—C(O)OH is R'—C(O)—OH which is not a TCA cycle acid or a ketone body. In some embodiments, R—C(O)O— is a moiety whose corresponding acid R—C(O)OH is R'—C(O)—OH which is not a TCA cycle acid. In some embodiments, R—C(O)O— is a moiety whose corresponding acid R—C(O)OH is R'—C(O)—OH which is not a ketone body.

In some embodiments, $R^1$, $R^2$, and/or $R^3$ is independently R—OC(O)-$L^1$-C(O)—O—, wherein each —OC(O)-$L^1$-C(O)— is independently a moiety whose corresponding acid HOC(O)-$L^1$-C(O)OH is a diacid or triacid of the TCA cycle, wherein R is linear or branched $C_{10}$-$C_{100}$ aliphatic wherein one or more —$CH_2$— units are independently and optionally replaced with —O—, —C(O)—, —CH(OH)—, or —C(O)O—. In some embodiments, R comprises one or more R'—C(O)O— moieties. In some embodiments, R comprises two or more R'—C(O)O— moieties. In some embodiments, R comprises three or more R'—C(O)O— moieties. In some embodiments, R comprises four or more R'—C(O)O— moieties. In some embodiments, R' is $C_1$-$C_{20}$ aliphatic. In some embodiments, R' is $C_1$-$C_{20}$ alkyl. In some embodiments, R' is $C_1$-$C_{20}$ linear alkyl. In some embodiments, R'—C(O)OH is not a TCA cycle acid or a ketone body. In some embodiments, R'—C(O)OH is not a TCA cycle acid. In some embodiments, R' is $C_3$-$C_{20}$ linear alkyl. In some embodiments, R' is $C_3$-$C_{10}$ linear alkyl. In some embodiments, R'—C(O)OH is not a ketone body.

In some embodiments, R—C(O)O— is a moiety whose corresponding acid R—C(O)OH is a TCA cycle acid or ketone body acid. In some embodiments, R—C(O)O— is a moiety whose corresponding acid R—C(O)OH is a TCA cycle acid or beta-hydroxybutyric acid. In some embodiments, R—C(O)O— is a moiety whose corresponding acid R—C(O)OH is a TCA cycle acid. In some embodiments, R—C(O)O— is a moiety whose corresponding acid R—C(O)OH is beta-hydroxybutyric acid. In some embodiments, R—C(O)O— is a moiety whose corresponding acid R—C(O)OH is D-beta-hydroxybutyric acid. In some embodiments, R—C(O)O— is a moiety whose corresponding acid R—C(O)OH is acetoacetic acid.

In some embodiments, each of $R^1$, $R^2$ and $R^3$ is independently R—C(O)O—, wherein each R—C(O)O— is independently a moiety whose corresponding acid R—C(O)OH is succinic acid or beta-hydroxybutyric acid. In some embodiments, each of $R^1$, $R^2$ and $R^3$ is independently R—C(O)O—, wherein each —OC(O)R is independently a moiety whose corresponding acid R—C(O)OH is succinic acid or D-beta-hydroxybutyric acid. As a person having ordinary skill in the art understands, the R—C(O)O— moiety whose corresponding acid R—C(O)OH is succinic acid has the structure of —OC(O)$CH_2CH_2$C(O)OH, and the moiety whose corresponding acid R—C(O)OH is beta-hydroxybutyric acid has the structure of —OC(O)$CH_2$CH(OH)$CH_3$. In some embodiments, two of $R^1$, $R^2$ and $R^3$ are a moiety whose corresponding acid R—C(O)OH is succinic acid, and the third is a moiety whose corresponding acid R—C(O)OH is beta-hydroxybutyric acid. In some embodiments, two of $R^1$, $R^2$ and $R^3$ are a moiety whose corresponding acid R—C(O)OH is succinic acid, and the third is a moiety whose corresponding acid R—C(O)OH is D-beta-hydroxybutyric acid. In some embodiments, one of $R^1$, $R^2$ and $R^3$ is a moiety whose corresponding acid R—C(O)OH is succinic acid, and the other two are a moiety whose corresponding acid R—C(O)OH is beta-hydroxybutyric acid. In some embodiments, one of $R^1$, $R^2$ and $R^3$ is a moiety whose corresponding acid R—C(O)OH is succinic acid, and the other two are a moiety whose corresponding acid R—C(O)OH is D-beta-hydroxybutyric acid.

In some embodiments, a provided compound is

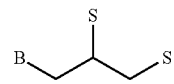

or a salt thereof, wherein B is —OC(O)$CH_2$CH(OH)$CH_3$ and S is —OC(O)$CH_2CH_2$C(O)OH. In some embodiments, a provided compound is

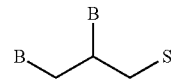

or a salt thereof, wherein B is —OC(O)$CH_2$CH(OH)$CH_3$ and S is —OC(O)$CH_2CH_2$COOH. As understood by a person having ordinary skill in the art understands, B is a moiety whose corresponding acid is beta-hydroxybutyric acid, and S is a moiety whose corresponding acid is succinic acid. In some embodiments, B is a moiety whose corresponding acid is D-beta-hydroxybutyric acid.

As appreciated by persons having ordinary skill in the art, in compounds such as

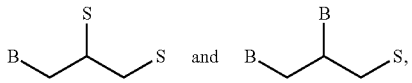

TCA cycle intermediate (e.g. TCA cycle acid) moieties (S) and ketone body moieties (B) are connected by backbone moieties (in

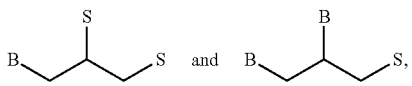

by a backbone moiety whose corresponding backbone moiety compound is glycerol), and these compounds comprise a glycerol backbone moiety substituted with at least one TCA cycle intermediate moiety and at least one ketone body moiety (all three hydroxyl groups converted to ester groups). When

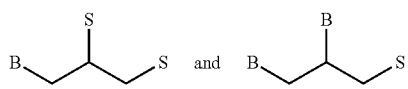

are hydrolyzed by hydrolysis of each ester group, the corresponding hydrolysis products are beta-hydroxybutyric acid, succinic acid and glycerol. In some embodiments, when B is a D-beta-hydroxybutyric acid moiety, the corresponding hydrolysis products are D-beta-hydroxybutyric acid, succinic acid and glycerol.

In some embodiments, each of $R^1$, $R^2$ and $R^3$ is independently —B, —S, or —S'—B'; B is —OC(O)CH$_2$CH(OH)CH$_3$; S is —OC(O)CH$_2$CH$_2$C(O)OH; S' is —OC(O)CH$_2$CH$_2$C(O)O—; B' is —CH(CH$_3$)CH$_2$C(O)OH; and wherein when one of $R^1$, $R^2$ and $R^3$ is B or S, at least two of $R^1$, $R^2$ and $R^3$ are different.

In some embodiments, each of $R^1$, $R^2$ and $R^3$ is independently —OC(O)-L$^1$-C(O)—O-L$^2$-C(O)OH, wherein each —OC(O)-L$^1$-C(O)— is independently a moiety whose corresponding acid HOC(O)-L$^1$-C(O)OH is a diacid or triacid of the TCA cycle, and each —O-L$^2$-C(O)OH is independently a moiety whose corresponding hydroxyacid HO-L$^2$-C(O)OH is beta-hydroxybutyric acid. In some embodiments, each —O-L$^2$-C(O)OH is independently a moiety whose corresponding hydroxyacid HO-L$^2$-C(O)OH is D-beta-hydroxybutyric acid. In some embodiments, —OC(O)-L$^1$-C(O)—O-L$^2$-C(O)OH is —S'—B'.

In some embodiments, a provided compound is

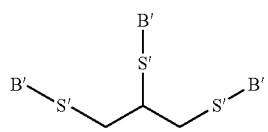

or a salt thereof, wherein S' is —OC(O)CH$_2$CH$_2$C(O)O—, and B' is —CH(CH$_3$)CH$_2$C(O)OH. In some embodiments, the corresponding ketone body of B', H—B', is D-beta-beta-hydroxybutyric acid.

As understood by persons having ordinary skill in the art,

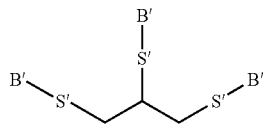

comprise a backbone moiety (glycerol backbone moiety) substituted with combinations of TCA cycle acid moieties and ketone body moieties (converting all —OH into —S'—B').

In some embodiments, a provided compound has the structure of $U_1$-[$U_2$-$U_3$]$_n$-$U_4$-$U_5$, wherein:

$U^1$ is

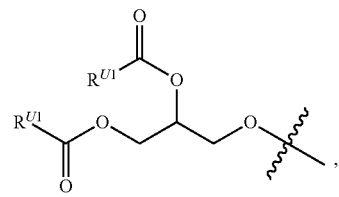

wherein each $R^{U1}$—C(O)O— is independently a moiety whose corresponding acid $R^{U1}$—C(O)OH is a TCA cycle acid, beta-hydroxybutyric acid or acetoacetic acid;

each of $U^2$ and $U^4$ is independently —C(O)-L$^1$-C(O)—, wherein each —C(O)-L$^1$-C(O)— is independently a moiety whose corresponding acid HOC(O)-L$^1$-C(O)OH is a TCA cycle diacid or triacid;

each $U^3$ is independently

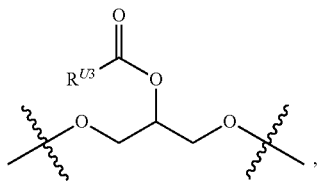

wherein each $R^{U3}$—C(O)O— is independently a moiety whose corresponding acid $R^{U3}$—C(O)OH is a TCA cycle acid, beta-hydroxybutyric acid or acetoacetic acid;

n is 0-100;

$U^5$ is

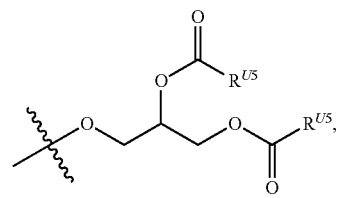

wherein each $R^{U5}$ is independently a moiety whose corresponding acid $R^{U5}$—C(O)OH is a TCA cycle acid, beta-hydroxybutyric acid or acetoacetic acid; and wherein at least one of $R^{U1}$—C(O)O—, $R^{U3}$—C(O)O—, and $R^{U5}$—C(O)O— is a moiety whose corresponding acid is beta-hydroxybutyric acid or acetoacetic acid.

In some embodiments, $U^1$ is

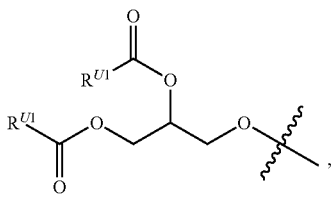

wherein each $R^{U1}$—C(O)O— is independently a moiety whose corresponding acid $R^{U1}$—C(O)OH is a TCA cycle acid or beta-hydroxybutyric acid;

each of $U^2$ and $U^4$ is independently —C(O)-$L^1$-C(O)—, wherein each —C(O)-$L^1$-C(O)— is independently a moiety whose corresponding acid HOC(O)-$L^1$-C(O)OH is a TCA cycle diacid or triacid;

each $U^3$ is independently

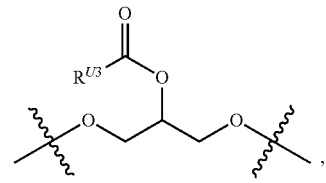

wherein each $R^{U3}$—C(O)O— is independently a moiety whose corresponding acid $R^{U3}$—C(O)OH is a TCA cycle acid or beta-hydroxybutyric acid;

n is 0-20;

$U^5$ is

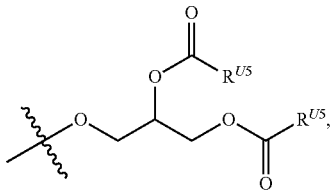

wherein each $R^{U5}$ is independently a moiety whose corresponding acid $R^{U5}$—C(O)OH is a TCA cycle acid or beta-hydroxybutyric acid; and wherein at least one of $R^{U1}$—C(O)O—, $R^{U3}$—C(O)O—, and $R^{U5}$—C(O)O— is a moiety whose corresponding acid is beta-hydroxybutyric acid.

In some embodiments, a provided compound has the structure of $U_1$-$[U_2$-$U_3]_n$-$U_4$-$U_5$, wherein:

$U^1$ is

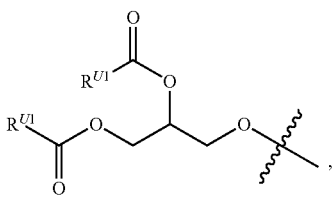

wherein each $R^{U1}$—C(O)O— is independently a moiety whose corresponding acid $R^{U1}$—C(O)OH is a TCA cycle acid or beta-hydroxybutyric acid;

each of $U^2$ and $U^4$ is independently —C(O)-$L^1$-C(O)—, wherein each —C(O)-$L^1$-C(O)— is independently a moiety whose corresponding acid HOC(O)-$L^1$-C(O)OH is a TCA cycle diacid or triacid;

each $U^3$ is independently

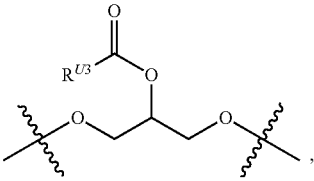

wherein each $R^{U3}$—C(O)O— is independently a moiety whose corresponding acid $R^{U3}$—C(O)OH is a TCA cycle acid or beta-hydroxybutyric acid;

n is 0-100;

$U^5$ is

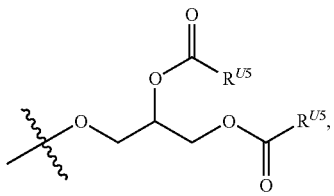

wherein each $R^{U5}$ is independently a moiety whose corresponding acid $R^{U5}$—C(O)OH is a TCA cycle acid or beta-hydroxybutyric acid; and wherein at least one of $R^{U1}$—C(O)O—, $R^{U3}$—C(O)O—, and $R^{U5}$—C(O)O— is a moiety whose corresponding acid is beta-hydroxybutyric acid.

In some embodiments, n is 0-90. In some embodiments, n is 0-80. In some embodiments, n is 0-70. In some embodiments, n is 0-60. In some embodiments, n is 0-50. In some embodiments, n is 0-40. In some embodiments, n is 0-30. In some embodiments, n is 0-20. In some embodiments, n is 0-15. In some embodiments, n is 0-10. In some embodiments, n is 0-9. In some embodiments, n is 0-8. In some embodiments, n is 0-7. In some embodiments, n is 0-6. In some embodiments, n is 0-5. In some embodiments, n is 0-4. In some embodiments, n is 0-3. In some embodiments, n is 0-2. In some embodiments, n is 0-1. In some embodiments, n is 0. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In some embodiments, each $R^{U1}$—C(O)O— is different. In some embodiments, both $R^{U1}$—C(O)O— are the same. In some embodiments, each $R^{U1}$—C(O)O— is independently a moiety whose corresponding acid $R^{U1}$—C(O)OH is succinic acid or beta-hydroxybutyric acid. In some embodiments, each $R^{U1}$—C(O)O— is independently a moiety whose corresponding acid $R^{U}$1-C(O)OH is succinic acid or D-beta-hydroxybutyric acid.

In some embodiments, —C(O)-$L^1$-C(O)— is a moiety whose corresponding acid HOC(O)-$L^1$-C(O)OH is a TCA cycle diacid. In some embodiments, each —C(O)-$L^1$-C(O)— is independently a moiety whose corresponding acid HOC(O)-$L^1$-C(O)OH is a TCA cycle diacid. In some embodiments, —C(O)-$L^1$-C(O)— is a moiety whose corresponding acid HOC(O)-L¹-C(O)OH is a TCA cycle triacid. In some embodiments, each —C(O)-L¹-C(O)— is a moiety whose corresponding acid HOC(O)-L¹-C(O)OH is succinic acid.

In some embodiments, each $R^{U3}$—C(O)O— is independently a moiety whose corresponding acid $R^{U3}$—C(O)OH is a TCA cycle acid or beta-hydroxybutyric acid. In some embodiments, each $R^{U3}$—C(O)O— is independently a moiety whose corresponding acid $R^{U3}$—C(O)OH is a TCA cycle acid or D-beta-hydroxybutyric acid. In some embodiments, $R^{U3}$—C(O)O— is a moiety whose corresponding acid $R^{U3}$—C(O)OH is a TCA cycle acid. In some embodiments, $R^{U3}$—C(O)O— is a moiety whose corresponding acid $R^{U3}$—C(O)OH is succinic acid. In some embodiments, $R^{U3}$—C(O)O— is a moiety whose corresponding acid $R^{U3}$—C(O)OH is beta-hydroxybutyric acid. In some embodiments, $R^{U3}$—C(O)O— is a moiety whose corresponding acid $R^{U3}$—C(O)OH is D-beta-hydroxybutyric acid.

In some embodiments, each $R^{U5}$ is independently a moiety whose corresponding acid $R^{U5}$—C(O)OH is a TCA cycle acid or beta-hydroxybutyric acid. In some embodiments, each $R^{U5}$ is independently a moiety whose corresponding acid $R^{U5}$—C(O)OH is a TCA cycle acid or D-beta-hydroxybutyric acid.

In some embodiments, compounds having the structure of $U_1$-$[U_2$-$U_3]_n$-$U_4$-$U_5$ comprising multiple substituted backbone moieties, e.g., $U_1$, $U_3$, and $U_5$, which are linked by one or more linker moieties, e.g., $U_2$ and $U_4$. Example backbone moieties include but are not limited to those described in the present disclosure.

In some embodiments, n is 0. In some embodiments, a provided compound is

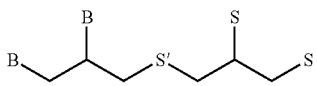

or a salt thereof, wherein B is —OC(O)CH₂CH(OH)CH₃, S' is —OC(O)CH₂CH₂C(O)O—, and S is —OC(O)CH₂CH₂C(O)OH. In some embodiments, n is 1. In some embodiments, a provided compound is

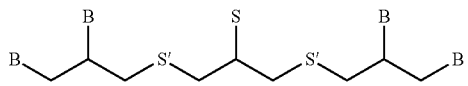

or a salt thereof, wherein B is —OC(O)CH₂CH(OH)CH₃, S' is —OC(O)CH₂CH₂C(O)O—, and S is —OC(O)CH₂CH₂C(O)OH. Such compounds comprise two glycerol backbone moiety linked by one or more linker moieties S'. In some embodiments, the corresponding acid for B, H—B, is D-beta-hydroxybutyric acid.

In some embodiments, a provided compound is formed by condensation of (a) one or more TCA cycle acids, (b) one or more ketone bodies, and (c) optionally one or more backbone moiety compounds, wherein the compound comprises at least one TCA cycle acid moiety derived from a TCA cycle acid, and at least one ketone body moiety derived from a ketone body. In some embodiments, a provided compound is formed by condensation of (a) one or more TCA cycle acids, (b) one or more ketone bodies, and (c) one or more TCA cycle acid moiety derived from a TCA cycle acid, and at least one ketone body moiety derived from a ketone body. In some embodiments, a backbone moiety compound is a $C_{2-20}$ hydrocarbon substituted with two or more amino, hydroxyl and/or carboxyl groups. In some embodiments, a backbone moiety compound is a $C_{2-10}$ polyol. In some embodiments, a provided compound is formed by condensation of (a) one or more TCA cycle acids, (b) one or more ketone bodies, and (c) optionally one or more $C_{2-10}$ polyols, wherein the compound comprises at least one TCA cycle acid moiety derived from a TCA cycle acid, and at least one ketone body moiety derived from a ketone body. In some embodiments, a provided compound is formed by condensation of (a) one or more TCA cycle acids, (b) one or more ketone bodies, and (c) one or more $C_{2-10}$ polyols, wherein the compound comprises at least one TCA cycle acid moiety derived from a TCA cycle acid, and at least one ketone body moiety derived from a ketone body. TCA cycle acids, ketone bodies and polyols comprise functional groups that can link them together, for example, by forming ester groups between carboxyl groups and hydroxyl groups. In some embodiments, a backbone moiety compound is glycerol. In some embodiments, a provided compound is formed by condensation of (a) one or more TCA cycle acids, (b) one or more ketone bodies, and (c) glycerol. In some embodiments, a provided compound is formed by condensation of (a) succinic acid, (b) beta-hydroxybutyric acid, and (c) glycerol. In some embodiments, a provided compound is formed by condensation of (a) succinic acid, (b) D-beta-hydroxybutyric acid, and (c) glycerol. In some embodiments, a provided compound is formed by condensation of (a) succinic acid, and (b) beta-hydroxybutyric acid. In some embodiments, a provided compound is formed by condensation of (a) succinic acid, and (b) D-beta-hydroxybutyric acid. Those skilled in the art will appreciate that a variety of condensation conditions might be utilized in accordance with the present disclosure, including but not limited to those esterification conditions and/or amidation conditions, depending on the chemical identity of the backbone moiety compound.

In some embodiments, the present disclosure provides a compound whose structure comprises a moiety of formula II:

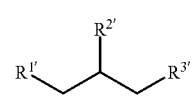

II wherein:
each of $R^{1'}$, $R^{2'}$ and $R^{3'}$ is independently —B, —S, —S'—B', —S', or —B",
B is —OC(O)CH₂CH(OH)CH₃;
S is —OC(O)CH₂CH₂C(O)OH;
S' is —OC(O)CH₂CH₂C(O)O—;
B' is —CH(CH₃)CH₂C(O)OH;
B" is —OC(O)CH₂CH(CH₃)O—; and
wherein when each ester bond in the compound is hydrolyzed, one of the hydrolysis product is succinic acid and one is beta-hydroxybutyric acid.

Compounds of formula II can belong to compounds comprising one or more backbone moieties (glycerol moiety) substituted with one or more TCA cycle acid moieties, one or more ketone body moieties, or combinations thereof (e.g., —B, —S, —S'—B', —S', —B", etc.)

In some embodiments, the present disclosure provides a compound produced by a method comprising steps of reacting a polyol with a TCA cycle acid and a ketone body, so that one or more ester, and optionally ketal, groups are formed linking the polyol, TCA cycle acid, and ketone body. In some embodiments, a plurality of TCA cycle acids are used. In some embodiments, a plurality of ketone bodies are used. In some embodiments, a polyol is glycerol. In some embodiments, the plurality of TCA cycle acids, or the plurality of ketone bodies, are added to the production processes serially, e.g., one TCA cycle acid is let react before the addition of a second TCA cycle acid. In some embodiments, all TCA cycle acids are added concurrently. In some embodiments, all ketone bodies are added concurrently. In some embodiments, two or more polyol units are linked together. In some embodiments, a polyol unit is a glycerol unit. In some embodiments, two or more polyol units are linked together by one or more TCA cycle diacid or triacid moieties. In some embodiments, two or more polyol units are linked together by succinic acid moieties.

In some embodiments, the present disclosure provides a compound comprising one or more backbone moieties and optionally one or more linker moieties, wherein:

each backbone moiety is independently a $C_{2-10}$ hydrocarbon moiety substituted with two or more groups selected from hydroxyl, amino and carboxyl groups;

each backbone moiety is optionally substituted with one or more TCA cycle acid moieties, ketone body moieties or combinations thereof, so that one or more of the groups selected from hydroxyl, amino and carboxyl groups are converted into the corresponding ester, amide or anhydride groups;

each linker moiety is independently a $C_{2-10}$ hydrocarbon moiety substituted with two or more carboxyl groups, and links two or more backbone moieties; and wherein the compound comprises at least one TCA cycle acid moiety and at least one ketone body moiety.

In some embodiments, a backbone moiety is a $C_{2-10}$ hydrocarbon moiety substituted with two or more groups selected from hydroxyl, amino and carboxyl groups. In some embodiments, a backbone moiety is a $C_{2-10}$ hydrocarbon moiety substituted with two or more groups selected from hydroxyl and carboxyl groups. In some embodiments, a backbone moiety is a $C_{2-10}$ hydrocarbon moiety substituted with two or more groups selected from hydroxyl and amino groups. In some embodiments, a backbone moiety is a $C_{2-10}$ hydrocarbon moiety substituted with two or more groups selected from amino and carboxyl groups. In some embodiments, a backbone moiety is a $C_{2-10}$ hydrocarbon moiety substituted with two or more hydroxyl groups. In some embodiments, a backbone moiety is a $C_{2-10}$ hydrocarbon moiety substituted with two or more amino groups. In some embodiments, a backbone moiety is a $C_{2-10}$ hydrocarbon moiety substituted with two or more carboxyl groups. In some embodiments, a backbone moiety is a glycerol moiety. In some embodiments, each backbone moiety is independently a $C_{2-10}$ hydrocarbon moiety substituted with two or more groups selected from hydroxyl and amino groups. In some embodiments, each backbone moiety is independently a $C_{2-10}$ hydrocarbon moiety substituted with two or more hydroxyl groups. In some embodiments, each backbone moiety is independently a glycerol moiety.

In some embodiments, a backbone moiety is optionally substituted with one or more TCA cycle acid moieties, ketone body moieties or combinations thereof, so that one or more of the groups selected from hydroxyl, amino and carboxyl groups are converted into the corresponding ester, amide or anhydride groups. In some embodiments, a backbone moiety is substituted so that one or more of the groups selected from hydroxyl, amino and carboxyl groups are converted into the corresponding ester, amide or anhydride groups. In some embodiments, a backbone moiety is substituted so that each hydroxyl, amino and carboxyl groups of the back moiety is converted into the corresponding ester, amide or anhydride group. In some embodiments, a backbone moiety is substituted with TCA cycle acid moieties, ketone body acid moieties or combinations thereof. In some embodiments, a ketone body acid is acetoacetic acid or beta-hydroxybutyric acid. In some embodiments, a backbone moiety is substituted with TCA cycle acid moieties, beta-hydroxybutyric acid moieties or combinations thereof. In some embodiments, a backbone moiety is substituted with succinic acid moieties, beta-hydroxybutyric acid moieties or combinations thereof.

In some embodiments, each linker moiety is independently a $C_{2-10}$ hydrocarbon moiety substituted with two or more carboxyl groups, and links two or more backbone moieties. In some embodiments, a linker moiety is a TCA cycle diacid or triacid moiety. In some embodiments, a linker moiety is a TCA cycle diacid moiety. In some embodiments, a linker moiety is a TCA cycle triacid moiety. In some embodiments, a linker moiety is a succinic acid moiety.

In some embodiments, a provided compound comprises at least one TCA cycle acid moiety and at least one ketone body moiety. In some embodiments, a provided compound comprises at least one TCA cycle acid moiety and at least one beta-hydroxybutyric acid or acetoacetic acid moiety. In some embodiments, a provided compound comprises at least one TCA cycle acid moiety and at least one beta-hydroxybutyric acid moiety. In some embodiments, a provided compound comprises at least one TCA cycle acid moiety and at least one acetoacetic acid moiety. In some embodiments, a provided compound comprises at least one succinic acid moiety and at least one beta-hydroxybutyric acid or acetoacetic acid moiety. In some embodiments, a provided compound comprises at least one succinic acid moiety and at least one beta-hydroxybutyric acid moiety. In some embodiments, a provided compound comprises at least one succinic acid moiety and at least one acetoacetic acid moiety.

In some embodiments, a provided compound has the structure of formula I-a:

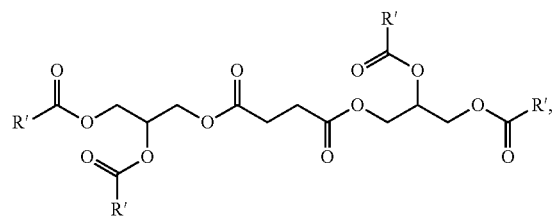

I-a or a salt thereof. In some embodiments, R'—C(O)OH is not a TCA cycle acid or a ketone body. In some embodiments, R'—C(O)OH is not a TCA cycle acid. In some embodiments, R'—C(O)OH is not a ketone body. In some embodiments, R' is $C_1$-$C_{20}$ aliphatic. In some embodiments, R' is $C_1$-$C_{20}$ alkyl. In some embodiments, R' is $C_1$-$C_{20}$ linear alkyl. In some embodiments, R' is $C_3$-$C_{20}$ linear alkyl. In some embodiments, R' is $C_3$-$C_{10}$ linear alkyl.

In some embodiments, a provided compound has the structure of $U_1$-$[U_2$-$U_3]_n$-$U_4$-$U_5$, wherein:

$U^1$ is

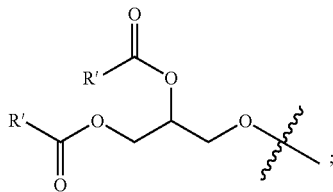

each of $U^2$ and $U^4$ is independently —C(O)-$L^1$-C(O)—, wherein $L^1$ is a bivalent $C_1$-$C_{20}$ aliphatic group wherein one or more —CH$_2$— units are independently and optionally replaced with —O—, —C(O)—, or —C(O)O—;

each $U^3$ is independently

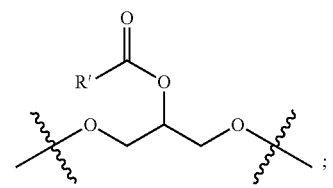

n is 0-20;
$U^5$ is

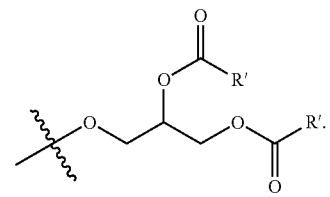

In some embodiments, each —C(O)-$L^1$-C(O)— is independently a moiety whose corresponding acid HOC(O)-$L^1$-C(O)OH is a TCA cycle diacid or triacid. In some embodiments, $L^1$ is —CH$_2$—CH$_2$—.

In some embodiments, R'—C(O)OH is not a TCA acid or a ketone body. In some embodiments, R'—C(O)OH is not a TCA cycle acid. In some embodiments, R'—C(O)OH is not a ketone body. In some embodiments, R' is $C_1$-$C_{20}$ aliphatic. In some embodiments, R' is $C_1$-$C_{20}$ alkyl. In some embodiments, R' is $C_1$-$C_{20}$ linear alkyl. In some embodiments, R' is $C_3$-$C_{20}$ linear alkyl. In some embodiments, R' is $C_3$-$C_{10}$ linear alkyl.

In some embodiments, n is 0-90. In some embodiments, n is 0-80. In some embodiments, n is 0-70. In some embodiments, n is 0-60. In some embodiments, n is 0-50. In some embodiments, n is 0-40. In some embodiments, n is 0-30. In some embodiments, n is 0-20. In some embodiments, n is 0-15. In some embodiments, n is 0-10. In some embodiments, n is 0-9. In some embodiments, n is 0-8. In some embodiments, n is 0-7. In some embodiments, n is 0-6. In some embodiments, n is 0-5. In some embodiments, n is 0-4. In some embodiments, n is 0-3. In some embodiments, n is 0-2. In some embodiments, n is 0-1. In some embodiments, n is 0. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In some embodiments, R'—C(O)O— groups are different. In some embodiments, R'—C(O)O— groups are the same.

In some embodiments, —C(O)-$L^1$-C(O)— is a moiety whose corresponding acid HOC(O)-$L^1$-C(O)OH is a TCA cycle diacid. In some embodiments, each —C(O)-$L^1$-C(O)— is independently a moiety whose corresponding acid HOC(O)-$L^1$-C(O)OH is a TCA cycle diacid. In some embodiments, —C(O)-$L^1$-C(O)— is a moiety whose corresponding acid HOC(O)-$L^1$-C(O)OH is a TCA cycle triacid. In some embodiments, each —C(O)-$L^1$-C(O)— is a moiety whose corresponding acid HOC(O)-$L^1$-C(O)OH is succinic acid.

In some embodiments, compounds having the structure of $U_1$-$[U_2$-$U_3]_n$-$U_4$-$U_5$ comprising multiple substituted backbone moieties, e.g., $U_1$, $U_3$, and $U_5$, which are linked by one or more linker moieties, e.g., $U_2$ and $U_4$.

In some embodiments, a provided compound comprises one or more backbone moieties optionally linked by one or more linker moieties. In some embodiments, a provided compound consists of one or more backbone moieties optionally linked by one or more linker moieties. In some embodiments, a backbone moiety is a $C_{2-20}$ polyol moiety, wherein one or more hydroxyl groups are optionally connected to one or more TCA cycle acid moieties, one or more ketone body moieties, or combinations thereof, and a linker moiety is a TCA cycle diacid or triacid moiety. In some embodiments, a backbone moiety is a $C_{2-20}$ polyol moiety, wherein one or more hydroxyl groups are optionally connected to one or more TCA cycle acid moieties, one or more carboxylic acid moieties, or combinations thereof, and a linker moiety is a TCA cycle diacid or triacid moiety. In some embodiments, a provided compound comprises at least one TCA cycle acid moiety and at least one ketone body moiety.

In some embodiments, carboxylic acid moieties in provided technologies have the structure of R'—C(O)O— or R'—C(O)—. In some embodiments, carboxylic acid moieties have the structure of R'—C(O)O—. In some embodiments, carboxylic acid moieties have the structure of R'—C(O)—. In some embodiments, a corresponding carboxylic acid (e.g., R'—C(O)OH for R'—C(O)O— or R'—C(O)—) is not a carboxylic acid. Example R' groups are extensively described in the present disclosure.

In some embodiments, a provided compound is formed by condensation of (a) one or more TCA cycle acids, (b) one or more compounds having the structure of R'—C(O)OH, wherein R' is $C_1$-$C_{20}$ aliphatic wherein one or more —CH$_2$— units are independently and optionally replaced with —O—, —C(O)—, —CH(OH)—, or —C(O)O—, and (c) optionally one or more backbone moiety compounds. In some embodiments, a provided compound is formed by condensation of (a) one or more TCA cycle acids, (b) one or more compounds having the structure of R'—C(O)OH, wherein R' is $C_1$-$C_{20}$ aliphatic, and (c) optionally one or more backbone moiety compounds. In some embodiments, a backbone moiety compound is a $C_{2-20}$ hydrocarbon substituted with two or more amino, hydroxyl and/or carboxyl groups. In some embodiments, a backbone moiety compound is a $C_{2-10}$ diol or polyol. In some embodiments, a backbone moiety compound is a $C_{2-10}$ diol. In some embodiments, a backbone moiety compound is a $C_{2-10}$ polyol. In some embodiments, a backbone moiety compound is glycerol. Those skilled in the art will appreciate that a variety of condensation conditions might be utilized in accordance with the present disclosure, including but not limited to those esterification conditions and/or amidation conditions, depending on the chemical identity of the backbone moiety compound.

In some embodiments, the present disclosure provides a compound produced by a method comprising steps of reacting a diol or polyol with a TCA cycle acid and a carboxylic acid having the structure of R'—C(O)OH which is not a TCA cycle acid (and which can be metabolized to provide one or more ketone bodies, acetyl-CoA and/or propionyl-CoA), so that one or more ester, and optionally ketal, groups are formed linking the diol or polyol, TCA cycle acid, and carboxylic acid. In some embodiments, a plurality of TCA cycle acids are used. In some embodiments, a plurality of carboxylic acids are used. In some embodiments, a diol or polyol is a diol. In some embodiments, a diol or polyol is a polyol. In some embodiments, a polyol is glycerol. In some embodiments, the plurality of TCA cycle acids, or the plurality of carboxylic acids, are added to the production processes serially, e.g., one TCA cycle acid is let react before the addition of a second TCA cycle acid. In some embodiments, all TCA cycle acids are added concurrently. In some embodiments, all carboxylic acids are added concurrently. In some embodiments, two or more polyol units are linked together. In some embodiments, a polyol unit is a glycerol unit. In some embodiments, two or more polyol units are linked together by one or more TCA cycle diacid or triacid moieties. In some embodiments, two or more polyol units are linked together by succinic acid moieties.

In some embodiments, the present disclosure provides a compound comprising one or more backbone moieties and optionally one or more linker moieties, wherein:

each backbone moiety is independently a $C_{2-10}$ hydrocarbon moiety substituted with two or more groups selected from hydroxyl, amino and carboxyl groups;

each backbone moiety is optionally substituted with one or more TCA cycle acid moieties, carboxylic acid moieties or combinations thereof, so that one or more of the groups selected from hydroxyl, amino and carboxyl groups are converted into the corresponding ester, amide or anhydride groups;

each linker moiety is independently a $C_{2-10}$ hydrocarbon moiety substituted with two or more carboxyl groups, and links two or more backbone moieties; and wherein the compound comprises at least one TCA cycle acid moiety and at least one carboxylic acid moiety.

In some embodiments, a backbone moiety is a $C_{2-10}$ hydrocarbon moiety substituted with two or more groups selected from hydroxyl, amino and carboxyl groups. In some embodiments, a backbone moiety is a $C_{2-10}$ hydrocarbon moiety substituted with two or more groups selected from hydroxyl and carboxyl groups. In some embodiments, a backbone moiety is a $C_{2-10}$ hydrocarbon moiety substituted with two or more groups selected from hydroxyl and amino groups. In some embodiments, a backbone moiety is a $C_{2-10}$ hydrocarbon moiety substituted with two or more groups selected from amino and carboxyl groups. In some embodiments, a backbone moiety is a $C_{2-10}$ hydrocarbon moiety substituted with two or more hydroxyl groups. In some embodiments, a backbone moiety is a $C_{2-10}$ hydrocarbon moiety substituted with two or more amino groups. In some embodiments, a backbone moiety is a $C_{2-10}$ hydrocarbon moiety substituted with two or more carboxyl groups. In some embodiments, a backbone moiety is a glycerol moiety. In some embodiments, each backbone moiety is independently a $C_{2-10}$ hydrocarbon moiety substituted with two or more groups selected from hydroxyl and amino groups. In some embodiments, each backbone moiety is independently a $C_{2-10}$ hydrocarbon moiety substituted with two or more hydroxyl groups. In some embodiments, each backbone moiety is independently a glycerol moiety.

In some embodiments, a backbone moiety is optionally substituted with one or more TCA cycle acid moieties, carboxylic acid moieties or combinations thereof, so that one or more of the groups selected from hydroxyl, amino and carboxyl groups are converted into the corresponding ester, amide or anhydride groups. In some embodiments, a backbone moiety is substituted so that one or more of the groups selected from hydroxyl, amino and carboxyl groups are converted into the corresponding ester, amide or anhydride groups. In some embodiments, a backbone moiety is substituted so that each hydroxyl, amino and carboxyl groups of the back moiety is converted into the corresponding ester, amide or anhydride group. In some embodiments, a backbone moiety is substituted with TCA cycle acid moieties, carboxylic acid moieties or combinations thereof.

In some embodiments, each linker moiety is independently a $C_{2-10}$ hydrocarbon moiety substituted with two or more carboxyl groups, and links two or more backbone moieties. In some embodiments, a linker moiety is a TCA cycle diacid or triacid moiety. In some embodiments, a linker moiety is a TCA cycle diacid moiety. In some embodiments, a linker moiety is a TCA cycle triacid moiety. In some embodiments, a linker moiety is a succinic acid moiety.

In some embodiments, a provided compound comprises at least one TCA cycle acid moiety and at least one carboxylic acid moiety. In some embodiments, a TCA cycle acid moiety is a succinic acid moiety.

In some embodiments, a provided compound is a liquid under room temperature and 1 atm. In some embodiments, a provided compound has a molecular weight ($M_w$ for polymers) of no more than about 10000, 9000, 8000, 7000, 6000, 5000, 4000, 3000, 2000, 1500, 1000, 900, 800, 700, 600, 500, 400 or 300. In some embodiments, the molecular weight is no more than about 10000. In some embodiments, the molecular weight is no more than about 9000. In some embodiments, the molecular weight is no more than about 8000. In some embodiments, the molecular weight is no more than about 7000. In some embodiments, the molecular weight is no more than about 6000. In some embodiments, the molecular weight is no more than about 5000. In some embodiments, the molecular weight is no more than about 4000. In some embodiments, the molecular weight is no more than about 3000. In some embodiments, the molecular weight is no more than about 2000. In some embodiments, the molecular weight is no more than about 1500. In some embodiments, the molecular weight is no more than about 1000. In some embodiments, the molecular weight is no more than about 900. In some embodiments, the molecular weight is no more than about 800. In some embodiments, the molecular weight is no more than about 700. In some embodiments, the molecular weight is no more than about 600. In some embodiments, the molecular weight is no more than about 500. In some embodiments, the molecular weight is no more than about 400. In some embodiments, the molecular weight is no more than about 300.

In some embodiments, a provide compound has no more than about 100, 90, 80, 70, 60, 50, 40, 30, 20, 10, 9, 8, 7, 6, 5, 4, 3, or 2 backbone moieties. In some embodiments, a provided compound has no more than about 100 backbone moieties. In some embodiments, a provided compound has no more than about 50 backbone moieties. In some embodiments, a provided compound has no more than about 40 backbone moieties. In some embodiments, a provided compound has no more than about 30 backbone moieties. In some embodiments, a provided compound has no more than about 20 backbone moieties. In some embodiments, a provided compound has no more than about 10 backbone moieties. In some embodiments, a provided compound has no more than about 9 backbone moieties. In some embodiments, a provided compound has no more than about 8 backbone moieties. In some embodiments, a provided compound has no more than about 7 backbone moieties. In some embodiments, a provided compound has no more than about 6 backbone moieties. In some embodiments, a provided compound has no more than about 5 backbone moieties. In some embodiments, a provided compound has no more than about 4 backbone moieties. In some embodiments, a provided compound has no more than about 3 backbone moieties. In some embodiments, a provided compound has no more than about 2 backbone moieties.

In some embodiments, a provide compound has no more than about 100, 90, 80, 70, 60, 50, 40, 30, 20, 10, 9, 8, 7, 6, 5, 4, 3, or 2 TCA cycle acid and ketone body moieties. In some embodiments, a provided compound has no more than about 100 TCA cycle acid and ketone body moieties. In some embodiments, a provided compound has no more than about 50 TCA cycle acid and ketone body moieties. In some embodiments, a provided compound has no more than about 40 TCA cycle acid and ketone body moieties. In some embodiments, a provided compound has no more than about 30 TCA cycle acid and ketone body moieties. In some embodiments, a provided compound has no more than about 20 TCA cycle acid and ketone body moieties. In some embodiments, a provided compound has no more than about 10 TCA cycle acid and ketone body moieties. In some embodiments, a provided compound has no more than about 9 TCA cycle acid and ketone body moieties. In some embodiments, a provided compound has no more than about 8 TCA cycle acid and ketone body moieties. In some embodiments, a provided compound has no more than about 7 TCA cycle acid and ketone body moieties. In some embodiments, a provided compound has no more than about 6 TCA cycle acid and ketone body moieties. In some embodiments, a provided compound has no more than about 5 TCA cycle acid and ketone body moieties. In some embodiments, a provided compound has no more than about 4 TCA cycle acid and ketone body moieties. In some embodiments, a provided compound has no more than about 3 TCA cycle acid and ketone body moieties.

In some embodiments, a provide compound has no more than about 100, 90, 80, 70, 60, 50, 40, 30, 20, 10, 9, 8, 7, 6, 5, 4, 3, or 2 TCA cycle acid and carboxylic acid moieties. In some embodiments, a provided compound has no more than about 100 TCA cycle acid and carboxylic acid moieties. In some embodiments, a provided compound has no more than about 50 TCA cycle acid and carboxylic acid moieties. In some embodiments, a provided compound has no more than about 40 TCA cycle acid and carboxylic acid moieties. In some embodiments, a provided compound has no more than about 30 TCA cycle acid and carboxylic acid moieties. In some embodiments, a provided compound has no more than about 20 TCA cycle acid and carboxylic acid moieties. In some embodiments, a provided compound has no more than about 10 TCA cycle acid and carboxylic acid moieties. In some embodiments, a provided compound has no more than about 9 TCA cycle acid and carboxylic acid moieties. In some embodiments, a provided compound has no more than about 8 TCA cycle acid and carboxylic acid moieties. In some embodiments, a provided compound has no more than about 7 TCA cycle acid and carboxylic acid moieties. In some embodiments, a provided compound has no more than about 6 TCA cycle acid and carboxylic acid moieties. In some embodiments, a provided compound has no more than about 5 TCA cycle acid and carboxylic acid moieties. In some embodiments, a provided compound has no more than about 4 TCA cycle acid and carboxylic acid moieties. In some embodiments, a provided compound has no more than about 3 TCA cycle acid and carboxylic acid moieties.

In some embodiments, a provided compound has about 2, 3, 4, 5, 6, 7, 8, 9, or 10 to about 100, 90, 80, 70, 60, 50, 40, 30, 20, 15 or 10 TCA cycle acid and ketone body moieties. In some embodiments, a provided compound has 2 to about 100, 90, 80, 70, 60, 50, 40, 30, 20, 10, 9, 8, 7, 6, 5, 4, or 3 TCA cycle acid and ketone body moieties. In some embodiments, a provided compound has 3 to about 100, 90, 80, 70, 60, 50, 40, 30, 20, 10, 9, 8, 7, 6, 5, 4, or 3 TCA cycle acid and ketone body moieties. In some embodiments, a provided compound has 4 to about 100, 90, 80, 70, 60, 50, 40, 30, 20, 10, 9, 8, 7, 6, 5, 4, or 3 TCA cycle acid and ketone body moieties.

In some embodiments, a provided compound has about 2, 3, 4, 5, 6, 7, 8, 9, or 10 to about 100, 90, 80, 70, 60, 50, 40, 30, 20, 15 or 10 TCA cycle acid and carboxylic acid moieties. In some embodiments, a provided compound has 2 to about 100, 90, 80, 70, 60, 50, 40, 30, 20, 10, 9, 8, 7, 6, 5, 4, or 3 TCA cycle acid and carboxylic acid moieties. In some embodiments, a provided compound has 3 to about 100, 90, 80, 70, 60, 50, 40, 30, 20, 10, 9, 8, 7, 6, 5, 4, or 3 TCA cycle acid and carboxylic acid moieties. In some embodiments, a provided compound has 4 to about 100, 90, 80, 70, 60, 50, 40, 30, 20, 10, 9, 8, 7, 6, 5, 4, or 3 TCA cycle acid and carboxylic acid moieties.

In some embodiments, a provided compound has about 30 TCA cycle acid and ketone body moieties. In some embodiments, a provided compound has about 20 TCA cycle acid and ketone body moieties. In some embodiments, a provided compound has about 15 TCA cycle acid and ketone body moieties. In some embodiments, a provided compound has about 10 TCA cycle acid and ketone body moieties. In some embodiments, a provided compound has about 9 TCA cycle acid and ketone body moieties. In some embodiments, a provided compound has about 8 TCA cycle acid and ketone body moieties. In some embodiments, a provided compound has about 7 TCA cycle acid and ketone body moieties. In some embodiments, a provided compound has about 6 TCA cycle acid and ketone body moieties. In some embodiments, a provided compound has about 5 TCA cycle acid and ketone body moieties. In some embodiments, a provided compound has about 4 TCA cycle acid and ketone body moieties. In some embodiments, a provided compound has about 3 TCA cycle acid and ketone body moieties.

In some embodiments, a provided compound has about 30 TCA cycle acid and carboxylic acid moieties. In some embodiments, a provided compound has about 20 TCA cycle acid and carboxylic acid moieties. In some embodiments, a provided compound has about 15 TCA cycle acid and carboxylic acid moieties. In some embodiments, a provided compound has about 10 TCA cycle acid and carboxylic acid moieties. In some embodiments, a provided compound has about 9 TCA cycle acid and carboxylic acid moieties. In some embodiments, a provided compound has about 8 TCA cycle acid and carboxylic acid moieties. In some embodiments, a provided compound has about 7 TCA cycle acid and carboxylic acid moieties. In some embodiments, a provided compound has about 6 TCA cycle acid and carboxylic acid moieties. In some embodiments, a provided compound has about 5 TCA cycle acid and carboxylic acid moieties. In some embodiments, a provided compound has about 4 TCA cycle acid and carboxylic acid moieties. In some embodiments, a provided compound has about 3 TCA cycle acid and carboxylic acid moieties.

Unless otherwise stated, all tautomeric and stereoisomeric forms of the compounds of the disclosure are within the scope of the disclosure. In some embodiments, a beta-hydroxybutyric acid is D-beta-hydroxybutyric acid.

In some embodiments, the present disclosure provides compositions which comprises one or more TCA cycle acid moieties, and one or more ketone body moieties, wherein each TCA cycle acid moiety is independently a TCA cycle acid or a salt thereof, or a structural unit which, upon hydrolysis of the composition, is converted into a TCA cycle acid or a salt thereof; and each ketone body moiety is independently a ketone body or a salt thereof, or a structural unit which, upon hydrolysis of the composition, is converted into a ketone body. In some embodiments, a TCA cycle acid moiety is independently a TCA cycle acid or a salt thereof. In some embodiments, TCA cycle acid moiety is a structural unit which, upon hydrolysis of the composition, is converted into a TCA cycle acid or a salt thereof. In some embodiments, a ketone body moiety is a ketone body or a salt thereof. In some embodiments, a ketone body moiety is a structural unit which, upon hydrolysis of the composition, is converted into a ketone body. In some embodiments, a TCA cycle acid is succinic acid, and a ketone body is beta-hydroxybutyric aid. In some embodiments, a TCA cycle acid is succinic acid, and a ketone body is D-beta-hydroxybutyric acid.

As appreciated by a person having ordinary skill in the art, a ketone body moiety, in some embodiments, is a moiety that is subject to conversion (for example, after administration into a subject and metabolism and/or by degradation in vitro or in vivo), to provide one or more ketone bodies. In some embodiments, a ketone body moiety is or comprises a carboxylic acid moiety, e.g., having the structure of R'—C(O)— or R'—C(O)O—, wherein R' is $C_1$-$C_{20}$ aliphatic wherein one or more —$CH_2$— units are independently replaced with —O—, —C(O)—, —CH(OH)—, or —C(O)O—. In some embodiments, R' is $C_1$-$C_{20}$ aliphatic. In some embodiments, R' is $C_1$-$C_{20}$ linear aliphatic. In some embodiments, R' is $C_1$-$C_{20}$ alkyl. In some embodiments, R' is $C_1$-$C_{20}$ linear alkyl. In some embodiments, as appreciated by a person having ordinary skill in the art, a ketone body moiety, e.g., one having the structure of R'—C(O)— or R'—C(O)O—, is converted to a corresponding carboxylic acid, e.g., one having the structure of R'—C(O)OH, after administration to a subject via, e.g., ester hydrolysis. In some embodiments, a carboxylic acid, for example, one having the structure of R'—C(O)OH, may be metabolized through beta-oxidation to provide acetyl-CoA, which can be used in several pathways to provide energy. In some embodiments, acetyl-CoA is coverted into one or more ketone bodies via, e.g., ketogenesis. In some embodiments, the present disclosure provides a compound having the structure of formula I:

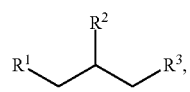

or a salt thereof, wherein:
each of $R^1$, $R^2$ and $R^3$ is independently —H, —OH, R, or R—C(O)O—, or may be independently and optionally taken together with a hydrogen atom on the carbon atom to which it is attached to form an oxo group;

each R is independently linear or branched $C_1$-$C_{100}$ aliphatic wherein one or more —$CH_2$ units are independently and optionally replaced with —O—, —C(O)—, —CH(OH)—, or —C(O)O—, and any two or more R groups may be linked by one or more linear or branched, bivalent or polyvalent, $C_1$-$C_{100}$ hydrocarbon group wherein one or more —$CH_2$— units are independently and optionally replaced with —O—, —C(O)—, —CH(OH)—, or —C(O)O—;

at least one of $R^1$, $R^2$ and $R^3$ is R—C(O)O—; and wherein when each ester group of the compound of formula I is hydrolyzed into its corresponding —OH and —COOH groups, each hydrolysis product is independently a compound selected from a TCA cycle acid or a salt thereof, a $C_2$-$C_{20}$ diol or polyol, and R'—C(O)OH or a salt thereof;

R' is $C_1$-$C_{20}$ aliphatic wherein one or more —$CH_2$— units are independently and optionally replaced with —O—, —C(O)—, —CH(OH)—, or —C(O)O—; and at least one hydrolysis product is a TCA cycle acid or a salt thereof.

In some embodiments, a provided composition comprises a predetermined level of a first compound selected from a first group consisting of TCA cycle acids and salts, amides, esters, ketals, and anhydrides thereof; and a second compound selected from a second group consisting of ketone bodies and salts, amides, esters, ketals, and anhydrides thereof. In some embodiments, a provided composition comprises a predetermined level of a first compound selected from a first group consisting of succinic acid and pharmaceutically acceptable salts, amides, esters, ketals, and anhydrides thereof; and a second compound selected from a second group consisting of beta-hydroxybutyric acid and pharmaceutically acceptable salts, amides, esters, ketals, and anhydrides thereof.

In some embodiments, the present disclosure provides a composition, which when optionally fully hydrolyzed, provides a predetermined level of (a) a TCA cycle acid or salt thereof; and (b) a ketone body or salt thereof. In some embodiments, the present disclosure provides a composition, which when optionally fully hydrolyzed, provides a predetermined level of (a) succinic cycle acid or a salt thereof; and (b) beta-hydroxybutyric acid or a salt thereof. In some embodiments, hydrolysis comprises hydrolysis of all carboxyl derivative groups to provide the corresponding carboxylic acid groups, and hydrolysis of all ketal groups to provide the corresponding ketone groups. In some embodiments, hydrolysis consists of hydrolysis of all carboxyl derivative groups to provide the corresponding carboxylic acid groups, and hydrolysis of all ketal groups to provide the corresponding ketone groups.

In some embodiments, the present disclosure provides compositions which comprises one or more TCA cycle acid moieties, and one or more carboxylic acid moieties, wherein each TCA cycle acid moiety is independently a TCA cycle acid or a salt thereof, or a structural unit which, upon hydrolysis of the composition, is converted into a TCA cycle acid or a salt thereof; and each carboxylic acid moiety is independently a carboxylic acid or a salt thereof, or a structural unit which, upon hydrolysis of the composition, is converted into a carboxylic acid. In some embodiments, a TCA cycle acid moiety is independently a TCA cycle acid or a salt thereof. In some embodiments, TCA cycle acid moiety is a structural unit which, upon hydrolysis of the composition, is converted into a TCA cycle acid or a salt thereof. In some embodiments, a carboxylic acid moiety is a carboxylic acid or a salt thereof. In some embodiments, a carboxylic acid moiety is a structural unit which, upon hydrolysis of the composition, is converted into a carboxylic acid.

In some embodiments, a provided composition comprises a predetermined level of a first compound selected from a first group consisting of TCA cycle acids and salts, amides, esters, ketals, and anhydrides thereof; and a second compound selected from a second group consisting of carboxylic acids and salts, amides, esters, ketals, and anhydrides thereof.

In some embodiments, the present disclosure provides a composition, which when optionally fully hydrolyzed, provides a predetermined level of (a) a TCA cycle acid or salt thereof; and (b) a carboxylic acid or salt thereof. In some embodiments, the present disclosure provides a composition, which when optionally fully hydrolyzed, provides a predetermined level of (a) succinic cycle acid or a salt thereof; and (b) a non-TCA cycle carboxylic acid or a salt thereof. In some embodiments, a non-TCA cycle carboxylic acid can be metabolized to provide one or more ketone bodies, acetyl-CoA and/or propionyl-CoA in a subject. In some embodiments, a non-TCA cycle carboxylic acid can be metabolized to provide one or more ketone bodies in a subject. In some embodiments, a non-TCA cycle carboxylic acid can be metabolized to provide acetyl-CoA in a subject. In some embodiments, a non-TCA cycle carboxylic acid can be metabolized to provide propionyl-CoA in a subject. In some embodiments, hydrolysis comprises hydrolysis of all carboxyl derivative groups to provide the corresponding carboxylic acid groups, and hydrolysis of all ketal groups to provide the corresponding ketone groups. In some embodiments, hydrolysis consists of hydrolysis of all carboxyl derivative groups to provide the corresponding carboxylic acid groups, and hydrolysis of all ketal groups to provide the corresponding ketone groups.

In some embodiments, a provide composition is a pharmaceutical composition, further comprising a pharmaceutically acceptable carrier.

In some embodiments, a provided composition comprises a provided compound. e.g., a provided combination compound. In some embodiments, a provided composition is a pharmaceutical composition comprising a provided compound. e.g., a provided combination compound. In some embodiments, a provided composition is a pharmaceutical composition comprising an effective amount of a TCA cycle acid moiety, and an effective amount of a ketone body moiety, and a pharmaceutically acceptable carrier. In some embodiments, a provided composition is a pharmaceutical composition comprising an effective amount of a succinic acid moiety, and an effective amount of a beta-hydroxybutyric acid moiety, and a pharmaceutically acceptable carrier.

In some embodiments, provided technologies, e.g., compounds, compositions, methods, etc., comprise a predetermined level of a TCA cycle acid moiety and a ketone body moiety. In some embodiments, a predetermined level is a predetermine amount. In some embodiments, a provided level is a predetermined ratio. In some embodiments, a ratio is a molar ratio. In some embodiments, a predetermined level is a predetermined molar ratio between a TCA cycle acid moiety and a ketone body moiety. In some embodiments, all TCA cycle acid moieties and ketone body moieties have predetermined levels. In some embodiments, molar ratio between a TCA cycle acid moiety and a ketone body moiety is pre-determined. In some embodiments, molar ratio between the total of all TCA cycle acid moieties and the total of all ketone body moieties, is between about 100:1 and about 1:100. In some embodiments, a molar ratio is between about 100:1, 90:1, 80:1, 70:1, 60:1, 50:1, 40:1, 30:1, 20:1, 10:1, 9:1, 8:1, 7:1, 6:1, 5:1, 4:1, 3:1, 2:1, 1.5:1 or 1:1 and about 1:1.5, 1:2, 1:3, 1:4, 1:5, 1:6, 1:7, 1:8, 1:9, 1:10, 1:15, 1:20, 1:30, 1:40, 1:50, 1:60, 1:70, 1:80, 1:90, 1:100. In some embodiments, a molar ratio is about 5:1. In some embodiments, a molar ratio is about 4:1. In some embodiments, a molar ratio is about 3:1. In some embodiments, a molar ratio is about 2:1. In some embodiments, a molar ratio is about 1.5:1. In some embodiments, a molar ratio is about 1:1. In some embodiments, a molar ratio is about 1:1.5. In some embodiments, a molar ratio is about 1:2. In some embodiments, a molar ratio is about 1:3. In some embodiments, a molar ratio is about 1:4. In some embodiments, a molar ratio is about 1:5.

In some embodiments, a provided composition comprises a provided compound. e.g., a provided combination compound. In some embodiments, a provided composition is a pharmaceutical composition comprising a provided compound. e.g., a provided combination compound. In some embodiments, a provided composition is a pharmaceutical composition comprising an effective amount of a TCA cycle acid moiety, and an effective amount of a carboxylic acid moiety, and a pharmaceutically acceptable carrier. In some embodiments, a provided composition is a pharmaceutical composition comprising an effective amount of a succinic acid moiety, and an effective amount of a carboxylic acid moiety what can be metabolized in a subject to provide beta-hydroxybutyric acid or a salt thereof, and a pharmaceutically acceptable carrier.

In some embodiments, provided technologies, e.g., compounds, compositions, methods, etc., comprise a predetermined level of a TCA cycle acid moiety and a carboxylic acid (e.g., R'—C(O)OH) moiety. In some embodiments, a predetermined level is a predetermine amount. In some embodiments, a provided level is a predetermined ratio. In some embodiments, a ratio is a molar ratio. In some embodiments, a predetermined level is a predetermined molar ratio between a TCA cycle acid moiety and a carboxylic acid moiety. In some embodiments, all TCA cycle acid moieties and carboxylic acid moieties have predetermined levels. In some embodiments, molar ratio between a TCA cycle acid moiety and a carboxylic acid moiety is pre-determined. In some embodiments, molar ratio between the total of all TCA cycle acid moieties and the total of all carboxylic acid moieties, is between about 100:1 and about 1:100. In some embodiments, a molar ratio is between about 100:1, 90:1, 80:1, 70:1, 60:1, 50:1, 40:1, 30:1, 20:1, 10:1, 9:1, 8:1, 7:1, 6:1, 5:1, 4:1, 3:1, 2:1, 1.5:1 or 1:1 and about 1:1.5, 1:2, 1:3, 1:4, 1:5, 1:6, 1:7, 1:8, 1:9, 1:10, 1:15, 1:20, 1:30, 1:40, 1:50, 1:60, 1:70, 1:80, 1:90, 1:100. In some embodiments, a molar ratio is about 5:1. In some embodiments, a molar ratio is about 4:1. In some embodiments, a molar ratio is about 3:1. In some embodiments, a molar ratio is about 2:1. In some embodiments, a molar ratio is about 1.5:1. In some embodiments, a molar ratio is about 1:1. In some embodiments, a molar ratio is about 1:1.5. In some embodiments, a molar ratio is about 1:2. In some embodiments, a molar ratio is about 1:3. In some embodiments, a molar ratio is about 1:4. In some embodiments, a molar ratio is about 1:5.

Those skilled in the art will appreciate that a variety of suitable methods might be utilized in accordance with the present disclosure to prepare provided compounds and compositions. For example, many technologies are available and widely practiced in the art to prepare esters from alcohols and acids, for example, those using acidic or basic conditions and/or various activation methods and/or condensing reagent, including but not limited to those described in Greene, T. W.; Wuts, P. G. M. Protective Groups in Organic Synthesis, 2nd ed.; Wiley: New York, 1991.

Carboxylic Acids

As described herein, various carboxylic acids and carboxylic acid moieties may be used in provided technologies. In some embodiments, a carboxylic acid has the structure of R—C(O)OH. In some embodiments, a carboxylic acid moiety has the structure of R—C(O)O—. In some embodiments, a carboxylic acid moiety has the structure of R—C(O)—. In some embodiments, a carboxylic acid has the structure of R'—C(O)OH. In some embodiments, a carboxylic acid moiety has the structure of R'—C(O)O—. In some embodiments, a carboxylic acid moiety has the structure of R'—C(O)—.

In some embodiments, a carboxylic acid may be a TCA cycle acid. In some embodiments, a carboxylic acid, e.g., R'—C(O)OH is not a TCA cycle acid. In some embodiments, a provide compound comprises a TCA cycle acid moiety and a carboxylic acid moiety (e.g., R'—C(O)O— or R'—C(O)O—), wherein the carboxylic acid is different from the TCA cycle acid. In some embodiments, a provide compound comprises a TCA cycle acid moiety and a carboxylic acid moiety (e.g., R'—C(O)O— or R'—C(O)O—), wherein the carboxylic acid is a different TCA cycle acid. In some embodiments, a provide compound comprises a TCA cycle acid moiety and a carboxylic acid moiety (e.g., R'—C(O)O— or R'—C(O)O—), wherein the carboxylic acid is a not a TCA cycle acid.

In some embodiments, a carboxylic acid is or can be metabolized in a human being to provide one or more ketone bodies. In some embodiments, a carboxylic acid can be metabolized in a human being to provide one or more ketone bodies, acetyl-CoA and/or propionyl-CoA. In some embodiments, a carboxylic acid can be metabolized in a human being to provide one or more ketone bodies. In some embodiments, a carboxylic acid can be metabolized in a human being to provide acetyl-CoA. In some embodiments, a carboxylic acid can be metabolized in a human being to provide propionyl-CoA. In some embodiments, a provided compound, e.g., a combination compound, provides one or more ketone bodies after administered to a subject, in whom a provided compound is metabolized to provide a carboxylic acid or a salt thereof (e.g., through ester hydrolysis to provide R'—C(O)OH or a salt thereof), and the carboxylic acid or a salt thereof is metabolized to provide one or more ketone bodies (in acid and/or salt forms). In some embodiments, a provided compound, e.g., a combination compound, provides acetyl-CoA after administered to a subject, in whom a provided compound is metabolized to provide a carboxylic acid or a salt thereof (e.g., through ester hydrolysis to provide R'—C(O)OH or a salt thereof), and the carboxylic acid or a salt thereof is metabolized to provide acetyl-CoA. In some embodiments, a provided compound, e.g., a combination compound, provides propionyl-CoA after administered to a subject, in whom a provided compound is metabolized to provide a carboxylic acid or a salt thereof (e.g., through ester hydrolysis to provide R'—C(O)OH or a salt thereof), and the carboxylic acid or a salt thereof is metabolized to provide propionyl-CoA.

In some embodiments, R' is $C_1$-$C_{20}$ aliphatic wherein one or more —$CH_2$— units are independently and optionally replaced with —O—, —C(O)—, —CH(OH)—, or —C(O)O—. In some embodiments, R' is $C_1$-$C_{20}$ aliphatic wherein one or more —$CH_2$— units are independently and optionally replaced with —O—, —C(O)—, or —C(O)O—. In some embodiments, R' is $C_1$-$C_{20}$ aliphatic wherein one or more —$CH_2$— units are independently and optionally replaced with —C(O)—. In some embodiments, R' is $C_1$-$C_{20}$ aliphatic wherein one or more —$CH_2$— units are independently and optionally replaced with —C(O)O—.

In some embodiments, R' is $C_1$-$C_{20}$ aliphatic. In some embodiments, R' is $C_1$ aliphatic. In some embodiments, R' is $C_2$ aliphatic. In some embodiments, R' is $C_3$ aliphatic. In some embodiments, R' is $C_4$ aliphatic. In some embodiments, R' is $C_5$ aliphatic. In some embodiments, R' is $C_6$ aliphatic. In some embodiments, R' is $C_7$ aliphatic. In some embodiments, R' is $C_8$ aliphatic. In some embodiments, R' is $C_9$ aliphatic. In some embodiments, R' is $C_{10}$ aliphatic. In some embodiments, R' is $C_{11}$ aliphatic. In some embodiments, R' is $C_{12}$ aliphatic. In some embodiments, R' is $C_{13}$ aliphatic. In some embodiments, R' is $C_{14}$ aliphatic. In some embodiments, R' is $C_{15}$ aliphatic. In some embodiments, R' is $C_{16}$ aliphatic. In some embodiments, R' is $C_{17}$ aliphatic. In some embodiments, R' is Cis aliphatic. In some embodiments, R' is $C_{19}$ aliphatic. In some embodiments, R' is $C_{20}$ aliphatic.

In some embodiments, R' is $C_3$-$C_{20}$ linear aliphatic. $C_3$ linear aliphatic. In some embodiments, R' is $C_4$ linear aliphatic. In some embodiments, R' is $C_5$ linear aliphatic. In some embodiments, R' is $C_6$ linear aliphatic. In some embodiments, R' is $C_7$ linear aliphatic. In some embodiments, R' is $C_8$ linear aliphatic. In some embodiments, R' is $C_9$ linear aliphatic. In some embodiments, R' is $C_{10}$ linear aliphatic. In some embodiments, R' is $C_{11}$ linear aliphatic. In some embodiments, R' is $C_{12}$ linear aliphatic. In some embodiments, R' is $C_{13}$ linear aliphatic. In some embodiments, R' is $C_{14}$ linear aliphatic. In some embodiments, R' is $C_{15}$ linear aliphatic. In some embodiments, R' is $C_{16}$ linear aliphatic. In some embodiments, R' is $C_{17}$ linear aliphatic. In some embodiments, R' is $C_{18}$ linear aliphatic. In some embodiments, R' is $C_{19}$ linear aliphatic. In some embodiments, R' is $C_{20}$ linear aliphatic.

In some embodiments, R' is $C_1$-$C_{20}$ alkyl. In some embodiments, R' is $C_1$ alkyl. In some embodiments, R' is $C_2$ alkyl. In some embodiments, R' is $C_3$ alkyl. In some embodiments, R' is $C_4$ alkyl. In some embodiments, R' is $C_5$ alkyl. In some embodiments, R' is $C_6$ alkyl. In some embodiments, R' is $C_7$ alkyl. In some embodiments, R' is $C_8$ alkyl. In some embodiments, R' is $C_9$ alkyl. In some embodiments, R' is $C_{10}$ alkyl. In some embodiments, R' is $C_{11}$ alkyl. In some embodiments, R' is $C_{12}$ alkyl. In some embodiments, R' is $C_{13}$ alkyl. In some embodiments, R' is $C_{14}$ alkyl. In some embodiments, R' is Cis alkyl. In some embodiments, R' is $C_{16}$ alkyl. In some embodiments, R' is $C_{17}$ alkyl. In some embodiments, R' is $C_{18}$ alkyl. In some embodiments, R' is $C_{19}$ alkyl. In some embodiments, R' is $C_{20}$ alkyl.

In some embodiments, R' is $C_3$-$C_{20}$ linear alkyl. $C_3$ linear alkyl. In some embodiments, R' is $C_4$ linear alkyl. In some embodiments, R' is $C_5$ linear alkyl. In some embodiments, R' is $C_6$ linear alkyl. In some embodiments, R' is $C_7$ linear alkyl. In some embodiments, R' is $C_8$ linear alkyl. In some embodiments, R' is $C_9$ linear alkyl. In some embodiments, R' is $C_{10}$ linear alkyl. In some embodiments, R' is $C_{11}$ linear alkyl. In some embodiments, R' is $C_{12}$ linear alkyl. In some embodiments, R' is $C_{13}$ linear alkyl. In some embodiments, R' is $C_{14}$ linear alkyl. In some embodiments, R' is $C_{15}$ linear alkyl. In some embodiments, R' is $C_{16}$ linear alkyl. In some embodiments, R' is $C_{17}$ linear alkyl. In some embodiments, R' is $C_{18}$ linear alkyl. In some embodiments, R' is $C_{19}$ linear alkyl. In some embodiments, R' is $C_{20}$ linear alkyl.

In some embodiments, R'—C(O)OH is a carboxylic acid of even carbon numbers. In some embodiments, R'—C(O)OH is a carboxylic acid of odd carbon numbers. In some embodiments, R'—C(O)OH is a carboxylic acid of even carbon numbers and can be metabolized to provided acetyl-CoA in a subject. In some embodiments, R'—C(O)OH is a carboxylic acid of odd carbon numbers and can be metabolized to provided acetyl-CoA in a subject. In some embodiments, R'—C(O)OH is a carboxylic acid of odd carbon numbers and can be metabolized to provided acetyl-CoA and propionyl-CoA in a subject.

In some embodiments, R'—C(O)OH is $CH_3COOH$. In some embodiments, R'—C(O)OH is $CH_3CH(OH)CH_2COOH$. In some embodiments, R'—C(O)OH is (D)-$CH_3CH(OH)CH_2COOH$. In some embodiments, R'—C(O)OH is $CH_3(CH_2)_4COOH$. In some embodiments, R'—C(O)OH is $CH_3(CH_2)_5COOH$. In some embodiments, R'—C(O)OH is $CH_3(CH_2)_6COOH$. In some embodiments, R'—C(O)OH is $CH_3(CH_2)_{14}COOH$. In some embodiments, R'—C(O)OH is (Z, Z)—$CH_3(CH_2)_4CH=CHCH_2CH=CH(CH_2)_4COOH$. In some embodiments, R'—C(O)OH is (Z, Z)—$CH_3(CH_2)_3CH=CHCH_2CH=CH(CH_2)_7COOH$. In some embodiments, R'—C(O)OH is (Z, Z)—$CH_3(CH_2)_4CH=CHCH_2CH=CH(CH_2)_7COOH$. In some embodiments, R'—C(O)OH is (Z, Z, Z, Z, Z)—$CH_3CH_2CH=CHCH_2CH=CHCH_2CH=CHCH_2CH=CHCH_2CH=CHCH_2(CH_2)_2COOH$.

In some embodiments, R' is $CH_3$—. In some embodiments, R' is $CH_3CH(OH)CH_2$—. In some embodiments, R' is (D)-$CH_3CH(OH)CH_2$—. In some embodiments, R' is $CH_3(CH_2)_4$—. In some embodiments, R' is $CH_3(CH_2)_5$—. In some embodiments, R' is $CH_3(CH_2)_6$—. In some embodiments, R' is $CH_3(CH_2)_{14}$—. In some embodiments, R' is (Z, Z)—$CH_3(CH_2)_4CH=CHCH_2CH=CH(CH_2)_4$—. In some embodiments, R' is (Z, Z)—$CH_3(CH_2)_3CH=CHCH_2CH=CH(CH_2)_7$—. In some embodiments, R' is (Z, Z)—$CH_3(CH_2)_4CH=CHCH_2CH=CH(CH_2)_7$—. In some embodiments, R' is (Z, Z, Z, Z, Z)—$CH_3CH_2CH=CHCH_2CH=CHCH_2CH=CHCH_2CH=CHCH_2CH=CHCH_2(CH_2)_2$—.

In some embodiments, a provided compound has at least one R' group. In some embodiments, a provided compound has at least two R' groups. In some embodiments, a provided compound has at least three R' groups. In some embodiments, a provided compound has at least four R' groups.

In some embodiments, a provided compound contains one or more R' groups having the same structure. In some embodiments, a provided compound contains one or more R' groups, wherein at least one R' group has a different structure than another R' group.

In some embodiments, a provided compound has at least one R'—C(O)— group. In some embodiments, a provided compound has at least two R'—C(O)— groups. In some embodiments, a provided compound has at least three R'—C(O)— groups. In some embodiments, a provided compound has at least four R'—C(O)— groups.

In some embodiments, a provided compound contains one or more R'—C(O)— groups having the same structure. In some embodiments, a provided compound contains one or more R'—C(O)— groups, wherein at least one R'—C(O)— group has a different structure than another R'—C(O)— group.

In some embodiments, a provided compound has at least one R'—C(O)O— group. In some embodiments, a provided compound has at least two R'—C(O)O— groups. In some embodiments, a provided compound has at least three R'—C(O)O— groups. In some embodiments, a provided compound has at least four R'—C(O)O— groups.

In some embodiments, a provided compound contains one or more R'—C(O)O— groups having the same structure. In some embodiments, a provided compound contains one or more R'—C(O)O— groups, wherein at least one R'—C(O)O— group has a different structure than another R'—C(O)O— group.

In some embodiments, a provided compound is selected from Table 1:

| Compound | No. |
|---|---|
| 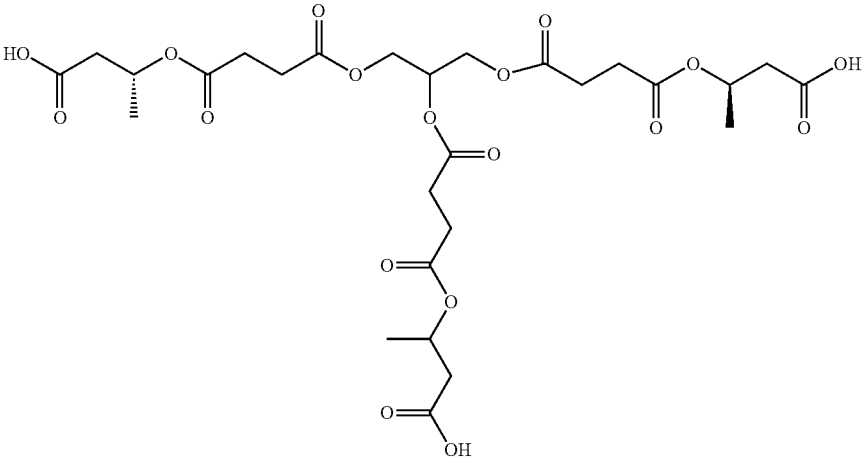 [SMILES: CC(CC(=O)O)OC(=O)CCC(=O)OC(COC(=O)CCC(=O)O[C@H](C)CC(=O)O)COC(=O)CCC(=O)O[C@H](C)CC(=O)O] | I-1 |
| 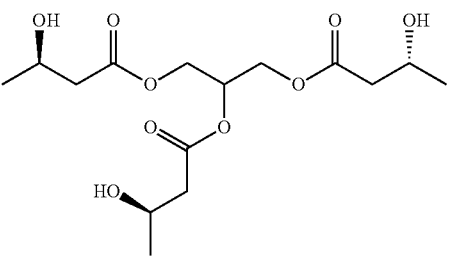 [SMILES: C[C@@H](O)CC(=O)OCC(COC(=O)C[C@@H](C)O)OC(=O)C[C@@H](C)O] | I-2 |

-continued

| Compound | No. |
|---|---|
| | I-3 |
| | I-4 |
| | I-5 |
| | I-6 |
| | I-7 |

| Compound | No. |
|---|---|
| | I-8 |
| | I-9 |
| | I-10 |
| | I-11 |
| | I-12 |
| | I-13 |

-continued
| Compound | No. |
|---|---|
| 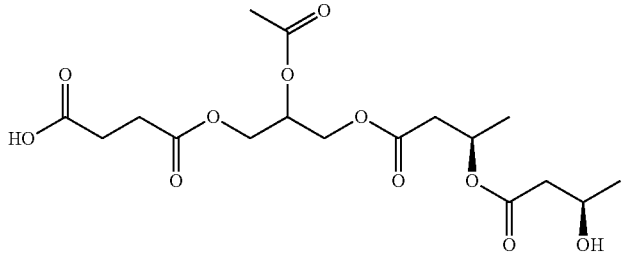 [SMILES: CC(=O)OC(COC(=O)CCC(=O)O)COC(=O)C[C@@H](C)OC(=O)C[C@@H](C)O] | I-14 |
| 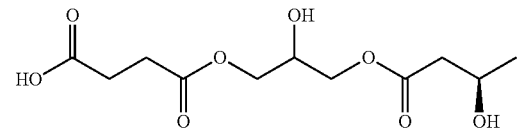 [SMILES: C[C@@H](O)CC(=O)OCC(O)COC(=O)CCC(=O)O] | I-15 |
| 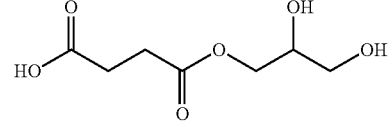 [SMILES: O=C(O)CCC(=O)OCC(O)CO] | I-16 |
| 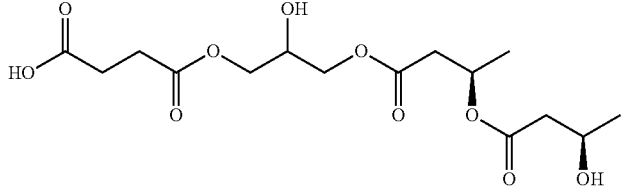 [SMILES: C[C@H](CC(=O)OCC(O)COC(=O)CCC(=O)O)OC(=O)C[C@@H](C)O] | I-17 |
| 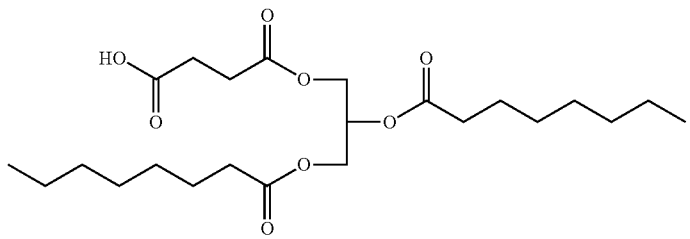 [SMILES: CCCCCCCC(=O)OCC(COC(=O)CCC(=O)O)OC(=O)CCCCCCC] | I-18 |
| 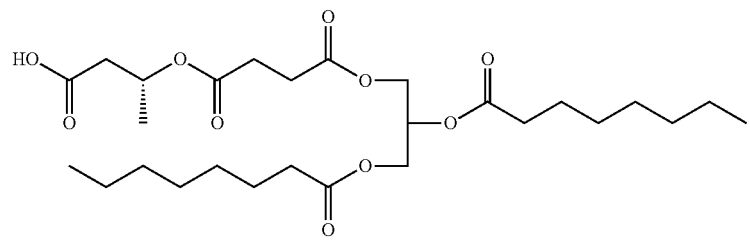 [SMILES: CCCCCCCC(=O)OCC(COC(=O)CCC(=O)O[C@H](C)CC(=O)O)OC(=O)CCCCCCC] | I-19 |
| 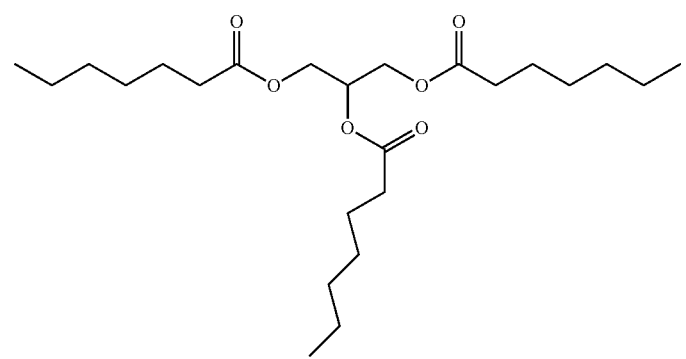 [SMILES: CCCCCCC(=O)OCC(COC(=O)CCCCCC)OC(=O)CCCCCC] | I-20 |

| Compound | No. |
|---|---|
| | I-21 |
| | I-22 |
| | I-23 |
| | I-24 |
| | I-25 |

| Compound | No. |
|---|---|
| 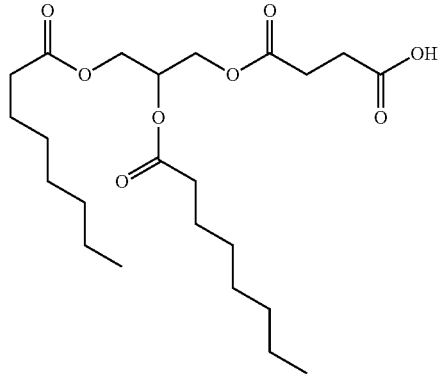 [SMILES: CCCCCCCC(=O)OCC(COC(=O)CCC(=O)O)OC(=O)CCCCCCC] | I-26 |
| 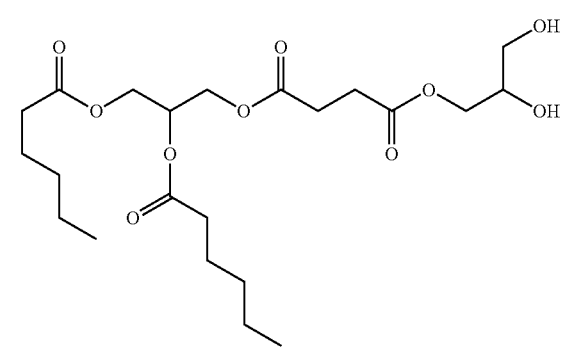 [SMILES: CCCCCC(=O)OCC(COC(=O)CCC(=O)OCC(O)CO)OC(=O)CCCCC] | I-27 |
| 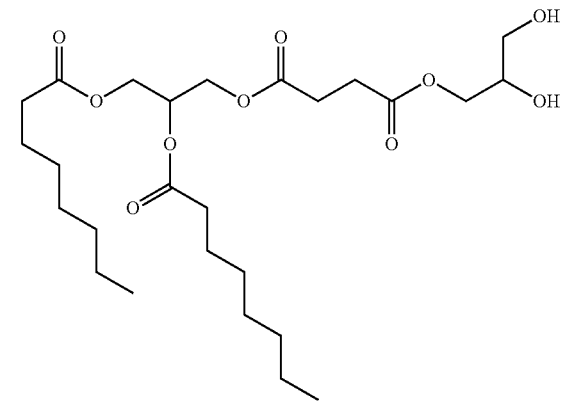 [SMILES: CCCCCCCC(=O)OCC(COC(=O)CCC(=O)OCC(O)CO)OC(=O)CCCCCCC] | I-28 |
| 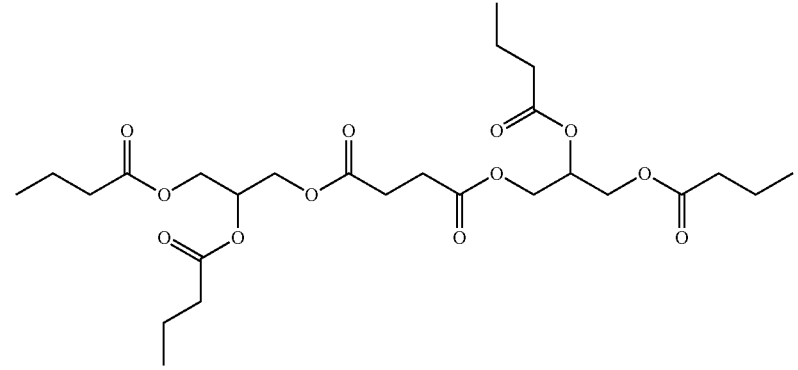 [SMILES: CCCC(=O)OCC(COC(=O)CCC(=O)OCC(COC(=O)CCC)OC(=O)CCC)OC(=O)CCC] | I-29 |

| Compound | No. |
|---|---|
| 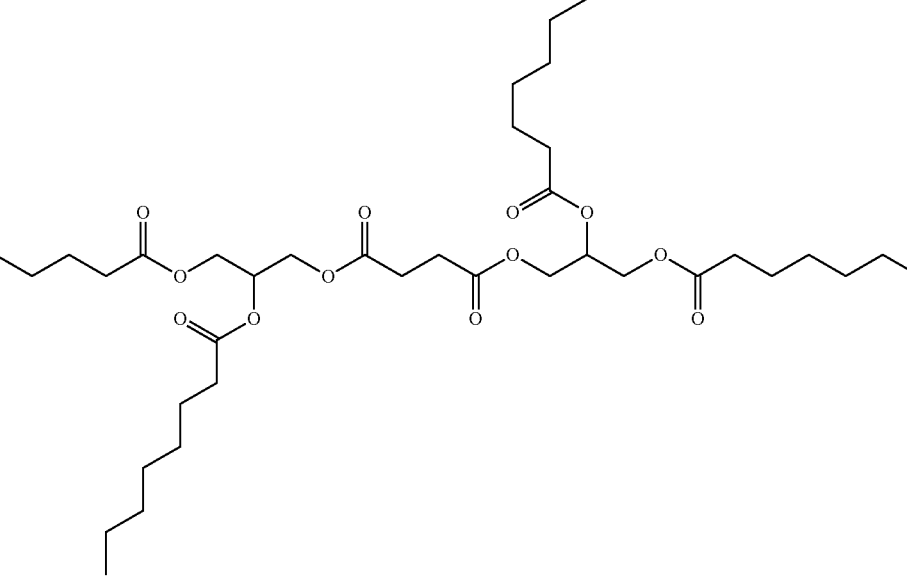 | I-30 |
| 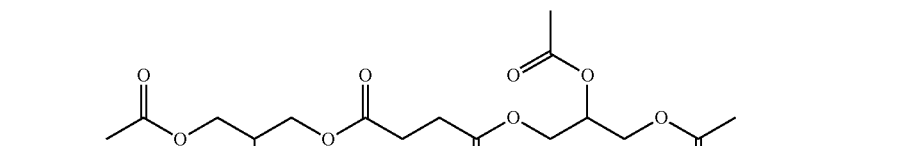 | I-31 | or a pharmaceutically acceptable salt thereof. In some embodiments, a provided compound is selected from I-1 to I-15, I-17 to I-19, I-21, and I-23 to I-31, or a pharmaceutically acceptable salt thereof. In some embodiments, a provided compound is I-1, I-8 to I-19, and I-21 to I-31, or a pharmaceutically acceptable salt thereof. In some embodiments, a provided compound is I-1, I-8 to I-19, and I-21 to I-30, or a pharmaceutically acceptable salt thereof. In some embodiments, a provided compound is I-1, I-8 to I-19, I-21, and I-23 to I-31, or a pharmaceutically acceptable salt thereof. In some embodiments, a provided compound is I-1, I-8 to I-19, I-21, and I-23 to I-30, or a pharmaceutically acceptable salt thereof. In some embodiments, a provided compound is I-1, I-8 to I-15, I-17 to I-19, I-21, and I-23 to I-31, or a pharmaceutically acceptable salt thereof. In some embodiments, a provided compound is I-1, I-8 to I-15, I-17 to I-19, I-21, and I-23 to I-30, or a pharmaceutically acceptable salt thereof. In some embodiments, a provided compound is I-1 or pharmaceutically acceptable salt thereof. In some embodiments, a provided compound is I-2 or pharmaceutically acceptable salt thereof. In some embodiments, a provided compound is I-3 or pharmaceutically acceptable salt thereof. In some embodiments, a provided compound is I-4 or pharmaceutically acceptable salt thereof. In some embodiments, a provided compound is I-5 or pharmaceutically acceptable salt thereof. In some embodiments, a provided compound is I-6 or pharmaceutically acceptable salt thereof. In some embodiments, a provided compound is I-7 or pharmaceutically acceptable salt thereof. In some embodiments, a provided compound is I-8 or pharmaceutically acceptable salt thereof. In some embodiments, a provided compound is I-9 or pharmaceutically acceptable salt thereof. In some embodiments, a provided compound is I-10 or pharmaceutically acceptable salt thereof. In some embodiments, a provided compound is I-11 or pharmaceutically acceptable salt thereof. In some embodiments, a provided compound is I-12 or pharmaceutically acceptable salt thereof. In some embodiments, a provided compound is I-13 or pharmaceutically acceptable salt thereof. In some embodiments, a provided compound is I-14 or pharmaceutically acceptable salt thereof. In some embodiments, a provided compound is I-15 or pharmaceutically acceptable salt thereof. In some embodiments, a provided compound is I-16 or pharmaceutically acceptable salt thereof. In some embodiments, a provided compound is I-17 or pharmaceutically acceptable salt thereof. In some embodiments, a provided compound is I-18 or pharmaceutically acceptable salt thereof. In some embodiments, a provided compound is I-19 or pharmaceutically acceptable salt thereof. In some embodiments, a provided compound is I-20 or pharmaceutically acceptable salt thereof. In some embodiments, a provided compound is I-21 or pharmaceutically acceptable salt thereof. In some embodiments, a provided compound is I-22 or pharmaceutically acceptable salt thereof. In some embodiments, a provided compound is I-23 or pharmaceutically acceptable salt thereof. In some embodiments, a provided compound is I-24 or pharmaceutically acceptable salt thereof. In some embodiments, a provided compound is I-25 or pharmaceutically acceptable salt thereof. In some embodiments, a provided compound is I-26 or pharmaceutically acceptable salt thereof. In some embodiments, a provided compound is I-27 or pharmaceutically acceptable salt thereof. In some embodiments, a provided compound is I-28 or pharmaceutically acceptable salt thereof. In some embodiments, a provided compound is I-29 or pharmaceutically acceptable salt thereof. In some embodiments, a provided compound is I-30 or pharmaceutically acceptable salt thereof. In some embodiments, a provided compound is I-31 or pharmaceutically acceptable salt thereof. In some embodiments, a provided compound is not a compound selected from any combination of I-1, I-2, I-2, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30 and I-31, e.g., (I-1, I-2, I-2, I-4, I-5, I-6, I-7, I-8, I-9, I-10, I-11, I- 12, I-13, I-14, I-15, I-16, I-17, I-18, I-19, I-20, I-21, I-22, I-23, I-24, I-25, I-26, I-27, I-28, I-29, I-30, and I-31), (I-1, I-2, I-2, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29 and I-30), (I-1, I-2, I-2, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, and I-28), (I-2, I-2, I-4, I-5, I-6, I-7, I-9, I-10, I-11, I-12, I-13, I-14, I-16, I-17, I-18, I-19, I-20, I-21, I-23, I-24, I-25, I-26, I-27, and I-28), etc., or a pharmaceutically acceptable salt thereof. In some embodiments, a provided compound is not a compound selected from I-1, I-2, I-2, I-4, I-5, I-6, I-7, I-8, I-9, I-10, I-11, I-12, I-13, I-14, I-15, I-16, I-17, I-18, I-19, I-20, I-21, I- 22, I-23, I-24, I-25, I-26, I-27, and I-28, or a pharmaceutically acceptable salt thereof.

In some embodiments, a provided compound has a purity of no less than about 50%, 60%, 70%, 80%, 85%, 90%, 91%, 92%, 93%, 94%, 95%, 96%, 97%, 98%, 99%, 99.5%, or 99.9%. In some embodiments, the purity is no less than about 50% In some embodiments, the purity is no less than about 60% In some embodiments, the purity is no less than about 70% In some embodiments, the purity is no less than about 80% In some embodiments, the purity is no less than about 85% In some embodiments, the purity is no less than about 90% In some embodiments, the purity is no less than about 91% In some embodiments, the purity is no less than about 92% In some embodiments, the purity is no less than about 93% In some embodiments, the purity is no less than about 94% In some embodiments, the purity is no less than about 95% In some embodiments, the purity is no less than about 96% In some embodiments, the purity is no less than about 97% In some embodiments, the purity is no less than about 98% In some embodiments, the purity is no less than about 99% In some embodiments, the purity is no less than about 99.5% In some embodiments, the purity is no less than about or 99.9%.

Compositions

In some embodiments, the present disclosure provides pharmaceutical compositions for use in provided combination therapy. In some embodiments, a provided pharmaceutical composition comprises a therapeutically effective amount of a provided combination, and at least one pharmaceutically acceptable inactive ingredient selected from pharmaceutically acceptable diluents, pharmaceutically acceptable excipients, and pharmaceutically acceptable carriers. In some embodiments, the pharmaceutical composition is formulated for intravenous injection, oral administration, buccal administration, inhalation, nasal administration, topical administration, ophthalmic administration or otic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

Among other things, the present disclosure recognizes that properties of provided compounds and/or compositions, such as flow properties and/or taste, etc., are important for pharmaceutical formulations. For example, in some embodiments, a compound may be too viscous for formulation, and/or too unpalatable (e.g., bitter) for oral administration and/or good patient compliance. In some embodiments, provided technologies, for example, those with butyric acid and/or caprylic acid moieties, and/or without free succinic acid —COOH groups, and/or without free carboxylic acid and/or hydroxyl groups, such as compounds I-29 and I-30, were tested to have surprisingly good flow properties and taste for formulation. In some embodiments, provided compounds can be administered by direct oral administration. In some embodiments, provided compounds have suitable flow property and taste and can be administered by direct drinking by a subject. In some embodiments, viscosity of a provided liquid compound is no more than 0.9, 1, 2, 3, 4, 5, 6, 7, 8, 9, 10, 20, 30, 40, 50, 60, 70, 80, 90, 100, 200, 300, 400, 500, 600, 700, 800, 900, 1000, 1100, 1200, 1500 or 2000 cP at a temperature. In some embodiments, a temperature is 25° C. In some embodiments, a temperature is 20° C. In some embodiments, a temperature is room temperature. In some embodiments, the viscosity is no more than 1500 cP at a temperature. In some embodiments, the viscosity is no more than 1200 cP at a temperature. In some embodiments, the viscosity is no more than 1000 cP at a temperature. In some embodiments, the viscosity is no more than 900 cP at a temperature. In some embodiments, the viscosity is no more than 800 cP at a temperature. In some embodiments, the viscosity is no more than 700 cP at a temperature. In some embodiments, the viscosity is no more than 600 cP at a temperature. In some embodiments, the viscosity is no more than 500 cP at a temperature. In some embodiments, the viscosity is no more than 400 cP at a temperature. In some embodiments, the viscosity is no more than 300 cP at a temperature. In some embodiments, the viscosity is no more than 200 cP at a temperature. In some embodiments, the viscosity is no more than 100 cP at a temperature. In some embodiments, the viscosity is no more than 50 cP at a temperature. In some embodiments, the viscosity is no more than 40 cP at a temperature. In some embodiments, the viscosity is no more than 30 cP at a temperature. In some embodiments, the viscosity is no more than 20 cP at a temperature. In some embodiments, the viscosity is no more than 10 cP at a temperature. In some embodiments, the viscosity is no more than 9 cP at a temperature. In some embodiments, the viscosity is no more than 8 cP at a temperature. In some embodiments, the viscosity is no more than 7 cP at a temperature. In some embodiments, the viscosity is no more than 6 cP at a temperature. In some embodiments, the viscosity is no more than 5 cP at a temperature. In some embodiments, the viscosity is no more than 4 cP at a temperature. In some embodiments, the viscosity is no more than 3 cP at a temperature. In some embodiments, the viscosity is no more than 2 cP at a temperature. In some embodiments, the viscosity is no more than 1 cP at a temperature. In some embodiments, a temperature is 25° C. In some embodiments, a temperature is 20° C. In some embodiments, a temperature is room temperature. In some embodiments, provided compounds are less viscous than glycerol at a temperature, e.g., room temperature. In addition, certain compounds can be administered, e.g., by direct drinking, in large quantities. In some embodiments, such large quantities are necessary to provide enough TCA cycle intermediate replenishment to be effective. In some embodiments, a quantity is at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3, 3.5, 4 or 5 g/kg. In some embodiments, a quantity is at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3, 3.5, 4 or 5 g/kg per day. In some embodiments, a quantity is at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3, 3.5, 4 or 5 g/kg per single dose. In some embodiments, a quantity is at least 0.1 g/kg. In some embodiments, a quantity is at least 0.1 g/kg. In some embodiments, a quantity is at least 0.2 g/kg. In some embodiments, a quantity is at least 0.3 g/kg. In some embodiments, a quantity is at least 0.4 g/kg. In some embodiments, a quantity is at least 0.5 g/kg. In some embodiments, a quantity is at least 0.6 g/kg. In some embodiments, a quantity is at least 0.7 g/kg. In some embodiments, a quantity is at least 0.8 g/kg. In some embodiments, a quantity is at least 0.9 g/kg. In some embodiments, a quantity is at least 1 g/kg. In some embodiments, a quantity is at least 1.1 g/kg. In some embodiments, a quantity is at least 1.2 g/kg. In some embodiments, a quantity is at least 1.3 g/kg. In some embodiments, a quantity is at least 1.4 g/kg. In some embodiments, a quantity is at least 1.5 g/kg. In some embodiments, a quantity is at least 1.6 g/kg. In some embodiments, a quantity is at least 1.7 g/kg. In some embodiments, a quantity is at least 1.8 g/kg. In some embodiments, a quantity is at least 1.9 g/kg. In some embodiments, a quantity is at least 2 g/kg. In some embodiments, a quantity is at least 2.5 g/kg. In some embodiments, a quantity is at least 3 g/kg. In some embodiments, a quantity is at least 3.5 g/kg. In some embodiments, a quantity is at least 4 g/kg. In some embodiments, a quantity is at least 5 g/kg. In some embodiments, a quantity is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3, 3.5, 4 or 5 g/kg. In some embodiments, a quantity is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3, 3.5, 4 or 5 g/kg per day. In some embodiments, a quantity is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3, 3.5, 4 or 5 g/kg per single dose. In some embodiments, a quantity is about 0.1 g/kg. In some embodiments, a quantity is about 0.1 g/kg. In some embodiments, a quantity is about 0.2 g/kg. In some embodiments, a quantity is about 0.3 g/kg. In some embodiments, a quantity is about 0.4 g/kg. In some embodiments, a quantity is about 0.5 g/kg. In some embodiments, a quantity is about 0.6 g/kg. In some embodiments, a quantity is about 0.7 g/kg. In some embodiments, a quantity is about 0.8 g/kg. In some embodiments, a quantity is about 0.9 g/kg. In some embodiments, a quantity is about 1 g/kg. In some embodiments, a quantity is about 1.1 g/kg. In some embodiments, a quantity is about 1.2 g/kg. In some embodiments, a quantity is about 1.3 g/kg. In some embodiments, a quantity is about 1.4 g/kg. In some embodiments, a quantity is about 1.5 g/kg. In some embodiments, a quantity is about 1.6 g/kg. In some embodiments, a quantity is about 1.7 g/kg. In some embodiments, a quantity is about 1.8 g/kg. In some embodiments, a quantity is about 1.9 g/kg. In some embodiments, a quantity is about 2 g/kg. In some embodiments, a quantity is about 2.5 g/kg. In some embodiments, a quantity is about 3 g/kg. In some embodiments, a quantity is about 3.5 g/kg. In some embodiments, a quantity is about 4 g/kg. In some embodiments, a quantity is about 5 g/kg.

In some embodiments, the present disclosure provides a pharmaceutical composition comprising a provided combination compound or combination composition, in admixture with a pharmaceutically acceptable excipient.

In therapeutic and/or diagnostic applications, provide compounds can be formulated for a variety of modes of administration, including systemic and topical or localized administration. Techniques and formulations generally may be found in Remington, The Science and Practice of Pharmacy, (20th ed. 2000).

Provided compounds and compositions thereof are effective over a wide dosage range. For example, in the treatment of adult humans, dosages from about 0.01 to about 10000 mg, from about 0.01 to about 1000 mg, from about 0.5 to about 100 mg, from about 1 to about 50 mg per day, and from about 5 to about 100 mg per day are examples of dosages that may be used. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington, The Science and Practice of Pharmacy (20th ed. 2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

In some embodiments, pharmaceutically acceptable salts are metal salts. In some embodiments, pharmaceutically acceptable salts are alkaline metal salts. In some embodiments, pharmaceutically acceptable salts are alkaline earth metal salts. In some embodiments, a pharmaceutically acceptable salt is a lithium, sodium, potassium, magnesium, or calcium salt. In some embodiments, a pharmaceutically acceptable salt is a sodium salt.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington, The Science and Practice of Pharmacy (20th ed. 2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, provided agents may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate provided compounds or compositions into dosages suitable for systemic administration is within the scope of the disclosure. With proper choice of carrier and suitable manufacturing practice, the compositions of the present disclosure, in particular, those formulated as solutions, may be administered parenterally, such as by intravenous injection.

The compounds can be formulated readily using pharmaceutically acceptable carriers well known in the art into dosages suitable for oral administration. Such carriers enable provided compounds and compositions to be formulated as tablets, pills, capsules, liquids, gels, syrups, slurries, suspensions and the like, for oral ingestion by a subject (e.g., patient) to be treated.

For nasal or inhalation delivery, provided compounds or compositions may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

In certain embodiments, provided compounds and compositions are delivered to the CNS. In certain embodiments, provided compounds and compositions are delivered to the cerebrospinal fluid. In certain embodiments, provided compounds and compositions are administered to the brain parenchyma. In certain embodiments, provided compounds and compositions are delivered to an animal/subject by intrathecal administration, or intracerebroventricular administration. Broad distribution of provided compounds and compositions, described herein, within the central nervous system may be achieved with intraparenchymal administration, intrathecal administration, or intracerebroventricular administration.

In certain embodiments, parenteral administration is by injection, by, e.g., a syringe, a pump, etc. In certain embodiments, the injection is a bolus injection. In certain embodiments, the injection is administered directly to a tissue, such as striatum, caudate, cortex, hippocampus and cerebellum.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

In some embodiments, cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with provided compounds or compositions. For example, chemotherapeutic agents or other anti-proliferative agents may be combined with provided compounds or compositions to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Identification and/or Characterization of Useful Combination Compositions and/or Compounds Those skilled in the art, reading the present disclosure, will appreciate that a variety of assay systems are available for identifying, characterizing, and/or selecting for particular application one or more combination compositions or compounds as described herein.

To give but a few examples, in some embodiments, a combination composition or compound may be characterized in that it shows activity, for example, in a mouse model of propionic acidemia (for example, as described by Miyazaki et al in *J. Biol Chem.* 276:35995, epub Jul. 18, 2001), of methylamonic acidemia (see, for example, Peters et al *PLoS One* 7:e40608, epub Jul. 9, 2012) and/or of one or more long chain fatty acid oxidation disorders (see, for example, Spiekerkoetter et al., *J. Inherit Metab Dis.* 33:539, Jun. 8, 2010).

Uses

Various diseases, disorders, and/or conditions may be related to abnormal metabolism, and can be treated and/or benefit from provided technologies. In some embodiments, the present disclosure provides methods comprising administering to a subject suffering from or susceptible to a disease, disorder or condition a pharmaceutically effective amount of a provided compound or composition. In some embodiments, a disease is related to abnormal metabolism.

In some embodiments, a disease, disorder or condition is or comprises an energetic disorder. In some embodiments, a disease, disorder or condition is refractory epilepsy. In some embodiments, a disease, disorder or condition is propionic acidemia (PA). In some embodiments, a disease, disorder or condition is methylmalonic acidemia (MMA). In some embodiments, a disease, disorder or condition is a long chain fatty acid oxidation disorder. In some embodiments, a disease, disorder or condition is succinyl-CoA lyase deficiency. In some embodiments, a disease, disorder or condition is pyruvate carboxylase deficiency.

In some embodiments, a disease, disorder or condition is mitochondrial respiratory chain deficiencies. In some embodiments, a disease, disorder or condition is glutaric acidemia type 1. In some embodiments, a disease, disorder or condition is glutaric acidemia type 2.

In some embodiments, a disease, disorder or condition is a neurologic disease, disorder or condition. In some embodiments, a disease, disorder or condition is Huntington's disease. In some embodiments, a disease, disorder or condition is Parkinson's disease. In some embodiments, a the disease, disorder or condition is Alzheimer's disease.

In some embodiments, a disease, disorder or condition is cancer.

In some embodiments, a disease, disorder or condition is a pain or fatigue disease. In some embodiments, a disease, disorder or condition is fibromyalgia. In some embodiments, a disease, disorder or condition is chronic fatigue syndrome.

In some embodiments, a disease, disorder or condition is muscular dystrophy. In some embodiments, a disease, disorder or condition is Duchenne's muscular dystrophy. In some embodiments, a disease, disorder or condition is Becker's muscular dystrophy.

In some embodiments, a disease, disorder or condition is a mitochondrial myopathy. In some embodiments, a disease, disorder or condition is mitochondrial encephalomyopathy, lactic acidosis, and stroke-like syndrome (MELAS). In some embodiments, a disease, disorder or condition is myoclonic epilepsy and ragged-red fibers (MERRF).

In some embodiments, a disease, disorder or condition is a mitochondrial associated disease. In some embodiments, a disease, disorder or condition is related to POLG. In some embodiments, a disease, disorder or condition is related to POLG mutation.

Those skilled in the art will be aware of a various strategies for identifying appropriate subjects suffering from and/or susceptible to one or more such diseases, disorders, and/or conditions, and for delivering combination therapy as described herein to them.

In some embodiments, provided combination therapy may be formulated for oral administration and may be administered orally. In some embodiments, provided combination therapy may be administered to adult subjects. In some embodiments, provided combination therapy may be administered to pediatric subjects. In some embodiments, provided combination therapy may be administered according to a regimen demonstrated to be effective in a population of such subjects, suffering from or susceptible to a disease, disorder, or condition (e.g., a metabolic disease, disorder or condition) as described herein.

Among other things, the present disclosure provides the following example embodiments:

1. A compound having the structure of formula I:

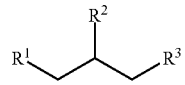

I or a salt thereof, wherein:
each of $R^1$, $R^2$ and $R^3$ is independently —H, —OH, R', or —OC(O)R, or may be independently and optionally taken together with a hydrogen atom on the carbon atom to which it is attached to form an oxo group;

each R and R' is independently linear or branched $C_1$-$C_{100}$ aliphatic wherein one or more —$CH_2$— units are independently and optionally replaced with —O—, —C(O)—, —CH(OH)— or —C(O)O—, and any two or more R or R' groups may be linked by one or more linear or branched, bivalent or polyvalent, $C_1$-$C_{100}$ hydrocarbon group wherein one or more —$CH_2$— units are independently and optionally replaced with —O—, —C(O)—, —CH(OH)— or —C(O)O—;

at least one of $R^1$, $R^2$ and $R^3$ is —OC(O)R; and wherein when each ester group of the compound of formula I is hydrolyzed, each hydrolysis product is independently a compound selected from (i) a TCA cycle acid or a salt thereof, (ii) a compound that is, contains, or can be metabolized by a human body to contain a ketone body or ketone body moiety, or a salt thereof, and (iii) an alcohol compound.

2. A compound having the structure of formula I:

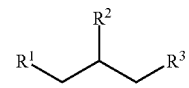

I or a salt thereof, wherein:
each of $R^1$, $R^2$ and $R^3$ is independently —H, —OH, R', or —OC(O)R;

each R and R' is independently linear or branched $C_1$-$C_{100}$ aliphatic wherein one or more —$CH_2$— units are independently and optionally replaced with —O—, —C(O)—, —CH(OH)— or —C(O)O—, and any two R or R' groups may be linked by one or more linear or branched, bivalent or polyvalent, $C_1$-$C_{100}$ hydrocarbon group wherein one or more —$CH_2$— units are independently and optionally replaced with —O—, —C(O)—, —CH(OH)— or —C(O)O—;

at least one of $R^1$, $R^2$ and $R^3$ is —OC(O)R; and wherein when each ester group of the compound of formula I is hydrolyzed, each of the hydrolysis product is independently a compound selected from a TCA cycle acid or a salt thereof, or a ketone body or a salt thereof, and glycerol;

at least one hydrolysis product is a TCA cycle acid; and at least one hydrolysis product is a ketone body.

3. A compound having the structure of formula I:

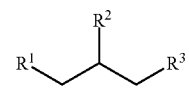

I or a salt thereof, wherein:
each of $R^1$, $R^2$ and $R^3$ is independently —H, —OH, R', or —OC(O)R;

each R and R' is independently linear or branched $C_1$-$C_{100}$ aliphatic wherein one or more —$CH_2$— units are independently replaced with —O—, —C(O)—, —CH(OH)— or —C(O)O—, and any two R or R' groups may be linked by one or more linear or branched, bivalent or polyvalent, $C_1$-$C_{100}$ hydrocarbon group wherein one or more —$CH_2$— units are independently replaced with —O—, —C(O)—, —CH(OH)— or —C(O)O—;

at least one of $R^1$, $R^2$ and $R^3$ is —OC(O)R; and wherein when each ester group of the compound of formula I is hydrolyzed, each of the hydrolysis product is independently a compound selected from a TCA cycle acid or a salt thereof, or a ketone body or a salt thereof, and glycerol;

at least one hydrolysis product is a TCA cycle acid; and at least one hydrolysis product is a ketone body.

4. The compound of embodiment 1, 2, or 3, wherein:

each of $R^1$, $R^2$ and $R^3$ is independently —OC(O)R, wherein —OC(O)R is a moiety whose corresponding acid R—C(O)OH is a TCA cycle acid or beta-hydroxybutyric acid;

at least one of $R^1$, $R^2$ and $R^3$ is —OC(O)R, wherein —OC(O)R is a moiety whose corresponding acid R—C(O)OH is a TCA cycle acid; and at least one of $R^1$, $R^2$ and $R^3$ is —OC(O)R, wherein —OC(O)R is a moiety whose corresponding acid R—C(O)OH is beta-hydroxybutyric acid.

5. The compound of embodiment 4, wherein each of $R^1$, $R^2$ and $R^3$ is independently —OC(O)R, wherein each —OC(O)R is independently a moiety whose corresponding acid R—C(O)OH is succinic acid or beta-hydroxybutyric acid.

6. The compound of any one of the preceding embodiments, wherein two of $R^1$, $R^2$ and $R^3$ are independently —OC(O)R whose corresponding acid R—C(O)OH is succinic acid, and the third of $R^1$, $R^2$ and $R^3$ is —OC(O)R whose corresponding acid R—C(O)OH is beta-hydroxybutyric acid.

7. The compound of embodiment 6, wherein the compound is

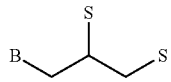

or a salt thereof, wherein B is —OC(O)CH$_2$CH(OH)CH$_3$ and S is —OC(O)CH$_2$CH$_2$C(O)OH.

8. The compound of any one of embodiments 1-5, wherein two of $R^1$, $R^2$ and $R^3$ are independently —OC(O)R whose corresponding acid R—C(O)OH is beta-hydroxybutyric acid, and the third of $R^1$, $R^2$ and $R^3$ is —OC(O)R whose corresponding acid R—C(O)OH is succinic acid.

9. The compound of embodiment 8, wherein the compound is

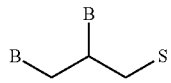

or a salt thereof, wherein B is —OC(O)CH$_2$CH(OH)CH$_3$ and S is —OC(O)CH$_2$CH$_2$COOH.

10. The compound of embodiment 1, 2, or 3, wherein each of $R^1$, $R^2$ and $R^3$ is independently —OC(O)-L$^1$-C(O)—O-L$^2$-C(O)OH, wherein each —OC(O)-L$^1$-C(O)— is independently a moiety whose corresponding acid HOC(O)-L$^1$-C(O)OH is a diacid or triacid of the TCA cycle, and each —O-L$^2$-C(O)OH is independently a moiety whose corresponding hydroxyacid HO-L$^2$-C(O)OH is beta-hydroxybutyric acid.

11. The compound of embodiment 10, wherein the compound is

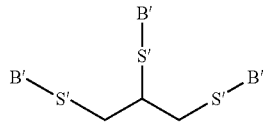

or a salt thereof, wherein S' is —OC(O)CH$_2$CH$_2$C(O)O—, and B' is —CH(CH$_3$)CH$_2$C(O)OH.

12. The compound of embodiment 1, 2, or 3, wherein the compound has the structure of U$_1$-[U$_2$-U$_3$]$_n$-U$_4$-U$_5$, wherein:

U$^1$ is

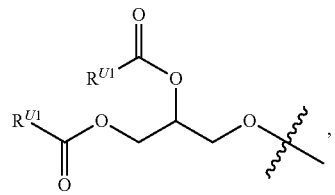

wherein each R$^{U1}$—C(O)O— is independently a moiety whose corresponding acid R$^{U1}$—C(O)OH is a TCA cycle acid, beta-hydroxybutyric acid or acetoacetic acid;

each of U$^2$ and U$^4$ is independently —C(O)-L$^1$-C(O)—, wherein each —C(O)-L$^1$-C(O)— is independently a moiety whose corresponding acid HOC(O)-L$^1$-C(O)OH is a TCA cycle diacid or triacid;

each U$^3$ is independently

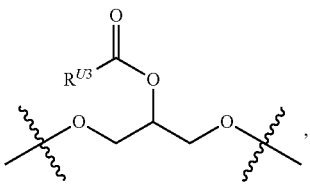

wherein each R$^{U3}$—C(O)O— is independently a moiety whose corresponding acid R$^{U3}$—C(O)OH is a TCA cycle acid, beta-hydroxybutyric acid or acetoacetic acid;

n is 0-20;

U$^5$ is

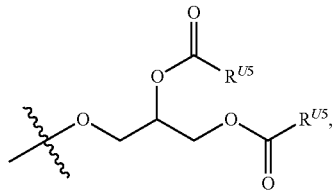

wherein each R$^{U5}$ is independently a moiety whose corresponding acid R$^{U5}$—C(O)OH is a TCA cycle acid, beta-hydroxybutyric acid or acetoacetic acid; and wherein at least one of R$^{U1}$—C(O)O—, R$^{U3}$—C(O)O—, and R$^{U5}$—C(O)O— is a moiety whose corresponding acid is beta-hydroxybutyric acid or acetoacetic acid.

13. The compound of embodiment 12, wherein:
U$^1$ is

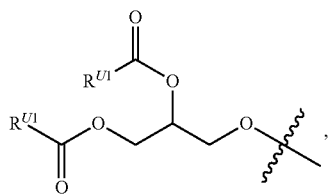

wherein each R$^{U1}$—C(O)O— is independently a moiety whose corresponding acid R$^{U1}$—C(O)OH is a TCA cycle acid or beta-hydroxybutyric acid;
each of U$^2$ and U$^4$ is independently —C(O)-L$^1$-C(O)—, wherein each —C(O)-L$^1$-C(O)— is independently a moiety whose corresponding acid HOC(O)-L$^1$-C(O)OH is a TCA cycle diacid or triacid;
each U$^3$ is independently

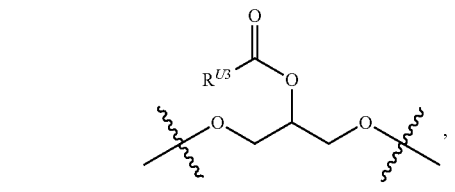

wherein each R$^{U3}$—C(O)O— is independently a moiety whose corresponding acid R$^{U3}$—C(O)OH is a TCA cycle acid or beta-hydroxybutyric acid;
n is 0-20;
U$^5$ is

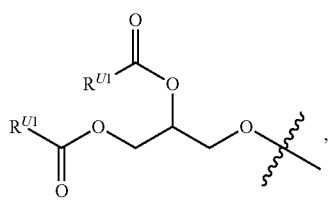

wherein each R$^{U5}$ is independently a moiety whose corresponding acid R$^{U5}$—C(O)OH is a TCA cycle acid or beta-hydroxybutyric acid; and
wherein at least one of R$^{U1}$—C(O)O—, R$^{U3}$—C(O)O—, and R$^{U5}$—C(O)O— is a moiety whose corresponding acid is beta-hydroxybutyric acid.

14. The compound of embodiment 12 or 13, wherein:
U$^1$ is

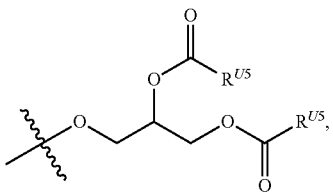

wherein each R$^{U1}$—C(O)O— is independently a moiety whose corresponding acid R$^{U1}$—C(O)OH is succinic acid or D-beta-hydroxybutyric acid; each of U$^2$ and U$^4$ is independently —C(O)-L$^1$-C(O)—, wherein each —C(O)-L$^1$-C(O)— is independently a moiety whose corresponding acid HOC(O)-L$^1$-C(O)OH is succinic acid;
each U$^3$ is independently

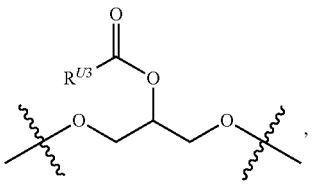

wherein each R$^{U3}$—C(O)O— is independently a moiety whose corresponding acid R$^{U3}$—C(O)OH is succinic acid or D-beta-hydroxybutyric acid;
n is 0-20;
U$^5$ is

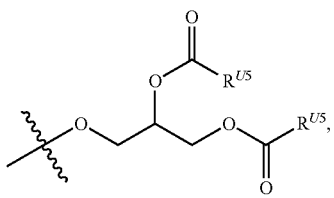

wherein each R$^{U5}$ is independently a moiety whose corresponding acid R$^{U5}$—C(O)OH is succinic acid or D-beta-hydroxybutyric acid; and
wherein at least one of R$^{U1}$—C(O)O—, R$^{U3}$—C(O)O—, and R$^{U5}$—C(O)O— is a moiety whose corresponding acid is D-beta-hydroxybutyric acid.

15. The compound of any one of embodiments 12-13, wherein n is 0.

16. The compound of any one of embodiments 12-15, wherein the compound is

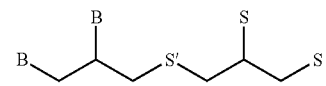

or a salt thereof, wherein B is —OC(O)CH$_2$CH(OH)CH$_3$, S' is —OC(O)CH$_2$CH$_2$C(O)O—, and S is —OC(O)CH$_2$CH$_2$C(O)OH.

17. The compound of any one of embodiments 12-14, wherein n is 1.

18. The compound of any one of embodiments 12-14 and 17, wherein the compound is

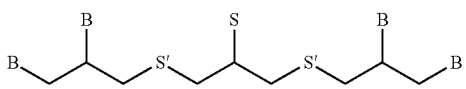

or a salt thereof, wherein B is —OC(O)CH$_2$CH(OH)CH$_3$, S' is —OC(O)CH$_2$CH$_2$C(O)O—, and S is —OC(O)CH$_2$CH$_2$C(O)OH.

19. The compound of any one of embodiments 12-14, wherein n is 0-10.

20. The compound of any one of embodiments 12-14, wherein n is 0-5.

21. A compound, formed by condensation of:
(a) one or more TCA cycle acids;
(b) one or more ketone bodies; and
(c) optionally one or more $C_{2-10}$ hydrocarbon compounds, each of which is independently substituted with two or more groups selected from hydroxyl, amino, and carboxyl groups; wherein the compound comprises at least one TCA cycle acid moiety derived from a TCA cycle acid, and at least one ketone body moiety derived from a ketone body.

22. The compound of embodiment 21, formed by condensation of:
(a) one or more TCA cycle acids;
(b) one or more ketone bodies; and
(c) one or more $C_{2-10}$ polyols.

23. The compound of embodiment 21 or 22, formed by condensation of:
(a) one or more TCA cycle acids;
(b) one or more ketone bodies; and
(c) glycerol.

24. The compound of embodiment 21, 22 or 23, wherein the compound is formed by condensation of succinic acid, beta-hydroxybutyric acid and glycerol.

25. A compound having the structure of formula I:

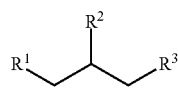

I wherein:
each of $R^1$, $R^2$ and $R^3$ is independently —B, —S, or —S'—B';
B is —OC(O)CH$_2$CH(OH)CH$_3$;
S is —OC(O)CH$_2$CH$_2$C(O)OH;
S' is —OC(O)CH$_2$CH$_2$C(O)O—;
B' is —CH(CH$_3$)CH$_2$C(O)OH; and
wherein when one of $R^1$, $R^2$ and $R^3$ is B or S, at least two of $R^1$, $R^2$ and $R^3$ are different.

26. A compound whose structure comprises a moiety of formula II:

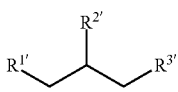

II wherein:
each of $R^{1'}$, $R^{2'}$ and $R^{3'}$ is independently —B, —S, —S'—B', —S', or —B",
B is —OC(O)CH$_2$CH(OH)CH$_3$;
S is —OC(O)CH$_2$CH$_2$C(O)OH;
S' is —OC(O)CH$_2$CH$_2$C(O)O—;
B' is —CH(CH$_3$)CH$_2$C(O)OH;
B" is —OC(O)CH$_2$CH(CH$_3$)O—; and
wherein when each ester bond in the compound is hydrolyzed, one of the hydrolysis product is succinic acid and one is beta-hydroxybutyric acid.

27. A compound produced by a method comprising steps of reacting a polyol with a TCA cycle acid and a ketone body, so that one or more ester, and optionally ketal, groups are formed linking the polyol, TCA cycle acid, and ketone body.

28. The compound of embodiment 27, wherein a plurality of TCA cycle acids are used in the method.

29. The compound of embodiment 27 or 28, wherein a plurality of ketone bodies are used in the method.

30. The compound of any one of 28-29, wherein the plurality of TCA cycle acids, or the plurality of ketone bodies, are reacted serially.

31. The compound of any one of embodiments 27-30, wherein two or more polyol units are linked together.

32. The compound of embodiment 31, wherein two or more polyol units are linked together by a TCA cycle diacid or triacid.

33. The compound of embodiment 32, wherein two or more polyol units are linked together by one or more succinic aid unit.

34. The compound of embodiment 27, wherein the TCA cycle acid is succinic acid and the ketone body is beta-hydroxybutyric acid.

35. A compound comprising one or more backbone moieties and optionally one or more linker moieties, wherein:
each backbone moiety is independently a $C_{2-10}$ hydrocarbon moiety substituted with two or more groups selected from hydroxyl, amino and carboxyl groups;
each backbone moiety is optionally substituted with one or more TCA acid moieties, ketone body moieties or combinations thereof, so that one or more of the groups selected from hydroxyl, amino and carboxyl groups are converted into the corresponding ester, amide or anhydride groups;
each linker moiety is independently a $C_{2-10}$ hydrocarbon moiety substituted with two or more carboxyl groups, and links two or more backbone moieties; and
wherein the compound comprises at least one TCA cycle acid moiety and at least one ketone body moiety.

36. The compound of embodiment 35, wherein:
each backbone moiety is independently a $C_{2-10}$ hydrocarbon moiety substituted with two or more groups selected from hydroxyl and amino groups;
each backbone moiety is optionally substituted with one or more TCA cycle acid moieties, ketone body moieties or combinations thereof, so that one or more of the groups selected from hydroxyl and amino groups are converted into the corresponding ester or amide groups; and
each linker moiety is independently a $C_{2-10}$ hydrocarbon moiety substituted with two or more carboxyl groups.

37. The compound of embodiment 35 or 36, wherein:
each backbone moiety is independently a $C_{2-10}$ hydrocarbon moiety substituted with two or more hydroxyl groups;
each backbone moiety is substituted with one or more TCA cycle acid moieties, ketone body moieties or combinations thereof, so that each hydroxyl group is independently converted into a corresponding ester group; and
each linker moiety is independently a TCA cycle diacid or triacid moiety.

38. The compound of any one of embodiments 35-37, wherein the compound is a compound of any one of embodiments 4-34.

39. The compound of embodiment 35, 36 or 37, wherein each backbone moiety is independently a glycerol moiety.

40. The compound of any one of embodiments 35-38, wherein each backbone moiety is optionally substituted with one or more succinic acid moieties, beta-hydroxybutyric acid moieties, or combinations thereof.

41. The compound of any one of embodiments 35-40, wherein a succinic acid moiety is S or S' and a beta-hydroxybutyric acid moiety is B, B' or B".

42. The compound of any one of the preceding embodiments, wherein the molecular weight of the compound is no more than about 10,000.
43. The compound of any one of the preceding embodiments, wherein the compound contains no more than 50 polyol moieties.
44. The compound of any one of the preceding embodiments, wherein the compound contains no more than 50 TCA cycle acid and ketone body moieties.
45. The compound of any one of the preceding embodiments, wherein the molar ratio of a TCA cycle acid moiety and a ketone body moiety is predetermined.
46. The compound of any one of the preceding embodiments, wherein the molar ratio of all the TCA cycle acid moieties and all the ketone body moieties is predetermined.
47. A pharmaceutical composition, comprising a compound of any one of embodiments 1-46, and a pharmaceutically acceptable carrier.
48. A composition comprising:
   1) one or more TCA cycle acid moieties; and
   2) one or more ketone body moieties;
   wherein:
   each TCA cycle acid moiety is independently a TCA cycle acid or a salt thereof, or a structural unit which, upon hydrolysis of the composition, is converted into a TCA cycle acid or a salt thereof; and
   each ketone body moiety is independently a ketone body or a salt thereof, or a structural unit which, upon hydrolysis of the composition, is converted into a ketone body.
49. The composition of embodiment 48, wherein hydrolysis of the composition comprises hydrolysis of ester and ketal groups.
50. The composition of embodiment 48 or 49, wherein hydrolysis of the composition consists of hydrolysis of all ester and ketal groups.
51. The composition of embodiment 48, comprising a predetermined level of:
   (a) a first compound selected from a first group consisting of TCA cycle acids and salts, amides, esters, ketals, and anhydrides thereof; and
   (b) a second compound selected from a second group consisting of ketone bodies and salts, amides, esters, ketals, and anhydrides thereof.
52. The composition of embodiment 51, wherein the first compound is succinic acid or a salt, amide, ester, ketal, and anhydride thereof, and the second compound is beta-hydroxybutyric acid or a salt, amide, ester, ketal, and anhydride thereof.
53. The composition of embodiment 48, wherein the composition is a composition comprising a compound of embodiment 17, wherein each TCA cycle acid and ketone body moiety is independently derivatized from the corresponding TCA cycle acid or ketone body of embodiment 17.
54. A composition which, when optionally fully hydrolyzed, provides a predetermined level of:
   (a) a TCA cycle acid or salt thereof; and
   (b) a ketone body or salt thereof.
55. The composition of embodiment 54, wherein the TCA cycle acid is succinic acid, and the ketone body is beta-hydroxybutyric acid.
56. The composition of any one of embodiments 48-55, wherein the molar ratio of a TCA cycle acid moiety and a ketone body moiety is predetermined.
57. The composition of any one of embodiments 48-56, wherein the molar ratio of a TCA cycle acid moiety and a ketone body moiety is between 1:100 to 100:1.
58. The compound or composition of any one of the preceding embodiments, wherein the molar ratio of (all TCA cycle acids):(all ketone bodies) is between about 100:1 and 1:100.
59. The compound or composition of any one of the preceding embodiments, wherein the molar ratio of (all TCA cycle acids):(all ketone bodies) is between about 10:1 and 1:10.
60. The composition of any one of embodiments 48-59, wherein the composition is a composition of embodiment 47.
61. A method, comprising administering to a subject suffering from or susceptible to a disease, disorder or condition a pharmaceutically effective amount of a compound of any one of embodiments 1-46 or a composition of any one of embodiments 47-60.
62. A method, comprising administering to a subject suffering from or susceptible to a disease, disorder or condition a pharmaceutically effective amount or a composition, which comprises a predetermined level of:
   (a) a first compound selected from a first group consisting of TCA cycle acids and salts, amides, esters, ketals, and anhydrides thereof; and
   (b) a second compound selected from a second group consisting of ketone bodies and salts, amides, esters, ketals, and anhydrides thereof.
63. The method of embodiment 62, wherein the first compound is a succinic acid or a pharmaceutically acceptable salt or ester thereof, and the second compound is a beta-hydroxybutyric acid or a pharmaceutically acceptable salt or ester thereof.
64. The method of any one of embodiments 61-63, wherein the disease, disorder or condition is an energetic disorder.
65. The method of any one of embodiments 61-63, wherein the disease, disorder or condition is refractory epilepsy.
66. The method of any one of embodiments 61-63, wherein the disease, disorder or condition is propionic acidemia (PA).
67. The method of any one of embodiments 61-63, wherein the disease, disorder or condition is methylmalonic acidemia (MMA).
68. The method of any one of embodiments 61-63, wherein the disease, disorder or condition is a long chain fatty acid oxidation disorder.
69. The method of any one of embodiments 61-63, wherein the disease, disorder or condition is succinyl-CoA lyase deficiency.
70. The method of any one of embodiments 61-63, wherein the disease, disorder or condition is pyruvate carboxylase deficiency.
71. The method of any one of embodiments 61-63, wherein the disease, disorder or condition is mitochondrial respiratory chain deficiencies.
72. The method of any one of embodiments 61-63, wherein the disease, disorder or condition is glutaric acidemia type 1.
73. The method of any one of embodiments 61-63, wherein the disease, disorder or condition is glutaric acidemia type 2.
74. The method of any one of embodiments 61-63, wherein the disease, disorder or condition is a neurologic disease, disorder or condition.
75. The method of any one of embodiments 61-63, wherein the disease, disorder or condition is Huntington's disease, disorder or condition.
76. The method of any one of embodiments 61-63, wherein the disease, disorder or condition is Parkinson's disease, disorder or condition.

77. The method of any one of embodiments 61-63, wherein the disease, disorder or condition is Alzheimer's disease, disorder or condition.
78. The method of any one of embodiments 61-63, wherein the disease, disorder or condition is cancer.
79. The method of any one of embodiments 61-63, wherein the disease, disorder or condition is a pain or fatigue disease.
80. The method of any one of embodiments 61-63, wherein the disease, disorder or condition is muscular dystrophy.
81. The method of any one of embodiments 61-63, wherein the disease, disorder or condition is Duchenne's muscular dystrophy.
82. The method of any one of embodiments 61-63, wherein the disease, disorder or condition is Becker's muscular dystrophy.
83. The method of any one of embodiments 61-63, wherein the disease, disorder or condition is mitochondrial myopathy.
84. The method of any one of embodiments 61-63, wherein the disease, disorder or condition is mitochondrial encephalomyopathy, lactic acidosis, and stroke-like syndrome (MELAS).
85. The method of any one of embodiments 61-63, wherein the disease, disorder or condition is myoclonic epilepsy and ragged-red fibers (MERRF).
86. The method of any one of embodiments 61-63, wherein the disease, disorder or condition is a mitochondrial associated disease.
87. The method of any one of embodiments 61-63, wherein the disease, disorder or condition is related to POLG mutation.
88. The compound, composition, or method of any one of the preceding embodiments, wherein the beta-hydroxybutyric acid is D-beta-hydroxybutyric acid.
89. The compound, composition, or method of any one of the preceding embodiments, wherein the TCA cycle acid is selected from succinic acid, fumaric acid, malic acid, oxaloacetic acid, citric acid, cis-aconitic acid, D-isocitric acid, and alpha-ketoglutaric acid.
90. The compound, composition, or method of any one of the preceding embodiments, wherein the TCA cycle diacid or triacid is selected from succinic acid, fumaric acid, malic acid, oxaloacetic acid, citric acid, cis-aconitic acid, D-isocitric acid, and alpha-ketoglutaric acid.
91. The compound, composition, or method of any one of the preceding embodiments, wherein the ketone body is selected from acetoacetic acid, acetone, and beta-hydroxybutyric acid.
92. The compound, composition, or method of any one of the preceding embodiments, wherein the ketone body is selected from acetoacetic acid, and beta-hydroxybutyric acid.
93. The compound, composition, or method of any one of the preceding embodiments, wherein the compound of any one of embodiments 1-46 is a liquid at room temperature and 1 atm.
94. The compound, composition, or method of any one of the preceding embodiments, wherein the compound has a purity of 80% or more.
95. The compound, composition, or method of any one of the preceding embodiments, wherein the compound has a purity of 85% or more.
96. The compound, composition, or method of any one of the preceding embodiments, wherein the compound has a purity of 90% or more.
97. The compound, composition, or method of any one of the preceding embodiments, wherein the compound has a purity of 95% or more.
98. The compound, composition, or method of any one of the preceding embodiments, wherein the compound has a purity of 97% or more.
99. The compound, composition, or method of any one of the preceding embodiments, wherein the compound has a purity of 98% or more.
100. The compound, composition, or method of any one of the preceding embodiments, wherein the compound has a purity of 99% or more.
101. The compound, composition, or method of any one of the preceding embodiments, wherein the compound has a purity of 99% or more.
102. The compound, composition or method of any one of the preceding embodiments, wherein the compound is administered by direct drinking of the compound.
103. The compound, composition or method of any one of the preceding embodiments, wherein the compound is administered at at least 0.1, 0.2, 0.3, 0.4, 0.5, 0.6, 0.7, 0.8, 0.9, 1.0, 1.1, 1.2, 1.3. 1.4, 1.5, 1.6. 1.7, 1.8. 1.9. 2.0, 2.5, 3, 3.5, 4 or 5 g/kg.
104. The compound, composition or method of any one of the preceding embodiments, wherein the compound is administered at at least 1 g/kg.
105. The compound, composition, or method of any one of the preceding embodiments, wherein the compound is administered at about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3, 3.5, 4 or 5 g/kg.
106. The compound, composition, or method of any one of the preceding embodiments, wherein the compound is administered at about 1 g/kg.
107. The compound, composition, or method of any one of the preceding embodiments, wherein the compound is administered at at least 0.1, 0.2, 0.3, 0.4, 0.5, 0.6, 0.7, 0.8, 0.9, 1.0, 1.1, 1.2, 1.3. 1.4, 1.5, 1.6. 1.7, 1.8. 1.9. 2.0, 2.5, 3, 3.5, 4 or 5 g/kg per day.
108. The compound, composition, or method of any one of the preceding embodiments, wherein the compound is administered at at least 1 g/kg per day.
109. The compound, composition, or method of any one of the preceding embodiments, wherein the compound is administered at at least 0.1, 0.2, 0.3, 0.4, 0.5, 0.6, 0.7, 0.8, 0.9, 1.0, 1.1, 1.2, 1.3. 1.4, 1.5, 1.6. 1.7, 1.8. 1.9. 2.0, 2.5, 3, 3.5, 4 or 5 g/kg per single dose.
110. The compound, composition or method of any one of the preceding embodiments, wherein the compound is administered at at least 1 g/kg per single dose.

Among other things, the present disclosure provides the following example embodiments:
1. A compound having the structure of formula I:

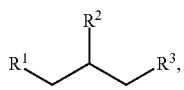

or a salt thereof, wherein:
each of $R^1$, $R^2$ and $R^3$ is independently —H, —OH, R, or R—C(O)O—, or may be independently and optionally taken together with a hydrogen atom on the carbon atom to which it is attached to form an oxo group;

each R is independently linear or branched $C_1$-$C_{100}$ aliphatic wherein one or more —$CH_2$ units are independently and optionally replaced with —O—, —C(O)—, —CH(OH)—, or —C(O)O—, and any two or more R groups may be linked by one or more linear or branched, bivalent or polyvalent, $C_1$-$C_{100}$ hydrocarbon group wherein one or more —$CH_2$— units are independently and optionally replaced with —O—, —C(O)—, —CH(OH)—, or —C(O)O—;

at least one of $R^1$, $R^2$ and $R^3$ is R—C(O)O—; and wherein when each ester group of the compound of formula I is hydrolyzed into its corresponding —OH and —COOH groups, each hydrolysis product is independently a compound selected from a TCA cycle acid or a salt thereof, a $C_2$-$C_{20}$ diol or polyol, and R'—C(O)OH or a salt thereof;

R' is $C_1$-$C_{20}$ aliphatic wherein one or more —$CH_2$— units are independently and optionally replaced with —O—, —C(O)—, —CH(OH)—, or —C(O)O—; and at least one hydrolysis product is a TCA cycle acid or a salt thereof.

2. The compound of embodiment 1, wherein:

each of $R^1$, $R^2$ and $R^3$ is independently —H, —OH, R, or R—C(O)O—, or may be independently and optionally taken together with a hydrogen atom on the carbon atom to which it is attached to form an oxo group;

each R is independently linear or branched $C_1$-$C_{100}$ aliphatic wherein one or more —$CH_2$— units are independently replaced with —O—, —C(O)—, —CH(OH)—, or —C(O)O—, and any two or more R groups may be linked by one or more linear or branched, bivalent or polyvalent, $C_1$-$C_{100}$ hydrocarbon group wherein one or more —$CH_2$— units are independently replaced with —O—, —C(O)—, —CH(OH)—, or —C(O)O—;

at least one of $R^1$, $R^2$ and $R^3$ is R'—C(O)O—; and wherein when each ester group of the compound of formula I is hydrolyzed into its corresponding —OH and —COOH groups, each hydrolysis product is independently a compound selected from a TCA cycle acid or a salt thereof, a $C_2$-$C_{20}$ diol or polyol, and R'—C(O)OH or a salt thereof;

R' is $C_1$-$C_{20}$ aliphatic wherein one or more —$CH_2$— units are independently and optionally replaced with —O—, —C(O)—, —CH(OH)—, or —C(O)O—; and at least one hydrolysis product is a TCA cycle acid or a salt thereof.

3. The compound of embodiment 1 or 2, wherein a $C_2$-$C_{20}$ diol or polyol is glycerol.

4. The compound of any one of the preceding embodiments, wherein the compound comprises at least 2, 3, or 4 R'—C(O)O— groups.

5. The compound of any one of the preceding embodiments, wherein the compound comprises at least 3 R'—C(O)O— groups.

6. The compound of any one of the preceding embodiments, wherein the compound comprises at least 4 R'—C(O)O— groups.

7. The compound of any one of the preceding embodiments, wherein the compound contains four R'—C(O)O— groups.

8. The compound of any one of embodiments 4-5, wherein the R'—C(O)O— groups are the same.

9. The compound of any one of embodiments 4-5, wherein at least one R'—C(O)O— group is different from another R'—C(O)O— group.

10. The compound of any one of embodiments 1-9, wherein each of $R^2$ and $R^3$ is independently R'—C(O)O—.

11. The compound of any one of embodiments 1-6, wherein $R^1$ is linear or branched $C_5$-$C_{100}$, $C_6$-$C_{100}$, $C_7$-$C_{100}$, $C_8$-$C_{100}$, $C_9$-$C_{100}$, $C_{10}$-$C_{100}$, $C_{11}$-$C_{100}$, $C_{12}$-$C_{100}$, $C_{13}$-$C_{100}$, $C_{14}$-$C_{100}$, or $C_{15}$-$C_{100}$, aliphatic wherein one or more —$CH_2$— units are independently and optionally replaced with —O—, —C(O)—, or —C(O)O—.

12. The compound of any one of embodiments 1-6, wherein $R^1$ is linear or branched $C_{15}$-$C_{100}$, aliphatic wherein one or more —$CH_2$— units are independently and optionally replaced with —O—, —C(O)—, or —C(O)O—.

13. The compound of any one of embodiments 1-6, wherein $R^1$ is branched $C_{15}$-$C_{100}$, aliphatic wherein one or more —$CH_2$— units are independently and optionally replaced with —O—, —C(O)—, or —C(O)O—.

14. The compound of any one of embodiments 1-7, wherein each R is independently linear or branched $C_1$-$C_{100}$ aliphatic wherein one or more —$CH_2$— units are independently and optionally replaced with —C(O)O—, and any two R groups may be linked by one or more linear or branched, bivalent or polyvalent, $C_1$-$C_{100}$ hydrocarbon group wherein one or more —$CH_2$— units are independently and optionally replaced with —C(O)O—.

15. The compound of any one of embodiments 1-6, wherein $R^1$ is linear or branched $C_5$-$C_{100}$, $C_6$-$C_{100}$, $C_7$-$C_{100}$, $C_8$-$C_{100}$, $C_9$-$C_{100}$, $C_{10}$-$C_{100}$, $C_{11}$-$C_{100}$, $C_{12}$-$C_{100}$, $C_{13}$-$C_{100}$, $C_{14}$-$C_{100}$, or $C_{15}$-$C_{100}$, aliphatic wherein one or more —$CH_2$— units are independently replaced with —C(O)O—.

16. The compound of any one of embodiments 1-6, wherein $R^1$ is linear or branched $C_{15}$-$C_{100}$, aliphatic wherein one or more —$CH_2$— units are independently replaced with —C(O)O—.

17. The compound of any one of embodiments 1-16, wherein $R^1$ is branched $C_{11}$-$C_{100}$, aliphatic wherein one or more —$CH_2$— units are independently replaced with —C(O)O—.

18. The compound of any one of embodiments 1-17, wherein $R^1$ comprises a —OC(O)—$CH_2$—$CH_2$—C(O)O— moiety.

19. The compound of any one of embodiments 1-18, wherein $R^1$ comprises at least 2, 3, or 4 R'—C(O)O— groups.

20. The compound of any one of embodiments 1-18, wherein $R^1$ contains two R'—C(O)O— groups.

21. The compound of any one of embodiments 1-20, wherein $R^1$ comprises two different R'—C(O)O— groups.

22. The compound of any one of embodiments 1-20, wherein $R^1$ comprises two R'—C(O)O— groups having the same structure.

23. The compound of any one of embodiments 1-22, wherein $R^1$ is —OC(O)—$CH_2$—$CH_2$—C(O)O—R, wherein R is $C_{11}$-$C_{50}$ aliphatic wherein one or more —$CH_2$ units are independently replaced with —C(O)O—.

24. The compound of embodiment 23, wherein $R^1$ is —OC(O)—$CH_2$—$CH_2$—C(O)O—R, wherein R comprises at least 2, 3, or 4 R'—C(O)O— groups.

25. The compound of embodiment 23, wherein $R^1$ is —OC(O)—$CH_2$—$CH_2$—C(O)O—R, wherein R contains two R'—C(O)O— groups.

26. The compound of any one of embodiments 23-8, wherein $R^1$ is —OC(O)—$CH_2$—$CH_2$—C(O)O—R, wherein R comprises two different R'—C(O)O— groups.

27. The compound of any one of embodiments 23-8, wherein $R^1$ is —OC(O)—$CH_2$—$CH_2$—C(O)O—R, wherein R comprises two R'—C(O)O— groups having the same structure.

28. The compound of any one of the preceding embodiments, wherein R' is $C_1$-$C_{15}$ aliphatic.

29. The compound of any one of the preceding embodiments, wherein R' is $C_1$-$C_{10}$ aliphatic.

30. The compound of any one of the preceding embodiments, wherein R' is linear alkyl.

31. The compound of embodiment 1, wherein the compound has the structure of formula I-a:

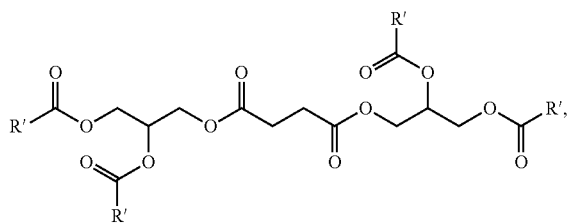

I-a or a salt thereof.

32. The compound of embodiment 1, wherein the compound has the structure of $U_1\text{-}[U_2\text{-}U_3]_n\text{-}U_4\text{-}U_5$, wherein:

$U^1$ is

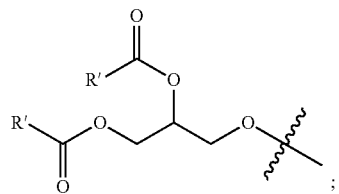

;

each of $U^2$ and $U^4$ is independently —C(O)-L$^1$-C(O)—, wherein L$^1$ is a bivalent $C_1\text{-}C_{20}$ aliphatic group wherein one or more —CH$_2$— units are independently and optionally replaced with —O—, —C(O)—, or —C(O)O—;

each $U^3$ is independently

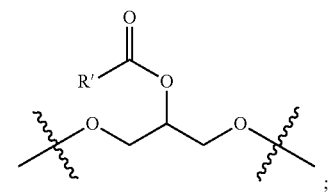

;

n is 0-20;

$U^5$ is

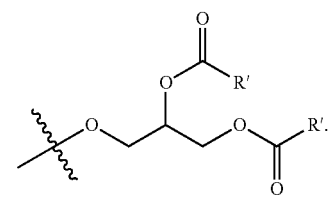

.

33. The compound of embodiment 32, each —C(O)-L$^1$-C(O)— is independently a moiety whose corresponding acid HOC(O)-L$^1$-C(O)OH is a TCA cycle diacid or triacid.

34. The compound of embodiment 33, each —C(O)-L$^1$-C(O)— is independently a moiety whose corresponding acid HOC(O)-L$^1$-C(O)OH is succinic acid.

35. The compound of any one of embodiments 32-34, wherein n is 0.

36. A compound comprising:
one or more TCA cycle acid moieties;
one or more carboxylic acid moieties having the structure of R'—C(O)— wherein R' is $C_1\text{-}C_{20}$ aliphatic wherein one or more —CH$_2$— units are independently and optionally replaced with —O—, —C(O)—, —CH(OH)—, or —C(O)O—; and
one or more $C_{2\text{-}10}$ diol or polyol moieties;
wherein the one or more TCA cycle acid moieties, the one or more carboxylic acid moieties, and the one or more diol or polyol moieties are connected via ester groups.

37. The compound of embodiment 36, wherein there is no free —OH group in the provided compound.

38. The compound of embodiment 36 or 37, wherein there is no free —C(O)OH group in the provided compound.

39. The compound of any one of embodiments 36-38, wherein the numbers of TCA cycle acid moieties, carboxylic acid moieties, and $C_{2\text{-}10}$ diol or polyol moieties are predetermined.

40. The compound of any one of embodiments 36-38, wherein a $C_{2\text{-}10}$ diol or polyol moiety is a glycerol moiety.

41. A compound, formed by condensation of:
(a) one or more TCA cycle acids;
(b) one or more compounds having the structure of R'—C(O)OH, wherein R' is $C_1\text{-}C_{20}$ aliphatic wherein one or more —CH$_2$— units are independently and optionally replaced with —O—, —C(O)—, —CH(OH)—, or —C(O)O—; and
(c) optionally one or more backbone moiety compounds.

42. The compound of embodiment 41, formed by condensation of:
(a) one or more TCA cycle acids;
(b) one or more compounds having the structure of R'—C(O)OH, wherein R' is $C_1\text{-}C_{20}$ aliphatic; and
(c) one or more backbone moiety compounds.

43. The compound of embodiment 41 or 42, wherein the backbone moiety compound is a $C_{2\text{-}10}$ hydrocarbon compound which is independently substituted with two or more groups selected from hydroxyl, amino, and carboxyl groups 44. The compound of embodiment 41 or 42, wherein the backbone moiety compound is a $C_{2\text{-}10}$ hydrocarbon compound which is independently substituted with two or more groups selected from hydroxyl and amino carboxyl groups 45. The compound of any one of embodiments 41-44, wherein a one or more backbone moiety compound is a $C_{2\text{-}10}$ diol or polyol.

46. The compound of embodiment 45, wherein the $C_{2\text{-}10}$ diol or polyol moiety is a glycerol moiety.

47. A compound, formed by condensation of:
(a) one or more TCA cycle acids;
(b) one or more compounds having the structure of R'—C(O)OH, wherein R' is $C_1\text{-}C_{20}$ aliphatic wherein one or more —CH$_2$— units are independently and optionally replaced with —O—, —C(O)—, —CH(OH)—, or —C(O)O—; and
(c) one or more $C_{2\text{-}10}$ diol or polyol.

48. The compound of embodiment 47, formed by condensation of:
(a) one or more TCA cycle acids;
(b) one or more compounds having the structure of R'—C(O)OH, wherein R' is $C_1\text{-}C_{20}$ aliphatic; and
(c) glycerol.

49. The compound of embodiment 47 or 48, formed by condensation of:
(a) succinic acid;
(b) one or more compounds having the structure of R'—C(O)OH, wherein R' is $C_1\text{-}C_{20}$ aliphatic; and
(c) glycerol.

50. The compound of any one of embodiments 41-49, wherein the condensation is performed using one or more condensing reagent and/or bases.
51. The compound of any one of embodiments 41-50, wherein the compound contains no free —C(O)OH group.
52. The compound of any one of embodiments 41-50, wherein the compound contains no free —OH group.
53. The compound of any one of the preceding embodiments, wherein R' is $C_1$-$C_{20}$ aliphatic.
54. The compound of any one of the preceding embodiments, wherein R' is $C_1$-$C_{11}$ aliphatic.
55. The compound of any one of embodiments 9-52, wherein the R' groups are the same.
56. The compound of any one of embodiments 9-52, wherein at least one R' is different from another R'.
57. The compound of any one of the preceding embodiments, wherein R' is $C_1$-$C_7$ aliphatic.
58. The compound of any one of the preceding embodiments, wherein R' is $C_3$-$C_7$ aliphatic.
59. The compound of any one of the preceding embodiments, wherein the compound comprises a R'—C(O)O— group, wherein R' is $CH_3$—.
60. The compound of any one of embodiments 1-56, wherein the compound comprises a R'—C(O)O— group, wherein R' is $CH_3CH_2$—.
61. The compound of any one of embodiments 1-56, wherein the compound comprises a R'—C(O)O— group, wherein R' is $C_3$ aliphatic.
62. The compound of any one of embodiments 1-56, wherein the compound comprises a R'—C(O)O— group, wherein R' is $C_4$ aliphatic.
63. The compound of any one of embodiments 1-56, wherein the compound comprises a R'—C(O)O— group, wherein R' is $C_5$ aliphatic.
64. The compound of any one of embodiments 1-56, wherein the compound comprises a R'—C(O)O— group, wherein R' is $C_6$ aliphatic.
65. The compound of any one of embodiments 1-56, wherein the compound comprises a R'—C(O)O— group, wherein R' is $C_7$ aliphatic.
66. The compound of any one of embodiments 1-56, wherein the compound comprises a R'—C(O)O— group, wherein R' is $C_8$ aliphatic.
67. The compound of any one of embodiments 1-56, wherein the compound comprises a R'—C(O)O— group, wherein R' is $C_9$ aliphatic.
68. The compound of any one of embodiments 1-56, wherein the compound comprises a R'—C(O)O— group, wherein R' is $C_{10}$ aliphatic.
69. The compound of any one of embodiments 1-56, wherein the compound comprises a R'—C(O)O— group, wherein R' is $C_{11}$ aliphatic.
70. The compound of any one of embodiments 53-69, wherein R' is linear alkyl.
71. The compound of any one of embodiments 61-69, wherein R' is linear alkyl.
72. The compound of any one of embodiments 1-56, wherein R' is $CH_3(CH_2)_2$—.
73. The compound of any one of embodiments 1-56, wherein R' is $CH_3(CH_2)_6$—.
74. The compound of any one of embodiments 1-56, wherein the compound comprises a $CH_3(CH_2)_2$—C(O)O— group.
75. The compound of any one of embodiments 1-56, wherein the compound comprises a $CH_3(CH_2)_6$—C(O)O— group.
76. The compound of any one of embodiments 1-56, wherein each R'—C(O)O— group within the compound is independently $CH_3(CH_2)_2$—C(O)O— or $CH_3(CH_2)_6$—C(O)O—.
77. The compound of any one of the preceding embodiments, wherein at least one hydrolysis product is succinic acid or a salt thereof.
78. The compound of any one of the preceding embodiments, wherein at least one hydrolysis product is glycerol.
79. The compound of any one of the preceding embodiments, wherein at least one hydrolysis product is R'—C(O)OH or a salt thereof.
80. The compound of any one of the preceding embodiments, wherein R'—C(O)OH or a salt thereof is different than the TCA cycle acid hydrolysis product or a salt thereof.
81. The compound of any one of the preceding embodiments, wherein R'—C(O)OH or a salt thereof is not a TCA cycle acid or a salt thereof.
82. The compound of any one of the preceding embodiments, wherein R'—C(O)OH or a salt thereof is not a ketone body or a salt thereof.
83. The compound of any one of the preceding embodiments, wherein the TCA cycle acid is selected from pyruvic acid, oxaloacetic acid, citric acid, cis-aconitic acid, D-isocitric acid, alpha-ketoglutaric acid, succinic acid, fumaric acid and malic acid.
84. The compound of any one of the preceding embodiments, wherein the TCA cycle acid is selected from oxaloacetic acid, citric acid, cis-aconitic acid, D-isocitric acid, alpha-ketoglutaric acid, succinic acid, fumaric acid and malic acid.
85. The compound of any one of the preceding embodiments, wherein the TCA cycle acid is succinic acid.
86. The compound of any one of the preceding embodiments, wherein the compound comprises at least one R'—C(O)O— group, whose corresponding acid R'—C(O)OH can be metabolized in a human being to provide a ketone body.
87. The compound of embodiment 80, wherein the ketone body is beta-hydroxybutyric acid.
88. The compound of any one of the preceding embodiments, wherein the compound comprises at least one R'—C(O)O— group, whose corresponding acid R'—C(O)OH can be metabolized in a human being to provide acetyl-CoA and/or propionyl-CoA.
89. The compound of any one of the preceding embodiments, wherein the compound comprises at least one R'—C(O)O— group, whose corresponding acid R'—C(O)OH can be metabolized in a human being to provide acetyl-CoA.
90. The compound of any one of the preceding embodiments, wherein the molecular weight of the compound is no more than about 10,000.
91. The compound of any one of the preceding embodiments, wherein the molecular weight of the compound is no more than about 1,000.
92. The compound of any one of the preceding embodiments, wherein the compound contains no more than 10 polyol moieties.
93. The compound of any one of the preceding embodiments, wherein the compound contains no more than 5 polyol moieties.
94. The compound of any one of the preceding embodiments, wherein the compound contains no more than 2 polyol moieties.
95. The compound of any one of the preceding embodiments, wherein the compound contains no more than 1 polyol moieties.

96. The compound of any one of the preceding embodiments, wherein the compound contains no more than 10 TCA cycle acid moieties.

97. The compound of any one of the preceding embodiments, wherein the compound contains no more than 5 TCA cycle acid moieties.

98. The compound of any one of the preceding embodiments, wherein the compound contains no more than 2 TCA cycle acid moieties.

99. The compound of any one of the preceding embodiments, wherein the compound contains no more than 1 TCA cycle acid moieties.

100. The compound of any one of the preceding embodiments, wherein the compound contains no more than 10 R'—C(O)O—.

101. The compound of any one of the preceding embodiments, wherein the compound contains no more than 5 R'—C(O)O—.

102. The compound of any one of the preceding embodiments, wherein the compound contains no more than 4 R'—C(O)O—.

103. The compound of any one of the preceding embodiments, wherein when each ester group of the compound is hydrolyzed, the ratio of the TCA cycle acid or a salt thereof in the hydrolysis product and R'—C(O)OH or a salt thereof in the hydrolysis product is no less than 1:4.

104. A compound, wherein the compound is selected from compounds I-1 to I-30, or a pharmaceutically acceptable salt thereof.

105. A compound, wherein the compound is selected from compounds I-1 to I-15, I-17 to I-19, I-21, and I-23 to I-31, or a pharmaceutically acceptable salt thereof.

106. The compound of any one of the preceding embodiments, wherein the compound is selected from compounds I-1, I-8 to I-19, and I-21 to I-30, or a pharmaceutically acceptable salt thereof.

107. The compound of any one of the preceding embodiments, wherein the compound is selected from compounds I-1, I-8 to 1-19, I-21, and I-23 to I-30, or a pharmaceutically acceptable salt thereof.

108. The compound of any one of the preceding embodiments, wherein the compound is selected from compounds I-1, I-8 to I-15, I-17 to I-19, I-21, and I-23 to I-30, or a pharmaceutically acceptable salt thereof.

109. The compound of any one of the preceding embodiments, wherein the compound is a liquid at room temperature and 1 atm.

110. The compound of any one of the preceding embodiments, wherein the compound is of sufficient low viscosity so that the compound can be administered by direct drinking by a subject.

111. The compound of any one of the preceding embodiments, wherein the compound has lower viscosity than glycerol at room temperature.

112. The compound of any one of the preceding embodiments, wherein the compound is palatable to be administered by direct drinking by a subject.

113. The compound of any one of the preceding embodiments, wherein the compound can be administered to a human subject at at least 0.1, 0.2, 0.3, 0.4, 0.5, 0.6, 0.7, 0.8, 0.9, 1.0, 1.1, 1.2, 1.3. 1.4, 1.5, 1.6. 1.7, 1.8. 1.9. 2.0, 2.5, 3, 3.5, 4 or 5 g/kg.

114. The compound of any one of the preceding embodiments, wherein the compound can be administered to a human subject at at least 0.1, 0.2, 0.3, 0.4, 0.5, 0.6, 0.7, 0.8, 0.9, 1.0, 1.1, 1.2, 1.3. 1.4, 1.5, 1.6. 1.7, 1.8. 1.9. 2.0, 2.5, 3, 3.5, 4 or 5 g/kg per day.

115. The compound of any one of the preceding embodiments, wherein the compound can be administered to a human subject at at least 0.1, 0.2, 0.3, 0.4, 0.5, 0.6, 0.7, 0.8, 0.9, 1.0, 1.1, 1.2, 1.3. 1.4, 1.5, 1.6. 1.7, 1.8. 1.9. 2.0, 2.5, 3, 3.5, 4 or 5 g/kg single dose.

116. The compound of any one of the preceding embodiments, wherein the compound can be administered to a human subject at at least 1 g/kg.

117. The compound of any one of the preceding embodiments, wherein the compound can be administered to a human subject at at least 1 g/kg per day.

118. The compound of any one of the preceding embodiments, wherein the compound can be administered to a human subject at at least 1 g/kg per single dose.

119. The compound of any one of the preceding embodiments, wherein the compound can be administered to a human subject at about 0.1, 0.2, 0.3, 0.4, 0.5, 0.6, 0.7, 0.8, 0.9, 1.0, 1.1, 1.2, 1.3. 1.4, 1.5, 1.6. 1.7, 1.8. 1.9. 2.0, 2.5, 3, 3.5, 4 or 5 g/kg.

120. The compound of any one of the preceding embodiments, wherein the compound can be administered to a human subject at about 0.1, 0.2, 0.3, 0.4, 0.5, 0.6, 0.7, 0.8, 0.9, 1.0, 1.1, 1.2, 1.3. 1.4, 1.5, 1.6. 1.7, 1.8. 1.9. 2.0, 2.5, 3, 3.5, 4 or 5 g/kg per day.

121. The compound of any one of the preceding embodiments, wherein the compound can be administered to a human subject at about 0.1, 0.2, 0.3, 0.4, 0.5, 0.6, 0.7, 0.8, 0.9, 1.0, 1.1, 1.2, 1.3. 1.4, 1.5, 1.6. 1.7, 1.8. 1.9. 2.0, 2.5, 3, 3.5, 4 or 5 g/kg per single dose.

122. The compound of any one of the preceding embodiments, wherein the compound can be administered to a human subject at about 1 g/kg.

123. The compound of any one of the preceding embodiments, wherein the compound can be administered to a human subject at about 1 g/kg per day.

124. The compound of any one of the preceding embodiments, wherein the compound can be administered to a human subject at about 1 g/kg per single dose.

125. The compound of embodiment 1, wherein the compound is 1-29 or a pharmaceutically acceptable salt thereof.

126. The compound of embodiment 1, wherein the compound is 1-30 or a pharmaceutically acceptable salt thereof.

127. The compound of embodiment 1, wherein the compound is 1-31 or a pharmaceutically acceptable salt thereof.

128. The compound of embodiment 1, wherein the compound is

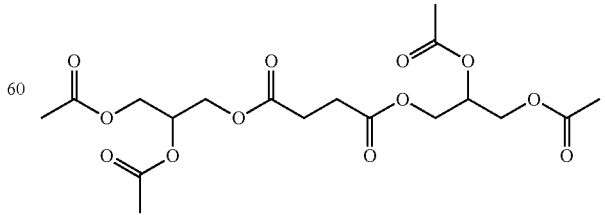

129. The compound of embodiment 1, wherein the compound is

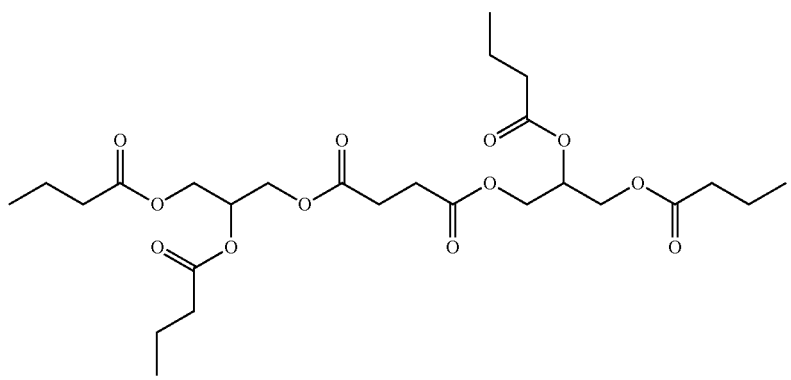

130. The compound of embodiment 1, wherein the compound is

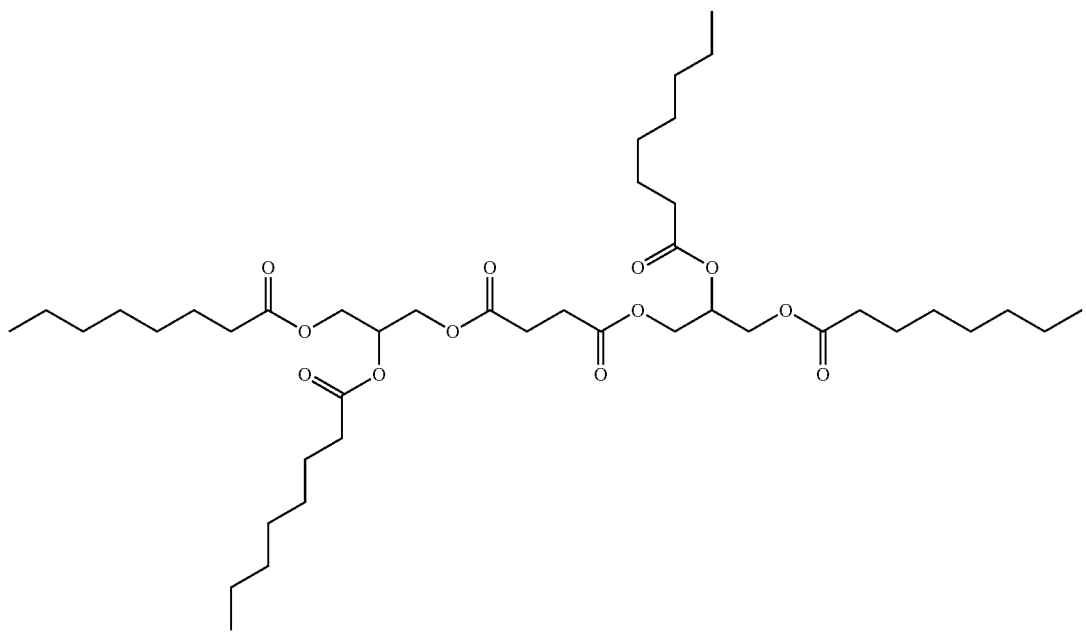

131. The compound of any one of the preceding embodiments, wherein the compound has a purity of no less than about 50%, 60%, 70%, 80%, 90%, 91%, 92%, 93%, 94%, 95%, 96%, 97%, 98%, 99%, 99.5% or 99.9%.

132. The compound of any one of the preceding embodiments, wherein the compound has a purity of no less than about 80%.

133. The compound of any one of the preceding embodiments, wherein the compound has a purity of no less than about 90%.

134. The compound of any one of the preceding embodiments, wherein the compound has a purity of no less than about 95%.

135. The compound of any one of the preceding embodiments, wherein the compound has a purity of no less than about 96%.

136. The compound of any one of the preceding embodiments, wherein the compound has a purity of no less than about 97%.

137. The compound of any one of the preceding embodiments, wherein the compound has a purity of no less than about 98%.

138. The compound of any one of the preceding embodiments, wherein the compound has a purity of no less than about 99%.

139. The compound of any one of the preceding embodiments, wherein the compound has a purity of no less than about 99.5%.

140. The compound of any one of the preceding embodiments, wherein the compound has a purity of no less than about 99.9%.

141. A pharmaceutical composition, comprising a compound of any one of embodiments 1-140, and a pharmaceutically acceptable carrier.

142. A method, comprising administering to a subject suffering from or susceptible to a disease, disorder or condition a pharmaceutically effective amount of a compound of any one of embodiments 1-140 or a composition of embodiment 141.

143. The method of embodiment 17, wherein the disease, disorder or condition is an energetic disorder.
144. The method of embodiment 17, wherein the disease, disorder or condition is refractory epilepsy.
145. The method of embodiment 17, wherein the disease, disorder or condition is propionic acidemia (PA).
146. The method of embodiment 17, wherein the disease, disorder or condition is methylmalonic acidemia (MMA).
147. The method of embodiment 17, wherein the disease, disorder or condition is a long chain fatty acid oxidation disorder.
148. The method of embodiment 17, wherein the disease, disorder or condition is succinyl-CoA lyase deficiency.
149. The method of embodiment 17, wherein the disease, disorder or condition is pyruvate carboxylase deficiency.
150. The method of embodiment 17, wherein the disease, disorder or condition is mitochondrial respiratory chain deficiencies.
151. The method of embodiment 17, wherein the disease, disorder or condition is glutaric acidemia type 1.
152. The method of embodiment 17, wherein the disease, disorder or condition is glutaric acidemia type 2.
153. The method of embodiment 17, wherein the disease, disorder or condition is a neurologic disease, disorder or condition.
154. The method of embodiment 17, wherein the disease, disorder or condition is Huntington's disease, disorder or condition.
155. The method of embodiment 17, wherein the disease, disorder or condition is Parkinson's disease, disorder or condition.
156. The method of embodiment 17, wherein the disease, disorder or condition is Alzheimer's disease, disorder or condition.
157. The method of embodiment 17, wherein the disease, disorder or condition is cancer.
158. The method of embodiment 17, wherein the disease, disorder or condition is a pain or fatigue disease.
159. The method of embodiment 17, wherein the disease, disorder or condition is muscular dystrophy.
160. The method of embodiment 17, wherein the disease, disorder or condition is Duchenne's muscular dystrophy.
161. The method of embodiment 17, wherein the disease, disorder or condition is Becker's muscular dystrophy.
162. The method of embodiment 17, wherein the disease, disorder or condition is mitochondrial myopathy.
163. The method of embodiment 17, wherein the disease, disorder or condition is mitochondrial encephalomyopathy, lactic acidosis, and stroke-like syndrome (MELAS).
164. The method of embodiment 17, wherein the disease, disorder or condition is myoclonic epilepsy and ragged-red fibers (MERRF).
165. The method of embodiment 17, wherein the disease, disorder or condition is a mitochondrial associated disease.
166. The method of embodiment 17, wherein the disease, disorder or condition is related to POLG mutation.
167. The method of any one of embodiments 17-18, wherein the compound is administered by direct drinking of the compound.
168. The method of any one of embodiments 17-18, wherein the compound is administered at at least 0.1, 0.2, 0.3, 0.4, 0.5, 0.6, 0.7, 0.8, 0.9, 1.0, 1.1, 1.2, 1.3. 1.4, 1.5, 1.6. 1.7, 1.8. 1.9. 2.0, 2.5, 3, 3.5, 4 or 5 g/kg.
169. The method of any one of embodiments 17-18, wherein the compound is administered at at least 1 g/kg.
170. The method of any one of embodiments 17-20, wherein the compound is administered at at least 0.1, 0.2, 0.3, 0.4, 0.5, 0.6, 0.7, 0.8, 0.9, 1.0, 1.1, 1.2, 1.3. 1.4, 1.5, 1.6. 1.7, 1.8. 1.9. 2.0, 2.5, 3, 3.5, 4 or 5 g/kg per day.
171. The method of any one of embodiments 17-20, wherein the compound is administered at at least 1 g/kg per day.
172. The method of any one of embodiments 17-171, wherein the compound is administered at at least 0.1, 0.2, 0.3, 0.4, 0.5, 0.6, 0.7, 0.8, 0.9, 1.0, 1.1, 1.2, 1.3. 1.4, 1.5, 1.6. 1.7, 1.8. 1.9. 2.0, 2.5, 3, 3.5, 4 or 5 g/kg per single dose.
173. The method of any one of embodiments 17-171, wherein the compound is administered at at least 1 g/kg per single dose.
174. The method of any one of embodiments 17-18, wherein the compound is administered at about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3, 3.5, 4 or 5 g/kg.
175. The method of any one of embodiments 17-18, wherein the compound is administered at about 1 g/kg.
176. The method of any one of embodiments 17-175, wherein the compound is administered at about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3, 3.5, 4 or 5 g/kg per day.
177. The method of any one of embodiments 17-175, wherein the compound is administered at about 1 g/kg per day.
178. The method of any one of embodiments 17-177, wherein the compound is administered at about 0.1, 0.2, 0.3, 0.4, 0.5, 0.6, 0.7, 0.8, 0.9, 1.0, 1.1, 1.2, 1.3. 1.4, 1.5, 1.6. 1.7, 1.8. 1.9. 2.0, 2.5, 3, 3.5, 4 or 5 g/kg per single dose.
179. The method of any one of embodiments 17-177, wherein the compound is administered at about 1 g/kg per single dose.

EXAMPLES

Non-limiting examples are provided below. A person of ordinary skill in the art appreciates that other compounds, compositions and methods can similarly be prepared and performed in accordance with the present disclosure.

Various methods are widely known and practiced in the art, and can be utilized to prepare and/or test provided compound in accordance with the present disclosure. For example, a number of esterification methods can be used in accordance with the present disclosure as described in the examples in the present disclosure.

Example 1. Preparation of Compound I-29

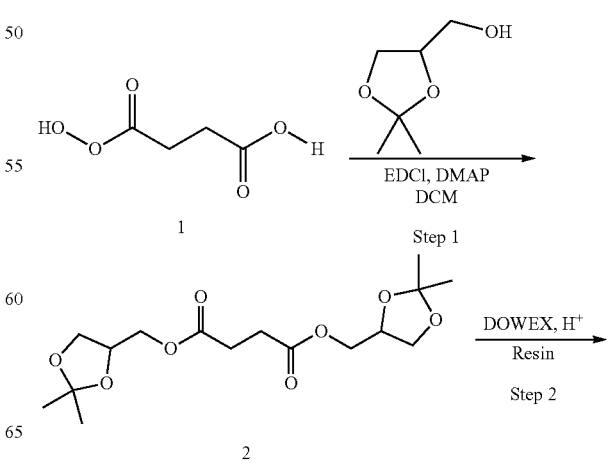

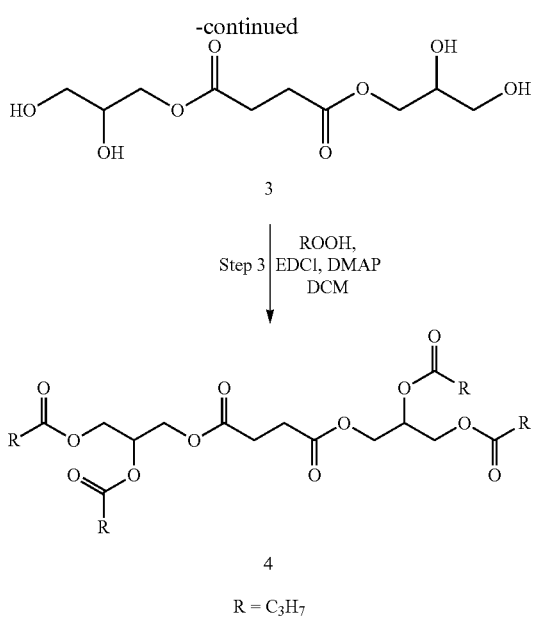

R = C₃H₇

Experimental Procedure

Step 1:

A suspension of succinic acid 1 (5 gm, 0.042 mol) in DCM (30 mL) was cooled to 0° C. To this was added solketal (11.74 gm, 0.089 mol) followed by addition of EDCI (25.89 gm, 0.14 mol) and DMAP (1.55 gm, 0.013 mol) at 0° C. The reaction was slowly warmed to room temperature and stirred overnight. The reaction mixture was diluted with ethyl acetate and washed with water (200 mL), sat. aq. sodium bicarbonate (200 mL) and brine (200 mL). The organic layer was dried over anhydrous sodium sulfate and concentrated. This crude residue was purified by column chromatography using hexanes and ethyl acetate (starting from 10% ethyl acetate and increased gradually to 40% ethyl acetate) to obtain 9.5 gm (65% yield) of colorless oil 2.

Step 2:

To a cooled solution of compound 2 (9.5 gm) in methanol (130 mL) was added acidic resin (Amberlyst15 Hydrogen form, 20 gm). The reaction mixture was allowed to reach room temperature and stirred for 5 hrs. The resin was filtered off and the filtrate was concentrated and the concentrate was purified by column chromatography with increasing gradient of ethanol 1% to 20% in DCM to obtain 6 gm (82% Yield) of compound 3 as colorless syrupy liquid.

Step 3:

To a solution of compound 3 (6 gm, 0.023 mol) in DCM (70 mL) was added butanoic acid (9.92 gm, 0.113 mol) at 0° C. followed by addition of EDCI (25.8 gm, 0.14 mol) and DMAP (1.65 gm, 0.014 mol). The reaction mixture was allowed to reach room temperature and stirred overnight. The reaction mixture was diluted with ethyl acetate and washed with water (200 mL), sat. aq. sodium bicarbonate (200 mL) and brine (200 mL). The organic layer was dried over anhydrous sodium sulfate and concentrated. This crude residue was purified by column chromatography using hexanes and ethyl acetate (starting from 10% ethyl acetate and increased gradually to 40% ethyl acetate) to obtain 5.6 gm (45.5% Yield) of compound 4 as a liquid with >97% NMR purity. Example NMR spectra is presented in FIG. 1.

Example 2. Preparation of Compound I-30

An additional/alternative method for making provided compound is described in example 2. As appreciated by a person having ordinary skill in the art, the procedures in example 2 can also be used to prepare compound I-29 and other provided compounds.

Procedure for Synthesis of Bis (2,3-bis(octanoyloxy)propyl) succinate (12)

Step 1: Synthesis of 4-(benzyloxy)-4-oxobutanoic acid (3)

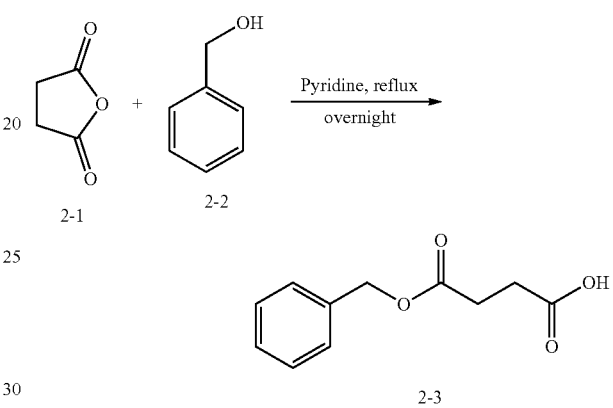

In a 500 mL round bottom flask, succinic anhydride 2-1 (25 g, 250 mmol) and pyridine (250 mL) were added at room temperature. To this mixture was added benzyl alcohol 2-2 (27.02 g, 250 mmol). The reaction was then refluxed overnight under nitrogen. Next day, the heating was shut off and after cooling the reaction flask, the reaction mixture was evaporated under high vacuum to remove most of the pyridine. The crude product 4-(benzyloxy)-4-oxobutanoic acid 2-3 (52.05 g) thus obtained was directly for the next step without further purification. Yield: 100% crude.

Step 2: Synthesis of benzyl ((2,2-dimethyl-1,3-dioxolan-4-yl)methyl) succinate (2-5)

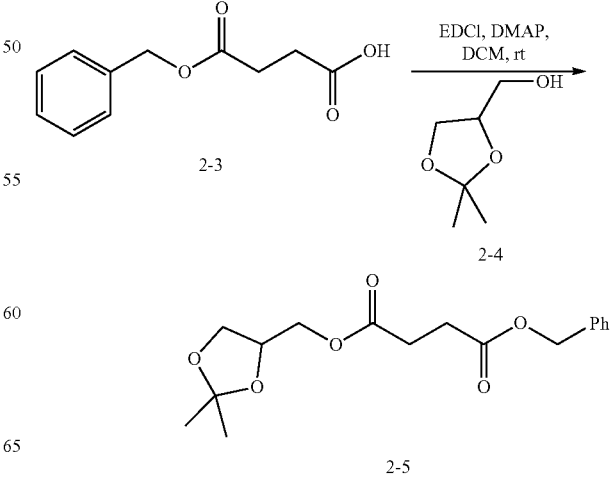

In a 2000 mL round bottom flask, of 4-(benzyloxy)-4-oxobutanoic acid 2-3 (52.05 g, 250 mmol), solketal 2-4 (33.04 g, 250 mmol) and dichloromethane (850 mL) were added at room temperature. To this mixture was added EDCI (71.88 g, 375 mmol) and DMAP (4.88 g, 37.5 mmol). The reaction was stirred overnight at room temperature under nitrogen. Next day, after checking the TLC for completion of the reaction, water was added to the reaction mixture and the organic layer was separated. The organic layer was washed with sat. aq. NaHCO$_3$ solution and brine. Then the organic layer was concentrated under vacuum and dried. The crude product obtained was purified by silica gel chromatography (0-30% ethyl acetate/hexanes) to furnish pure benzyl ((2,2-dimethyl-1,3-dioxolan-4-yl)methyl) succinate 2-5 (56.2 g). Yield: 70%.

Step 3: Synthesis of benzyl (2,3-dihydroxypropyl) succinate (2-6)

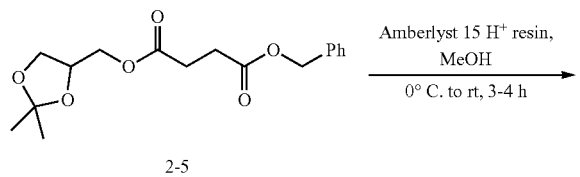

2-5

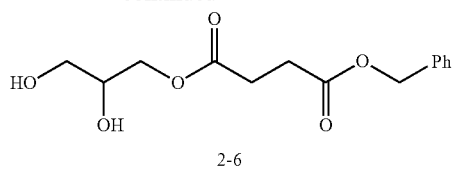

2-6

In a 1000 mL round bottom flask, of benzyl ((2,2-dimethyl-1,3-dioxolan-4-yl)methyl) succinate 2-5 (26 g, 80.68 mmol) and methanol (260 mL) were added. The reaction mixture was cooled to 0° C. by ice bath and then Amberlyst 15 H$^+$ resin (15 g) was added to it. The reaction mixture was allowed to gradually come to room temperature while stirring for 4 h under nitrogen. After checking the TLC for completion of the reaction the reaction mixture was filtered over a pad of celite and filtrate was concentrated under vacuum. The crude product obtained was purified by silica gel chromatography (40-100% ethyl acetate/hexanes) to furnish pure benzyl (2,3-dihydroxypropyl) succinate 2-6 (10.28 g). Yield: 45%.

Step 4: Synthesis of benzyl (2,3-bis(octanoyloxy)propyl) succinate (2-8)

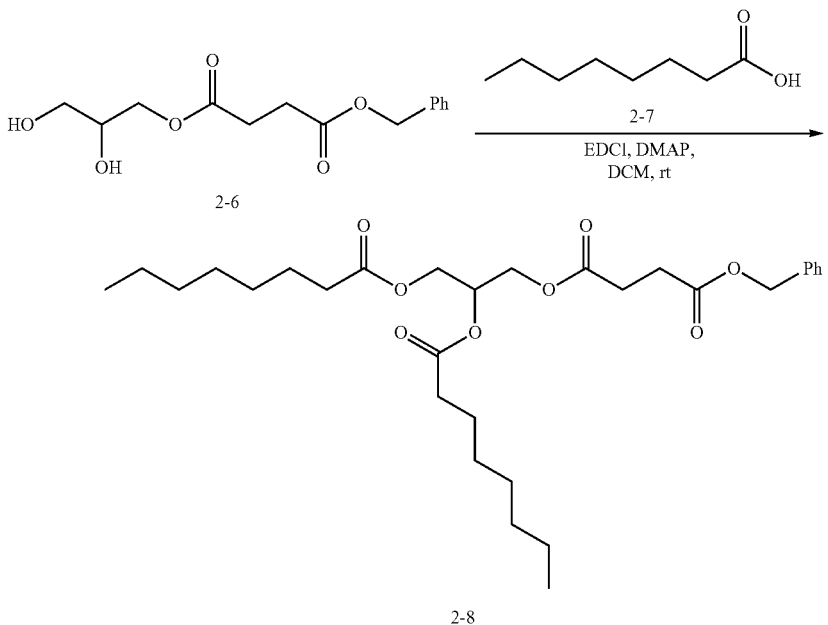

In a 250 mL round bottom flask, benzyl (2,3-dihydroxypropyl) succinate 2-6 (5.14 g, 18.21 mmol), caprylic acid 2-7 (5.79 g, 40.06 mmol), EDCI (10.47 g, 54.63 mmol), DMAP (0.67 g, 5.463 mmol) and dichloromethane (100 mL) were added at room temperature. The reaction was stirred overnight at room temperature under nitrogen. Next day, after checking the TLC for completion of the reaction, water was added to the reaction mixture and the organic layer was separated. The organic layer was washed with sat. aq. NaHCO$_3$ solution and brine. Then the organic layer was concentrated under vacuum and dried. The crude product obtained was purified by silica gel chromatography (0-30% ethyl acetate/hexanes) to furnish pure benzyl (2,3-bis(octanoyloxy)propyl) succinate 2-8 (56.2 g). Yield: 66%.

Step 5: Synthesis of 4-(2,3-bis(octanoyloxy)propoxy)-4-oxobutanoic acid (2-9)

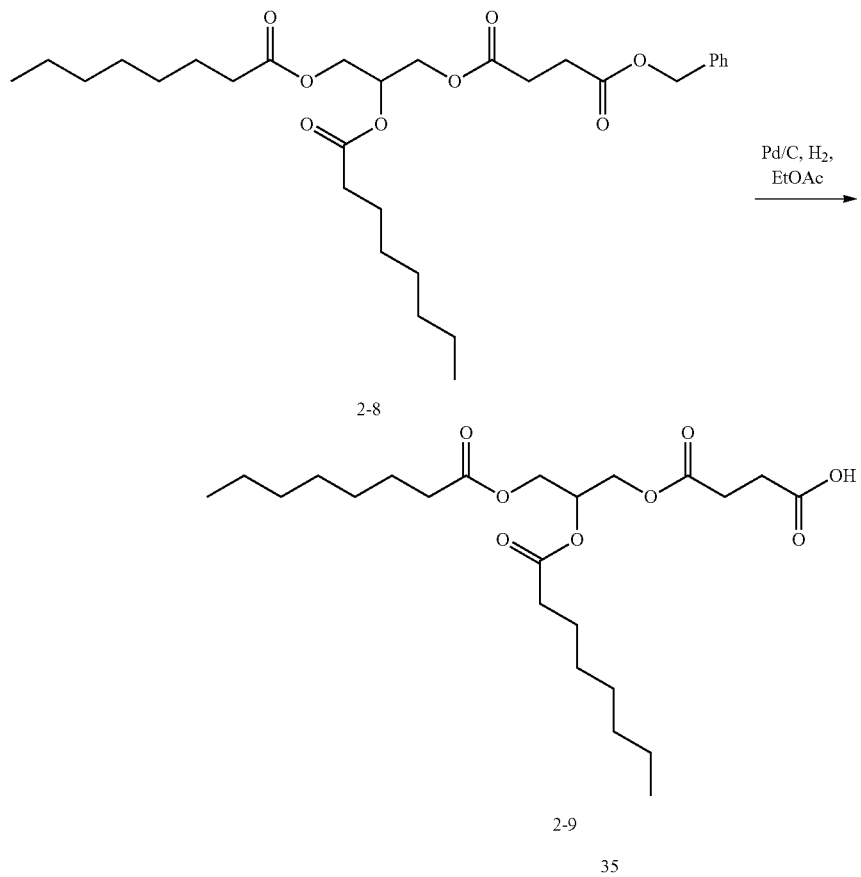

In a 200 mL round bottom flask benzyl (2,3-bis(octanoyloxy)propyl) succinate 2-8 (6.35 g, 11.88 mmol), ethyl acetate (60 mL) and Pd/C (5% wt) (1 g) were added at room temperature. The flask was evacuated and purged with hydrogen 2 times. Then the reaction mixture was stirred at room temperature overnight. Next day, the reaction mixture was carefully filtered over a pad of celite. The filtrate was concentrated under vacuum to remove the solvent. The crude product obtained was dried for 2 days under high vacuum to remove the residual solvent traces and furnish pure 4-(2,3-bis(octanoyloxy)propoxy)-4-oxobutanoic acid 2-9 (5.17 g). Yield: 98%.

Step 6: Synthesis of 2,3-bis(octanoyloxy)propyl ((2,2-dimethyl-1,3-dioxolan-4-yl)methyl) succinate (2-10)

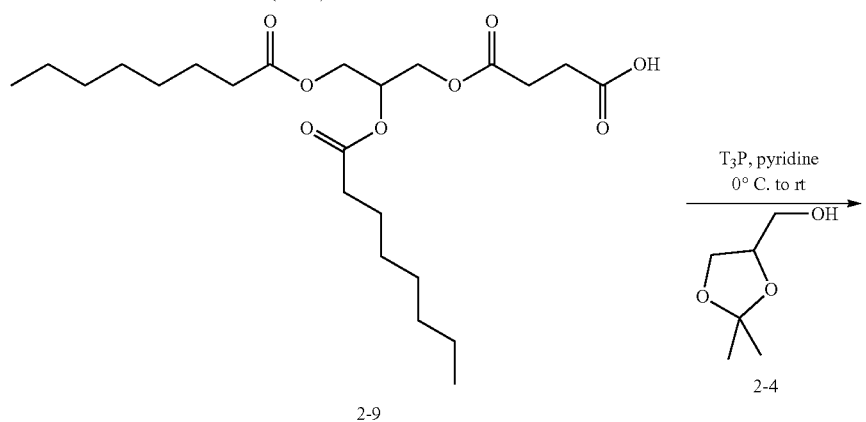

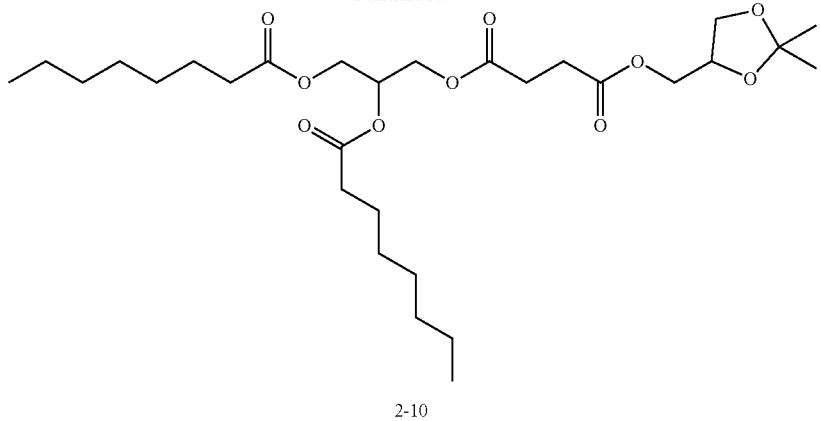

2-10

In a 100 mL round bottom flask 4-(2,3-bis(octanoyloxy) propoxy)-4-oxobutanoic acid 2-9 (3.92 g, 8.82 mmol), solketal 2-4 (1.16 g, 8.82 mmol), T$_3$P (50 wt % in ethyl acetate) (11.23 g, 35.28 mmol) and pyridine (50 mL) were added at 0° C. The reaction was slowly allowed to come to room temperature and stirred overnight under nitrogen. Next day, after checking the TLC for completion of the reaction the reaction mixture was concentrated under vacuum and dried. The crude product obtained was purified by silica gel chromatography (0-30% ethyl acetate/hexanes) to furnish furnish pure 2,3-bis(octanoyloxy)propyl ((2,2-dimethyl-1,3-dioxolan-4-yl)methyl) succinate 2-10 (2.21 g). Yield: 45%.

Step 7: Synthesis of 2,3-bis(octanoyloxy)propyl (2,3-dihydroxypropyl) succinate (2-11)

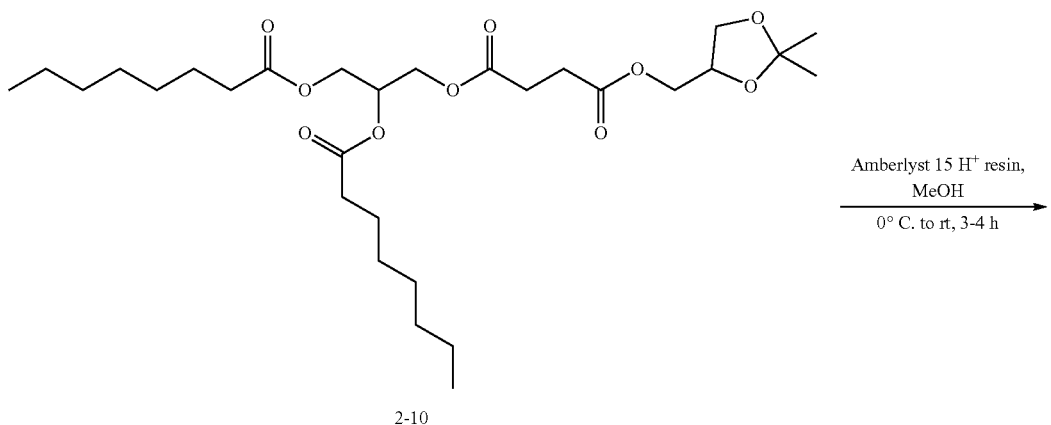

2-10

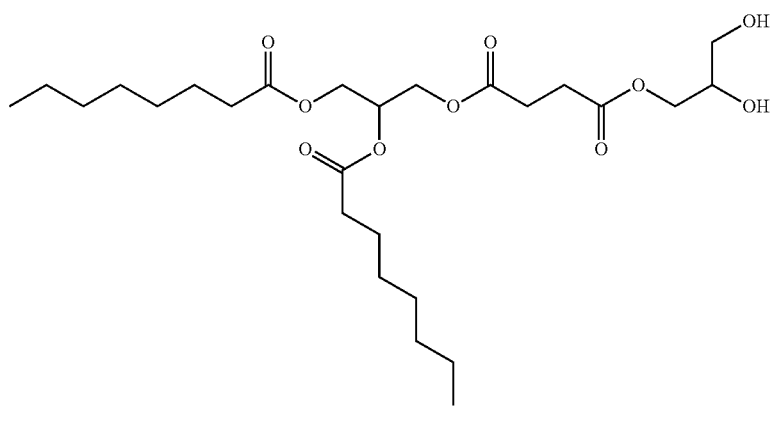

2-11

In a 50 mL round bottom flask 2,3-bis(octanoyloxy) propyl ((2,2-dimethyl-1,3-dioxolan-4-yl)methyl) succinate 2-10 (2.21 g, 3.956 mmol and methanol (25 mL)) were added. The reaction mixture was cooled to 0° C. by ice bath and then Amberlyst 15 H+ resin (1.47 g) was added to it. The reaction mixture was allowed to gradually come to room temperature while stirring for 4 h under nitrogen. After checking the TLC for completion of the reaction the reaction mixture was filtered over a pad of celite and filtrate was concentrated under vacuum to get the crude product. The crude product obtained was further dried for 2 days under high vacuum to remove the residual solvent traces to furnish pure 2,3-bis(octanoyloxy)propyl (2,3-dihydroxypropyl) succinate 2-11 (1.60 g). Yield: 78%.

Step 8: Synthesis of bis (2,3-bis(octanoyloxy)propyl) succinate (2-12)

Figure 2:
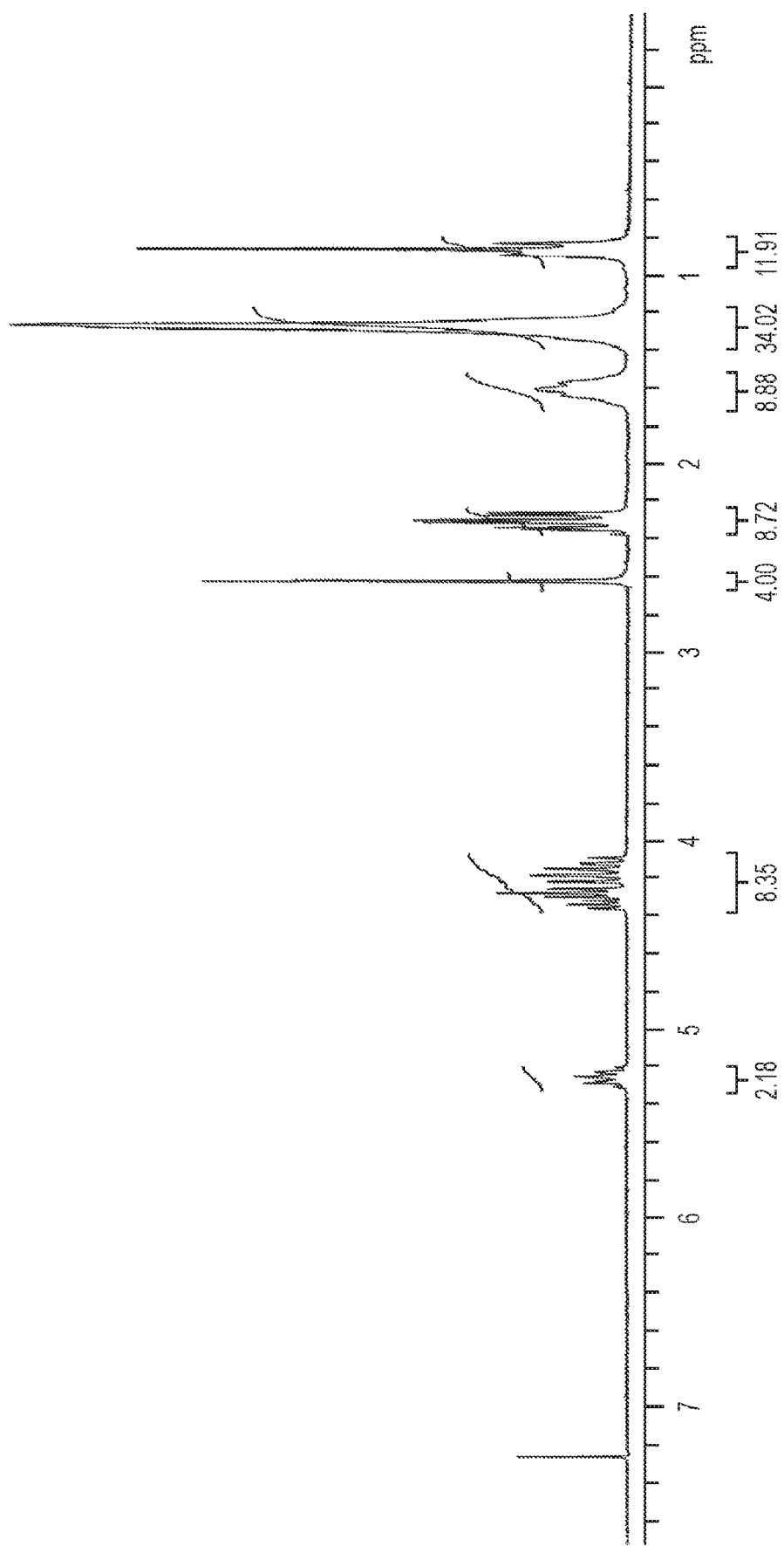
FIG. 2. Example NMR of compound I-30.

In a 100 mL round bottom flask compound 2-11 (1.2 g, 0.0023 mol), caprylic acid (0.732 g, 0.0051 mol), EDCI (1.545 g, 0.0081 mol), DMAP (0.098 g, 8.03 mmol) and dichloromethane (100 mL) were added at room temperature. The reaction was stirred overnight at room temperature under nitrogen. Next day, after checking the TLC for completion of the reaction, water was added to the reaction mixture and the organic layer was separated. The organic layer was washed with sat. aq. NaHCO₃ solution and brine. Then the organic layer was concentrated under vacuum and dried. The crude product obtained was purified by silica gel chromatography (0-40% ethyl acetate/hexanes) to furnish pure bis (2,3-bis(octanoyloxy)propyl) succinate 2-12 (1.5 g, yield: 84%) as a liquid with >97% NMR purity. Example NMR spectra is presented in FIG. 2.

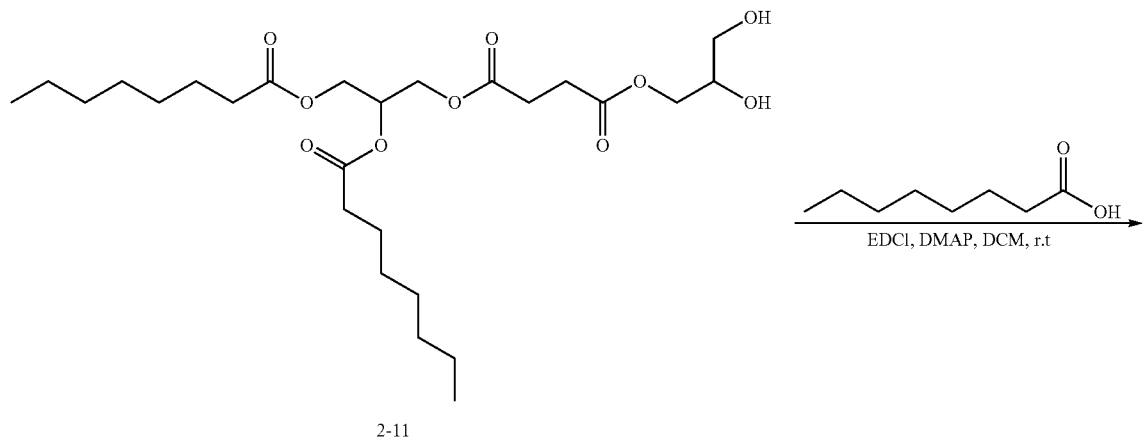

2-11

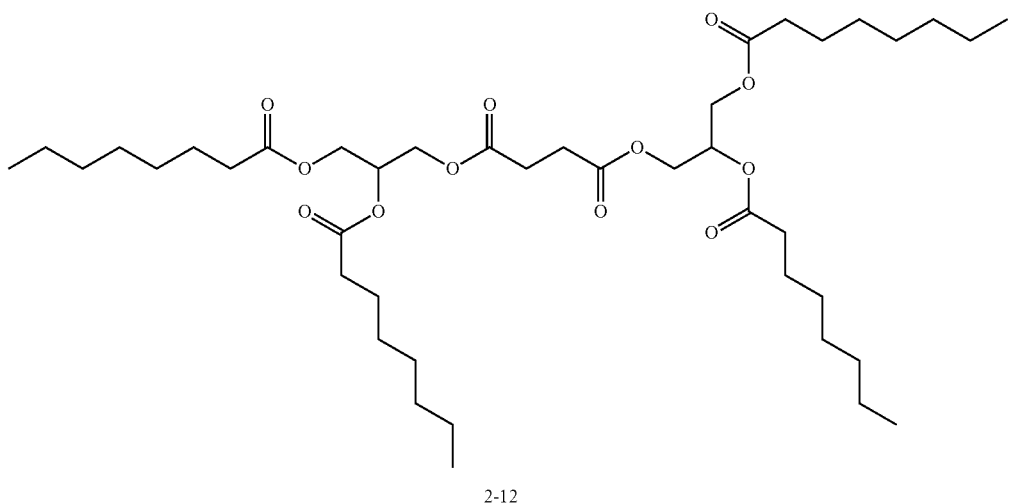

2-12

Additional compounds were prepared using similar procedures and/or chemistry as demonstrated in the examples, e.g., certain compounds in Table 1.

Example 3. Test of Certain Properties of Example Compounds

Properties of provided compounds and compositions can be readily tested, including using a number of methods widely known and practiced in the art, in accordance with the present disclosure. For example, viscosity and/or taste of provided compounds can be readily tested. In some embodiments, viscosity was assessed by testing whether a provided compound could readily flow out of a vial or be swirled. In some embodiments, viscosity was assessed by testing whether a provided compound could be administered by direct drinking by a subject. In some embodiments, taste was assessed by testing whether a provided compound could be administered by direct drinking by a subject. In some embodiments, certain example compounds with free hydroxyl groups were found to have high viscosity. In some embodiments, certain example compounds with free carboxylic acid groups were found to have high viscosity. In some embodiments, certain example compounds with free hydroxyl carboxylic acid groups were found to have high viscosity. In some embodiments, certain example compounds without free hydroxyl or carboxylic acid groups, such as 1-29 and I-30, were found to have good flow property for formulation. In some embodiments, provided compounds, such as I-29 and I-30, have lower viscosity than glycerol, e.g., no more than 1200, 1100, 1000, 900, 800, 700, 600, 500, 400, 300, 200, 100, 90, 80, 70, 60, 50, 40, 30, 20, 10, 9, 8, 7, 6, 5, 4, 3, 2, or 1 cp, In some embodiments, provided compounds, such as I-29 and I-30, have lower viscosity than glycerol, e.g., no more than 900, 800, 700, 600, 500, 400, 300, 200, 100, 90, 80, 70, 60, 50, 40, 30, 20, 10, 9, 8, 7, 6, 5, 4, 3, 2, or 1 cp at room temperature.

In some embodiments, certain example compounds, for example, certain compounds with free carboxylic acid groups of succinic acid, were found to be very bitter and may not be as good for oral administration and/or patient compliance. In some embodiments, provided example compounds, such as I-29 and I-30, were found to be more palatable for oral formulations.

In some embodiments, provided compounds are effective when tested in in vitro and in vivo assays, e.g., one or more in vitro and in vivo disease models (e.g., for those described in the present disclosure). For example, provided compounds demonstrated unexpected properties in an example assay involving multiple groups of mice: normal mice as a control, untreated long chain fatty acid oxidation disorder mice as a control, long chain fatty acid oxidation disorder mice treated with triheptanoin, and long chain fatty acid oxidation disorder mice treated with provided compounds, for example, succinate diglycerol tetra-butyric acid (I-29). The animals' temperatures are monitored during a cold room challenge. The rate of temperature decline is monitored as well as the mice's ability to recover once they are removed from the cold room. In some embodiments, provided compounds, for example, succinate diglycerol tetra-butyric acid, provide results similar to, or even better than, triheptanoin. As one of ordinary skill in the art appreciates, triheptanoin shows certain benefits in human, although it may not be suitable for treating propionic acidemia patients.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The invention claimed is:

1. A compound having the structure of formula I-a:

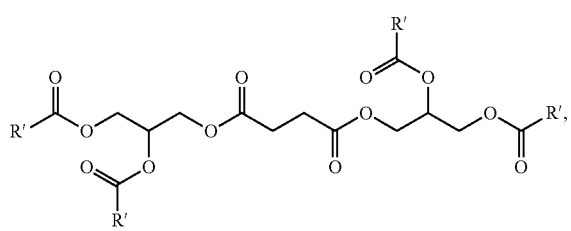

I-a or a salt thereof, wherein R' is $C_3$-$C_7$ linear alkyl.

2. The compound of claim 1, wherein the compound is
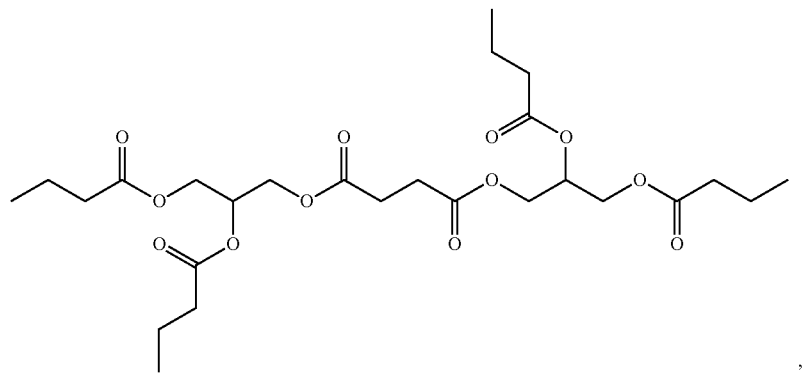 [SMILES: CCCC(=O)OCC(COC(=O)CCC(=O)OCC(COC(=O)CCC)OC(=O)CCC)OC(=O)CCC]
or a pharmaceutically acceptable salt thereof.